United States Patent
Hansell et al.

(10) Patent No.: US 8,613,771 B2
(45) Date of Patent: Dec. 24, 2013

(54) ARTIFICIAL DISC

(75) Inventors: Noah Hansell, King of Prussia, PA (US); Jeff Bennett, Pottstown, PA (US); Michael Lee Boyer, II, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 779 days.

(21) Appl. No.: 12/466,680

(22) Filed: May 15, 2009

(65) Prior Publication Data

US 2010/0292801 A1  Nov. 18, 2010

(51) Int. Cl.
*A61F 2/44* (2006.01)

(52) U.S. Cl.
USPC ............................. 623/17.15; 623/17.16

(58) Field of Classification Search
USPC ................. 623/17.11, 17.15–17.16
See application file for complete search history.

(56) References Cited

U.S. PATENT DOCUMENTS

| | | | |
|---|---|---|---|
| 5,824,094 A * | 10/1998 | Serhan et al. | 623/17.16 |
| 7,250,060 B2 * | 7/2007 | Trieu | 623/17.15 |
| 2008/0172129 A1 * | 7/2008 | Kim et al. | 623/17.16 |

* cited by examiner

*Primary Examiner* — David Isabella
*Assistant Examiner* — Jacqueline Woznicki

(57) ABSTRACT

An intervertebral artificial disc is provided with a first endplate having a plurality of protrusions for attaching to an adjacent vertebrae and an extension portion extending towards a second adjacent vertebrae. A second endplate is provided with a plurality of protrusions for attaching to a second adjacent vertebrae and an extension portion extending towards the first adjacent vertebrae. A flexible member having an upper portion and a lower portion and a slider plate positioned within the upper portion of the flexible member is also provided. The extension portion of the first endplate is adapted to fit within a first cavity in the upper portion of the flexible member and the extension portion of the second endplate is adapted to fit within a second cavity in the lower portion of the flexible member.

19 Claims, 63 Drawing Sheets

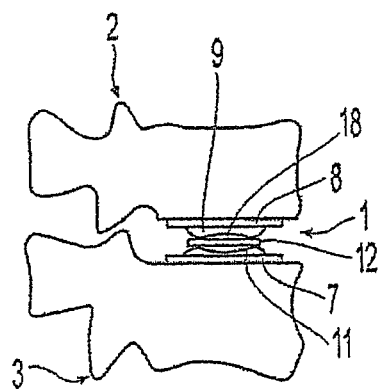
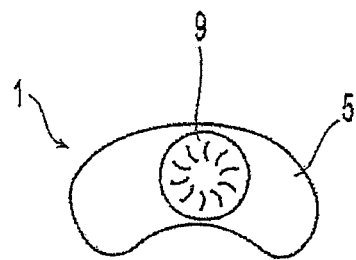
Fig. 1A       Fig. 1B
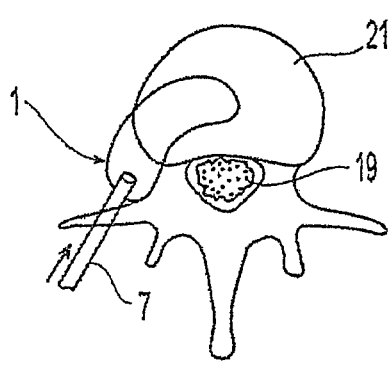
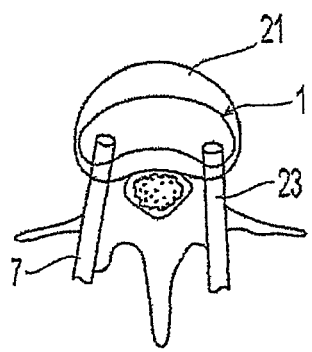
Fig. 2A       Fig. 2B
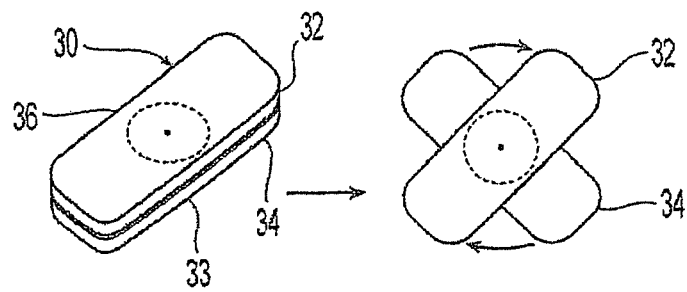
Fig. 3

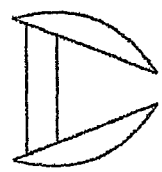
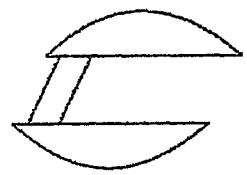
Fig. 12A          Fig. 12B
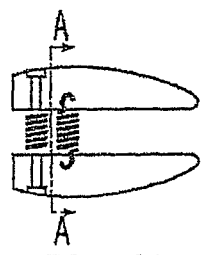
Fig. 13          Fig. 14
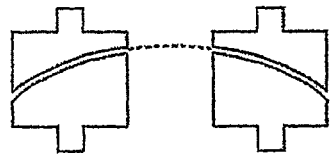
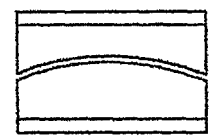
Fig. 15          Fig. 16
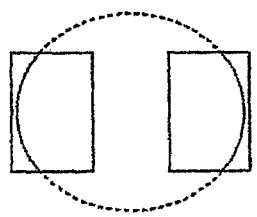
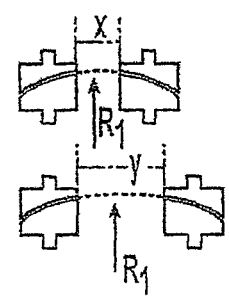
Fig. 17          Fig. 18

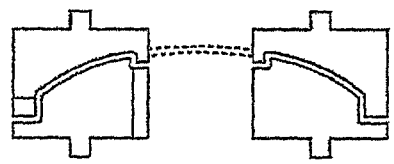 
Fig. 19    Fig. 20
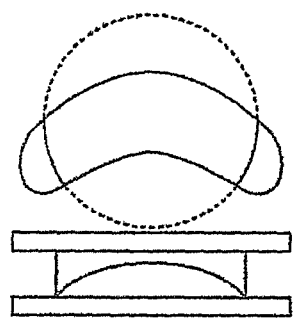 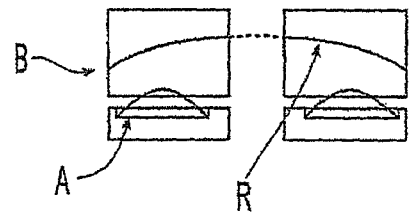
Fig. 21    Fig. 22
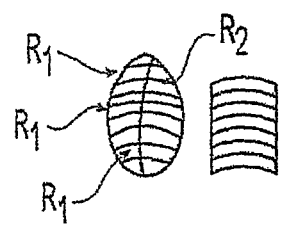 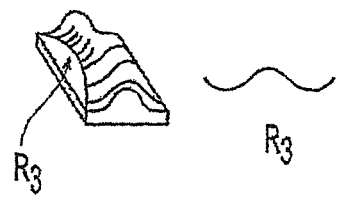
Fig. 23    Fig. 24

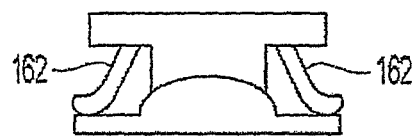
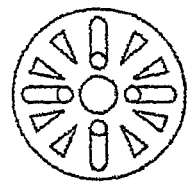
Fig. 33    Fig. 34
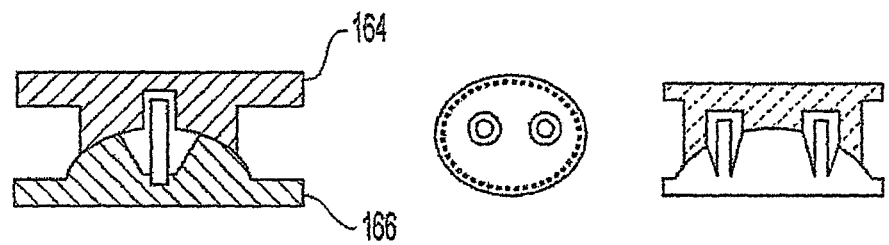
Fig. 35    Fig. 36A    Fig. 36B
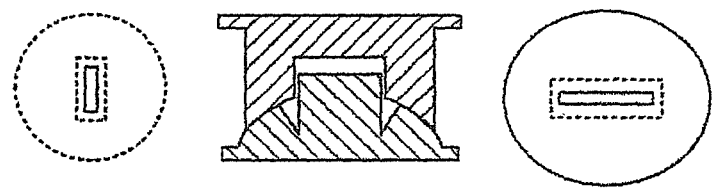
Fig. 37A    Fig. 37B    Fig. 37C
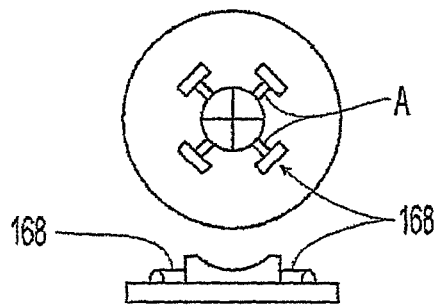
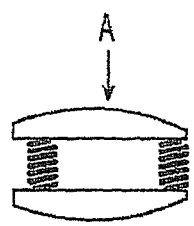
Fig. 38    Fig. 39

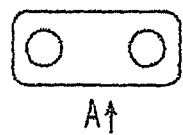
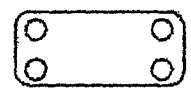
*Fig. 40*     *Fig. 41*
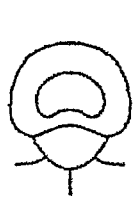 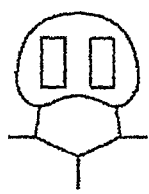 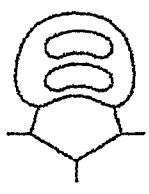 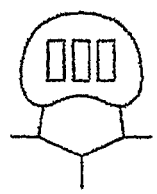
*Fig. 42A*   *Fig. 42B*   *Fig. 42C*   *Fig. 42D*
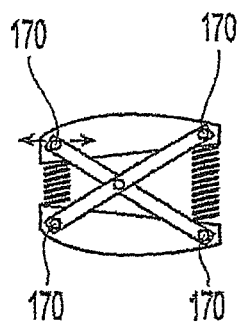  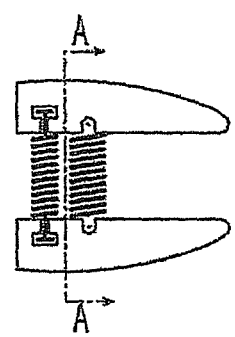
*Fig. 43*     *Fig. 44*

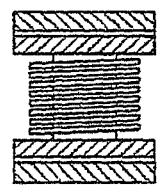
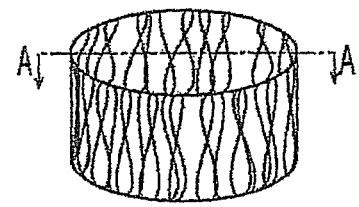
Fig. 45    Fig. 46
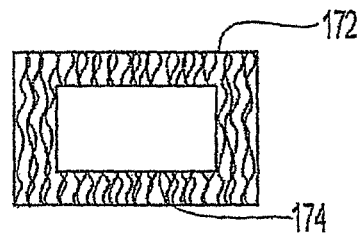
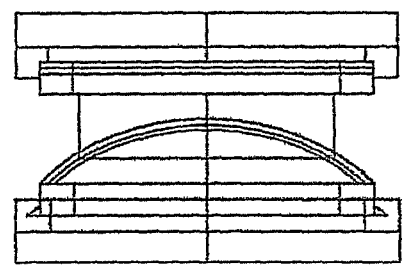
Fig. 47    Fig. 48
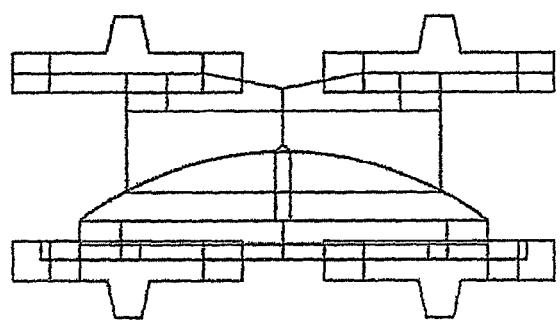
Fig. 49

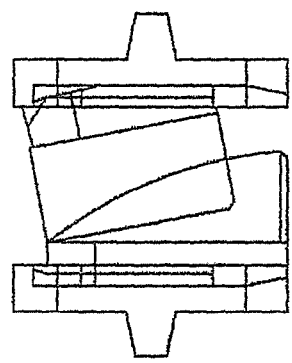
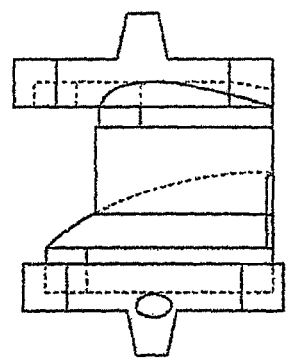
Fig. 50A        Fig. 50B
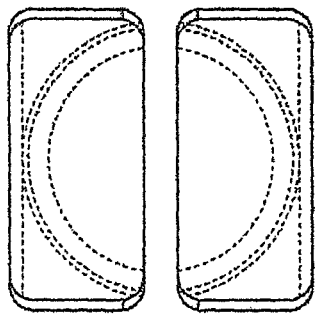
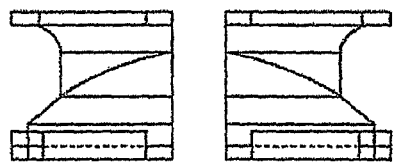
Fig. 51         Fig. 52
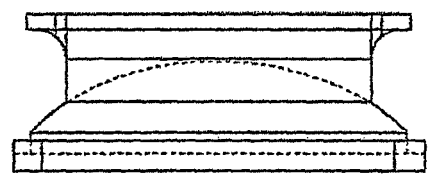
Fig. 53

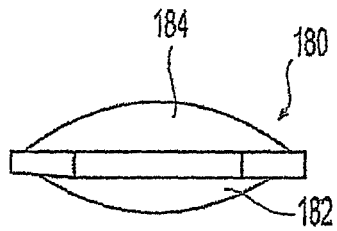 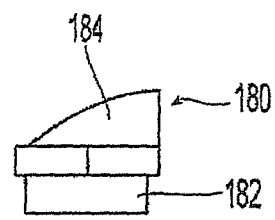
*Fig. 57A*    *Fig. 57B*
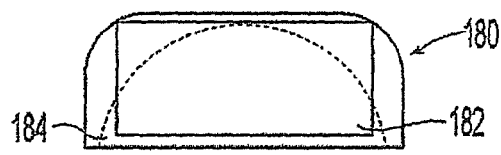
*Fig. 57C*
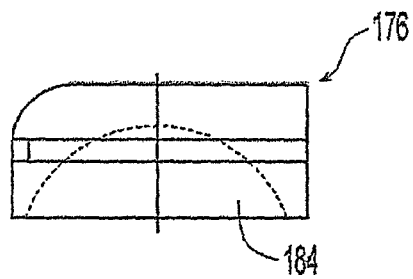 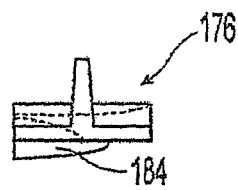
*Fig. 58A*    *Fig. 58B*
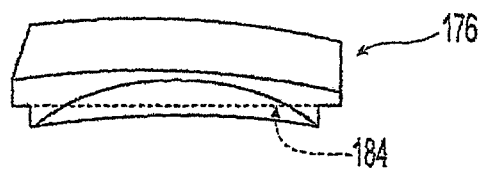
*Fig. 58C*

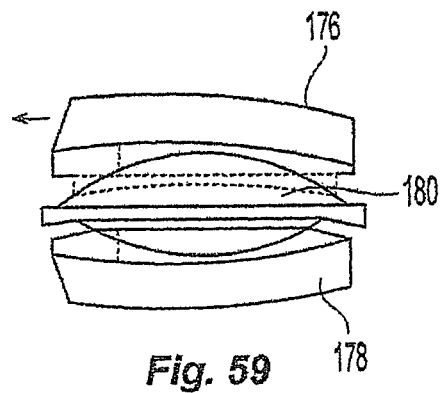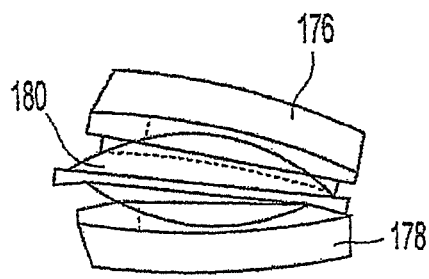
Fig. 59   Fig. 60
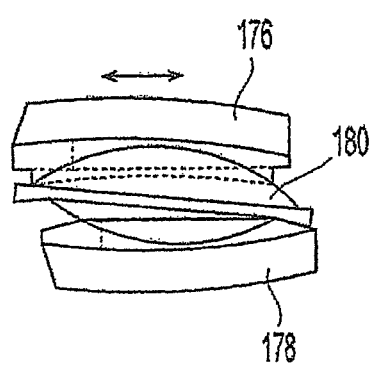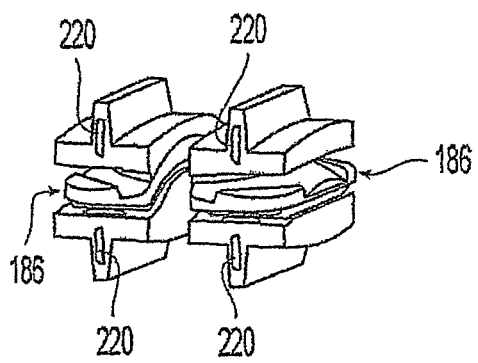
Fig. 61   Fig. 62A
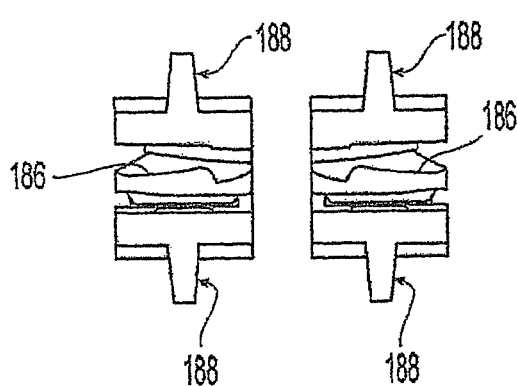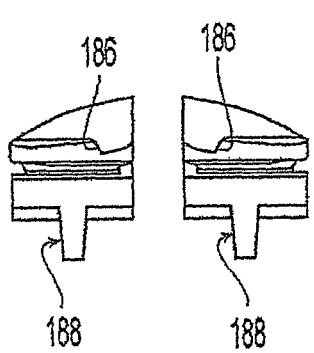
Fig. 62B   Fig. 62C

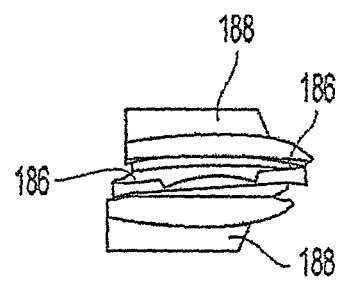
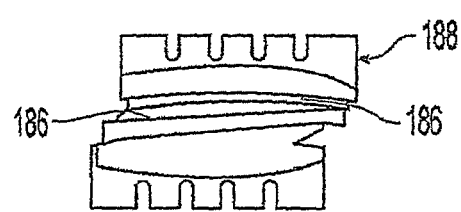
*Fig. 62D*  *Fig. 62E*
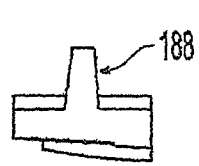
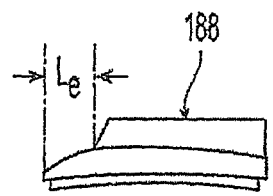
*Fig. 62F*  *Fig. 62G*
*Fig. 62H*

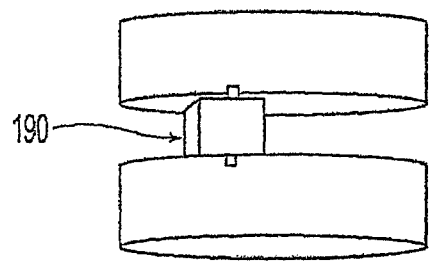
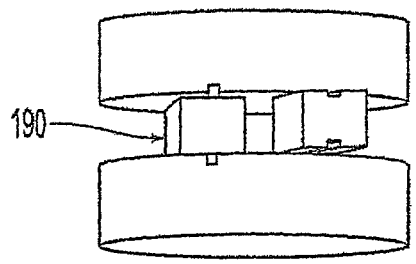
Fig. 63A             Fig. 63B
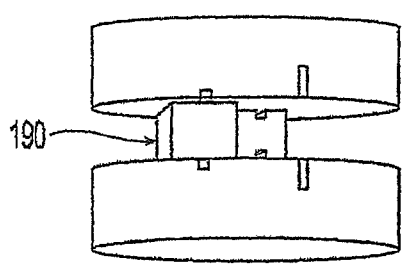
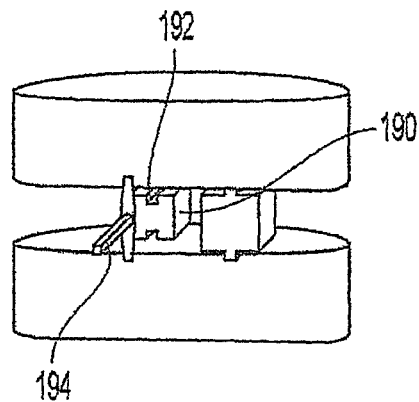
Fig. 64             Fig. 65
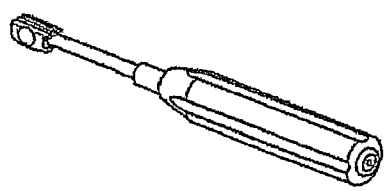
Fig. 66

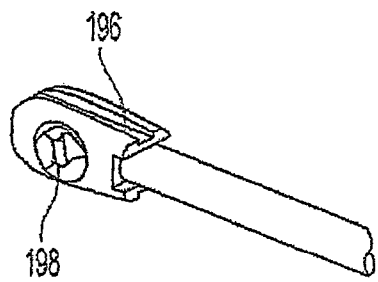
Fig. 67
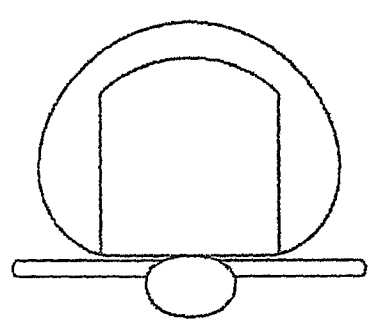 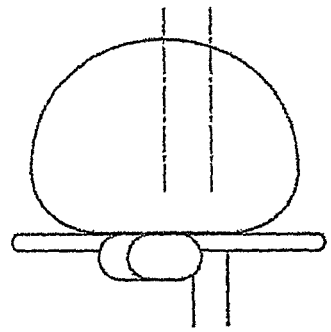
Fig. 68  Fig. 69
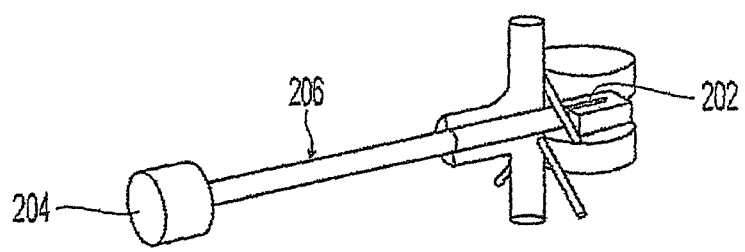
Fig. 70

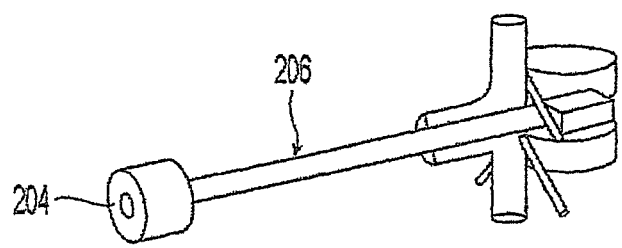
Fig. 71
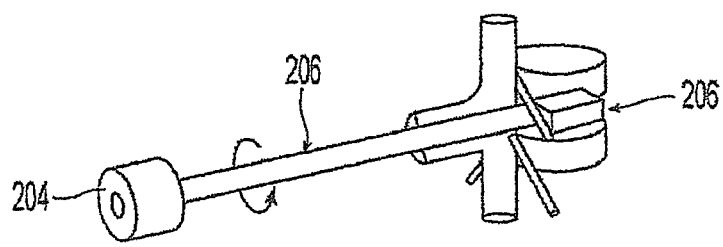
Fig. 72
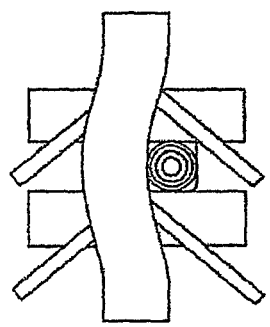 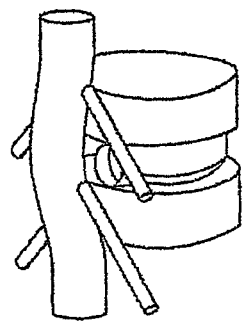
Fig. 73      Fig. 74

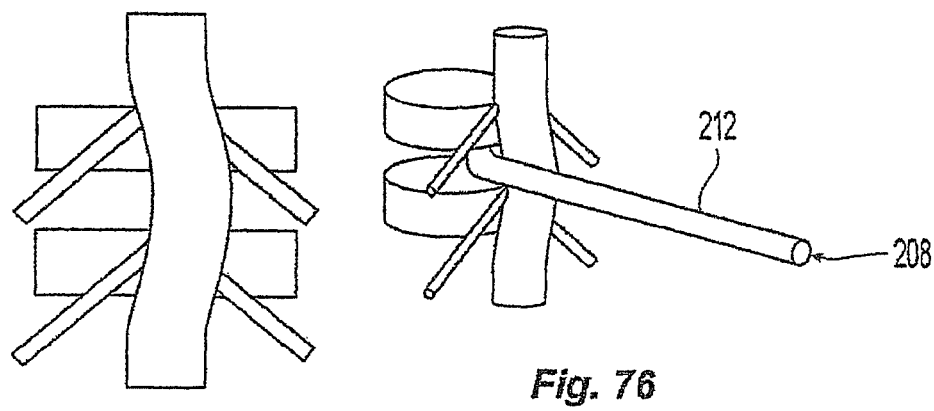
Fig. 75
Fig. 76
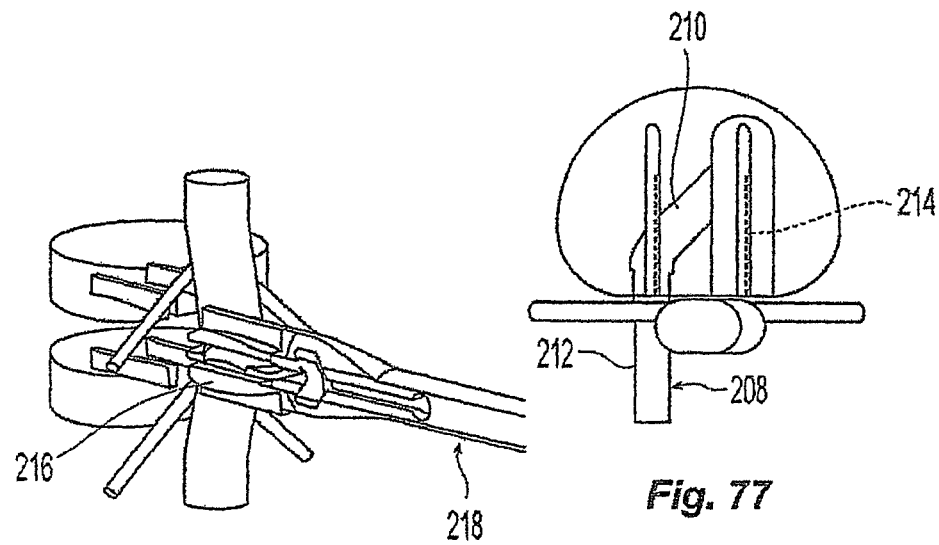
Fig. 77
Fig. 78

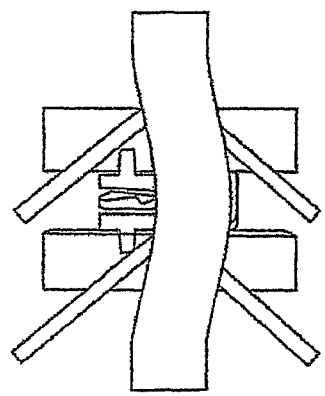
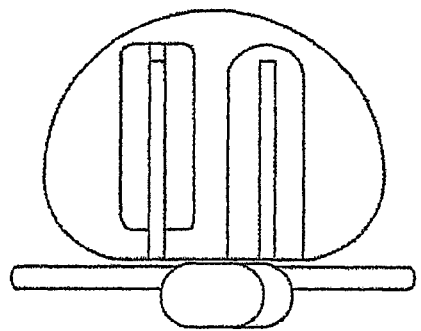
Fig. 79    Fig. 80
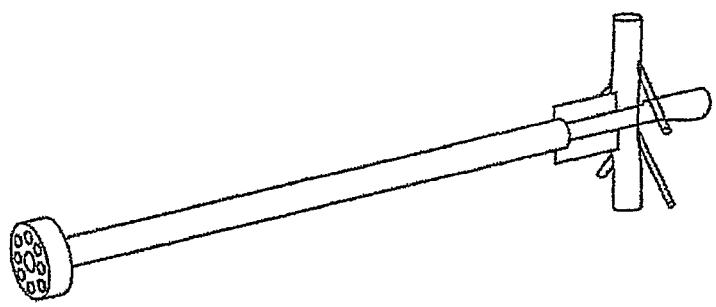
Fig. 81
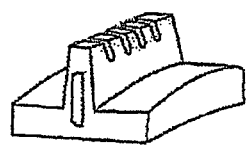
Fig. 82

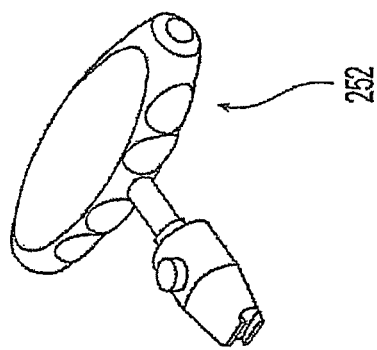
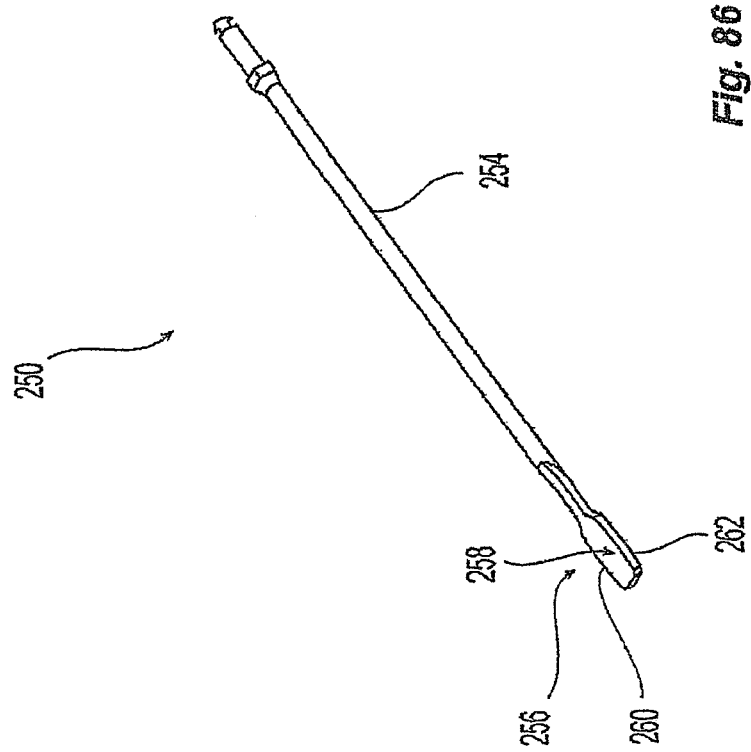
Fig. 86

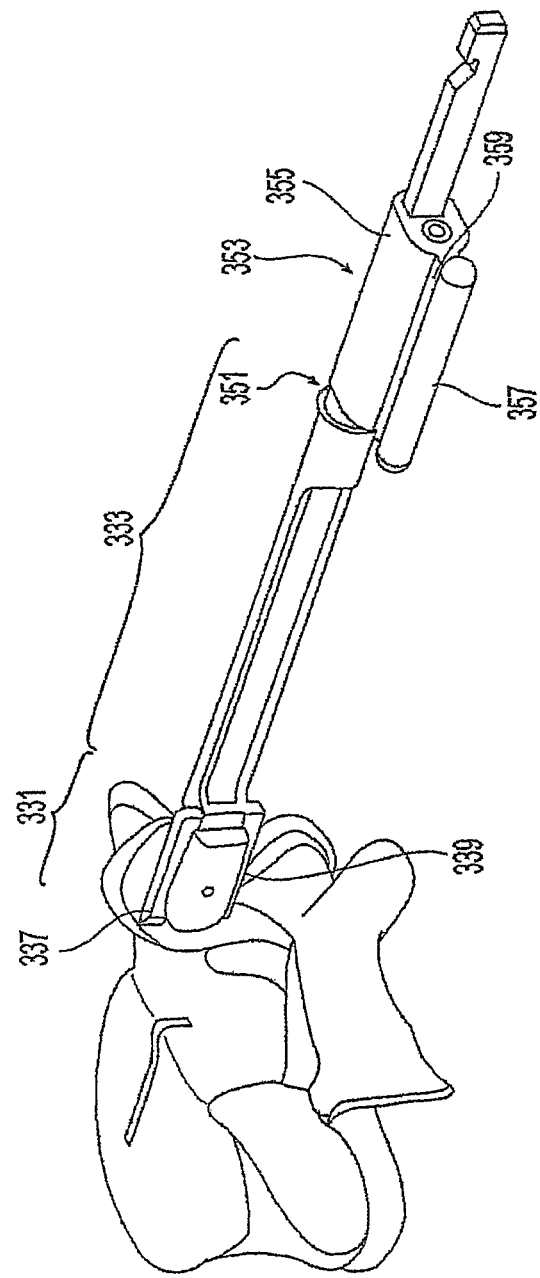

ARTIFICIAL DISC

FIELD OF THE INVENTION

The present invention relates to a prosthetic spinal disc for fully or partially replacing a damaged disc between two vertebrae of a spine. The present invention also relates to a method for implanting a prosthetic spinal disc via posterior or posterior lateral implantation, although other implantation approaches may also be used.

BACKGROUND OF THE INVENTION

The vertebrate spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The center of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosis ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The annulus of the disc is a tough, outer fibrous ring which binds together adjacent vertebrae. The fibrous portion, which is much like a laminated automobile tire, measures about 10 to 15 millimeters in height and about 15 to 20 millimeters in thickness. The fibers of the annulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the annulus is the nucleus. The healthy nucleus is largely a gel like substance having high water content, and like air in a tire, serves to keep the annulus tight yet flexible. The nucleus-gel moves slightly within the annulus when force is exerted on the adjacent vertebrae while bending, lifting, and other motions.

The spinal disc may be displaced or damaged due to trauma, disease, degenerative defects, or wear over an extended period. A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with disc degeneration, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all disc motion is lost in the fused segment. Ultimately, this procedure places a greater stress on the discs adjacent to the fused segment as they compensate for lack of motion, perhaps leading to premature degeneration of those adjacent discs.

As an alternative to vertebral fusion, various prosthetic discs have been developed. The first prosthetics embody a wide variety of ideas, such as ball bearings, springs, metal spikes and other perceived aids. These prosthetics are all made to replace the entire intervertebral disc space and are large and rigid. Beyond the questionable applicability of the devices is the inherent difficulties encountered during implantation. Due to their size and inflexibility, these devices require an anterior implantation approach as the barriers presented by the lamina and, more importantly, the spinal cord and nerve roots are difficult to avoid during posterior or posterior lateral implantation procedure.

Anterior implantation, however, can involve numerous risks during surgery. Various organs present physical obstacles as the surgeon attempts to access the damaged disc area from the front of the patient. After an incision into the patient's abdomen, the surgeon is forced to navigate around interfering organs and carefully move them aside in order to gain access to the spine. One risk to the patient from an anterior approach is that these organs may be inadvertently damaged during the procedure.

In contrast, a posterior approach to intervertebral disc implantation avoids the risks of damaging body organs. Despite this advantage, a posterior approach also raises other difficulties that have discouraged it use. For instance, a posterior approach can introduce a risk of damaging the spinal cord. Additionally, vertebral body geometry allows only limited access to the intervertebral discs. Thus, the key to successful posterior or posterior lateral implantation is avoiding contact with the spinal cord, as well as being able to place an implant through a limited special area due to the shape of the vertebral bones. Because an anterior approach does not present the space limitations that occur with a posterior approach, current prosthetic disc designs are too bulky to use safely with a posterior approach. Therefore, a need exists for a method of surgically implanting a prosthetic spinal disc into the intervertebral disc space through a posterior approach with minimal contact with the spinal cord.

SUMMARY OF THE INVENTION

In general, the present invention is directed toward prosthetic disc designs. In one particular embodiment, an intervertebral artificial disc is provided with a first endplate having a plurality of protrusions for attaching to an adjacent vertebrae and an extension portion extending towards a second adjacent vertebrae. A second endplate is provided with a plurality of keels for attaching to a second adjacent vertebrae and an extension portion extending towards the first adjacent vertebrae. A flexible member having an upper portion and a lower portion and a slider plate positioned within the upper portion of the flexible member is also provided. The extension portion of the first endplate is adapted to fit within a first cavity in the upper portion of the flexible member and the extension portion of the second endplate is adapted to fit within a second cavity in the lower portion of the flexible member.

BRIEF DESCRIPTION OF THE DRAWINGS

FIG. 1A is a side view of sequentially aligned vertebral bodies, such as are found in the cervical, thoracic and lumbar spine, and a posterior prosthetic spinal disc located between the vertebral bodies;

FIG. 1B is a top view of one embodiment of a prosthetic spinal disc of the present invention;

FIGS. 2A-B illustrate a surgical approach that may be used for inserting the prosthetic spinal disc of FIG. IB;

FIG. 3 is a view of a collapsed posterior prosthetic spinal disc that can be opened via scissor action;

FIGS. 12A-B and 13-14 illustrate the use of compressed elements in the present invention;

FIGS. 15-26 illustrate the use of varying types interfacing surfaces in the present invention to achieve or restrict movement in different directions;

FIGS. 30-45 illustrate the use of stiffness mechanisms, torsion bars, tension and compression springs that may be used in the present invention;

FIGS. 46-47 show one embodiment of the present invention utilizing a braided reinforcing material around a balloon or bladder;

FIGS. 48-49 and 50A-B show one example of the present invention;

FIGS. 51-54 illustrate an embodiment of the present invention having a fixed IAR;

FIGS. 55-61 show an example of the present invention having two articulating surfaces;

FIGS. 62A-H, 63A-B, and 64-67 further illustrate prosthetic disc designs of the present invention and the use of a trial and chisel for preparing the treated area for insertion of disc assemblies;

FIGS. 68-81 illustrate steps used for preparing a treated area for insertion of a prosthetic spinal disc using a posterior approach;

FIG. 82 is an illustration of one embodiment of a prosthetic disc of the present invention;

FIG. 86 illustrates one embodiment of a tool used in the methods of the present invention;

FIGS. 88-111 illustrate various tools used in an embodiment of the methods of the present invention;

DETAILED DESCRIPTION OF THE INVENTION

Figures 4A, 4B:
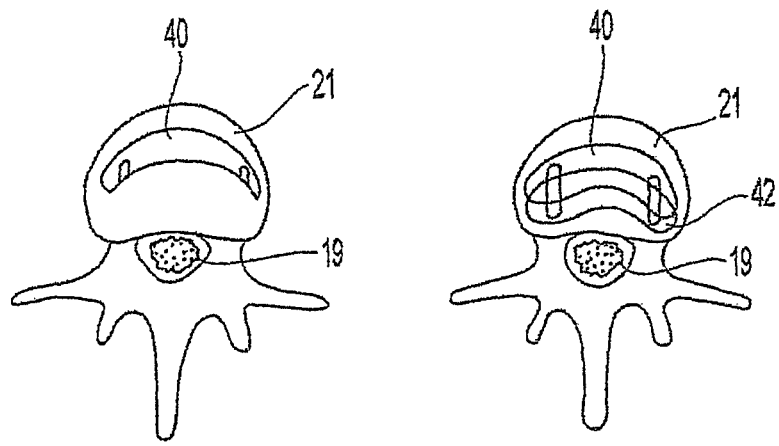
FIGS. 4A-B are views of a segmented posterior prosthetic spinal disc and its assembly between vertebral bodies.

The present invention relates generally to a posterior prosthetic spinal disc for replacing a damaged disc between two vertebrae of a spine. The present invention also relates to a method for implanting a prosthetic spinal disc via posterior or posterior lateral implantation. In particular, the present invention encompasses a method for implanting the prosthetic spinal disc while avoiding or minimizing contact with the spinal cord.

As described in detail below, the prosthetic spinal disc may be articulating or non-articulating. In addition, the prosthetic disc may be formed of one, two, three or more units. For example, two units may be disposed in the medial-lateral direction at spaced apart locations, and the upper and lower portions of each unit have interfacing surfaces that forms an arc in the anterior-posterior direction.

If multiple units are used, they may be spaced apart from each other or connected to prior to insertion in the patient or as they are being positioned within the body. The ability to connect the units together may allow the prosthetic disc to be inserted using a posterior approach with less risk of injuring the spinal cord, nerve rootlets, lamina or the like. In addition, using a plurality of units, either connected or disposed in spaced apart locations, allows individual units to be interchangeable with a multiplicity of designs or configurations that allow the physician to address different physical conditions of the treated area of the spine and to custom tailor the range of motion that the prosthetic disc will permit.

Several embodiments of the invention illustrate different examples of how the interfacing surfaces of an articulating prosthetic disc may be formed. For instance, articulation may be accomplished with one interfacing surface, such as a ball and joint (see e.g., FIG. 21), or alternatively may be accomplished with two or more interfacing surfaces such as a core disposed between an upper and lower seating surface (see, e.g., Fig. IA). The configuration of the surface contact may vary to permit or restrict different types and ranges of motion of the treated area. Thus, the contact profile of the interfacing surface may be an area (such as with a ball and socket configuration), a line (such as with a roller or sleeve bearing), or a point (such as with a ball bearing).

The materials used for different embodiments of the invention will depend to some extent upon the type of surface contact being used as well as the type and extent of wear that may result. Examples of materials that may be used include, but are not limited to polyethylene (or other elastomeric material) on metal, metal on metal, or ceramic on ceramic.

The present invention also allows for customization of the instantaneous axis of rotation (JAR) and/or the center of rotation (COR) of one vertebral body with reference to another. The IAR and COR of a healthy vertebral body with respect to another is constantly changing in all planes because of pushing, pulling, and tethering of the segment through its range of motion by the ligaments, annulus, muscles, facets and other portions of the spine. Often, prosthetic disc replacement designs fail to mimic this varying TAR and COR. For example, a fixed ball and socket has a fixed IAR and COR. One potentially adverse result from using a prosthetic disc having a constrained implant is that the device may cause damage to facet joints due to anatomical interferences that may occur with a fixed axis of rotation. On the other hand, in general constrained JAR systems have been more stable than past designs utilizing a moving JAR. One example of a prosthetic disc having a fixed JAR is described in U.S. Pat. No. 5,314,477.

Conversely, past devices utilizing a moving IAR have provided the advantage of allowing for shear translation and of at least partially mimicking of the moving TAR of a healthy spine. These advantages, however, typically have been achieved in the past at the expense of a loss of stability of the device. Some examples of prosthetic disc designs having a moving IAR are described in U.S. Pat. Nos. 4,759,766, 5,401, 269, and 6,414,551.

In contrast, the present invention allows for an implant design that can mimic or partially mimic this varying IAR and COR to the extent desired by a physician while also preserving stability of the device. For example, one embodiment of the invention is a prosthetic disc that provides a moving IAR substantially in the sagittal plane so that a patient can more easily flex and extent the spine while limiting the movement of the IAR under lateral bending. It is believed that this configuration provides the best of both worlds by allowing a moving IAR for the predominant or more common motion a patient may undertake in day-to-day life while limiting lateral bending to achieve greater stability to the device. Several embodiments of the invention permit translation of one vertebral body with respect to another. By allowing one of these members to translate in the transverse plane results in the IAR and COR also translating in the transverse plane. As explained further below, one additional way of achieving a varying IAR and/or COR in three dimensional spaces is by combining two articulating surfaces opposing one another.

The interfacing surfaces of articulating and non-articulating embodiments of the present invention also allow for varying degrees of rotational and linear translation, and several embodiments of the present invention likewise permit a similar range of rotation and linear translation. Rotational translation is the movement of the intervertebral segment as a result of movement such as flexion, extension, and lateral bending. There are two components in this translation: one in the cranial/caudal direction and one in the transverse plane. Linear translation is translation in the transverse plane as a result of shear forces applied to the intervertebral segment. Thus, a ball and socket mechanism fixed in one location relative to the intervertebral segment would allow only rotational translation but would not permit linear translation. As illustrated in many of the embodiments that follow, however, linear translation of a ball and socket configuration could be achieved if the ball and socket were able to move in the transverse plane.

Endplates are used to associate the prosthetic disc with the vertebral bodies neighboring the disc. The endplates may be configured in several ways to help ensure a desired endplate-bone interface. For instance, the endplates may have one or more keels that extends into the bony portion of the vertebral body. Over time, bony ingrowths will surround the endplate and further help secure the endplate to the vertebral body.

In addition to keels, the endplate may have other or additional geometry that helps securely hold the endplate in place. For example, the end plate may have one or more teeth, rails, ribs, flanges, or other configurations that can help provide a surface that can secure the endplate more readily to the bone. Other short-term fixation may include screws or other fasteners that hold the end plate to the vertebral body. In some embodiments, these fasteners may be removed once a more long-term interface has been established, or alternatively the fasteners may remain in place indefinitely or until the prosthetic disc needs adjustment and/or replacement.

In addition to providing an endplate surface geometry or configuration that may promote bony ingrowths to hold the interfacing surfaces together securely over the long term, these configurations also may help provide short term fixation of the endplate to the vertebral body. For example, a keel may have a wedge shape so that the width of a first end of the keel near the endplate is narrower than the width of the distal end. Once installed, the inverted wedge of the keel helps prevent separation of the endplate from the vertebral body at least until bony ingrowths can more securely hold the endplate in place.

To help accelerate and to further promote bony ingrowths at the interface between the vertebral body and the end plate, the end plate may be coated with an osteoconductive material and/or have a porous or macrotexture surface. For example, the end plate may be treated with a coating that promotes bone growth. Examples of such coatings include, without limitation, hydroxyl appetite coatings, titanium plasma sprays, sintered beads, or titanium porous coatings.

Figure IA is a side view of a posterior prosthetic spinal disc I located between sequentially aligned vertebral bodies 2 and 3, such as are found in the cervical, thoracic and lumbar spine. Posterior prosthetic spinal disc I conforms in size and shape with the spinal disc that it replaces and restores disc height and the natural curvature of the spine. Posterior prosthetic spinal disc I comprises two opposite end plate 5 and 7 which are disposed in two substantially parallel horizontal planes when it is at rest, i.e., when it is not subjected to any load, either moderate or heavy.

The outer faces of end plates 5 and 7 are in direct contact with vertebral bodies 2 and 3 and may be textured or have a plurality of teeth to ensure sufficient contact and anchoring to the vertebral bodies 2 and 3. The outer faces of end plates 5 and 7 may also have a porous or macrotexture surface that facilitates bone ingrowth so that the posterior prosthetic spinal disc I is firmly affixed to vertebral bodies 2 and 3. Attached to the inner faces of end plates 5 and 7 are seating members 9 and 11 and a core 13 is securely placed between seating members 9 and 11. A stop member 15 is formed around the equator of the core 13, which functions to limit the motion of vertebral bodies 2 and 3 beyond a predetermined limit that is deemed unsafe to the patient.

As shown in Figure IA, the stop member may be formed from a ridge of material found on the core 13. As the end plates move relative to the core in response to movement of the spine, the stop member may approach or engage with one or both of the end plates to restrict further motion in a particular direction. The stop member may be formed of a relatively rigid material so that additional motion is substantially prevented once engaged against an end plate. Alternatively, the stop material may be made of resilient material that provides some cushioning or flex from deformation of the stop material before the range of motion is fully limited.

While the stop member is shown in Figure IA as being on the core 13, it also may be disposed on one or more of the end plates. For instance, the end plates may be configured with raised areas or ridges on its perimeter that engage with either the core or the opposing end plate in order to limit further motion in a particular direction. As mentioned above, the stop member on the end plate may limit motion to a greater degree in one direction than in another. Thus, the stop member may have various shapes and thicknesses to provide a variable range in motion that favors or disfavors movement in particular planes. For example, the stop member may have increased thickness on the side portion of the core to provide a more limited range of lateral motion of the spine while still allowing motion in the posterior/anterior direction.

The motion segment comprises a posterior prosthetic spinal disc 1 and adjacent upper and lower vertebral bodies 2 and 3. The exact contours of the core 13, seating members 9 and 11 and stop member 15 determine the range of motion allowed in flexion and extension, side bending, shear and rotation.

FIG. 1B is a top view of a posterior prosthetic spinal disc 1, showing the top end plate 5 and top seating member 9. The end plates may have various shapes that accommodate posterior insertion which avoids contact with the spinal cord. As shown in FIG. 1B, end plates 5 and 7 may have a substantially irregular elliptical shape or curved convex portion that resembles a kidney-shape. FIG. 2A is a top view of a posterior prosthetic spinal disc 1 being inserted between sequential vertebral bones. The posterior prosthetic spinal disc I is guided in place with a first implant holder 17 via an angled posterior approach that ensures that contact with the spinal cord 19 is avoided. The posterior prosthetic spinal disc 1 is generally oriented in line with the longitudinal axis of the first implant holder 17. Once the posterior prosthetic spinal disc 1 safely is maneuvered past the spinal cord 19 and in the desired position over the vertebral body 21, the implant may be turned or rotated, such as from 60° to 120°, so that it is oriented at about 90° to the first implant holder 17, as shown in FIG. 2B. Reorienting the implant may be accomplished in many ways. For example, FIG. 2B shows that a second implant holder 23 may be attached on the contra lateral side of the spinal cord to reposition and distract the implant into its final implanted position. Once the posterior prosthetic spinal disc I is in place, the first implant holder 17 and the second implant holder 23 is detached from posterior prosthetic spinal disc 1.

It is preferred that the posterior prosthetic spinal disc 1 closely mimics the mechanical functioning and the various physical attributes of the natural spinal disc that it replaces. In some instances, however, the prosthetic spinal disc may permit a more limited range of motion in one or more directions in order to prevent further spinal injury. In general, the prosthetic spinal disc can help maintain the proper intervertebral spacing, allow for proper range of motion, and provide greater stability. It can also help transmit physiological stress more accurately.

End plates 5 and 7, seating members 9 and 11, core 13 and stop 15 may be composed of a variety of biocompatible materials, including metals, ceramic materials and polymers. Such materials include, but are not limited to, aluminum, alloys, and polyethylene. The outer surfaces of the end plates 5 and 7 may also contain a plurality of teeth, maybe coated with an osteoconductive material, antibiotics or other medicament, or may have a porous or macrotexture surface to help rigidly attach the end plates to the vertebral bodies by promoting the formation of new bony ingrowth. Such materials and features may be used in any of the posterior prosthetic spinal discs described herein.

FIG. 3 is a collapsed posterior prosthetic spinal disc 30 that can be opened via scissor action, in which top end plate 32 and bottom end plate 34 are rotated along a pivot point 36 so that the longitudinal axes of top end plate 32 and bottom end plate 34 are substantially perpendicular. Accordingly, the surface area of the posterior prosthetic spinal disc 30 is increased to facilitate greater spinal support. The posterior prosthetic spinal disc 30 in collapsed form is sufficiently small enough to allow for posterior insertion while avoiding contact with the spinal cord.

FIGS. 4A-B illustrate a posterior prosthetic spinal disc having two segments for each end plate. The segments may be inserted separately between vertebral bones and assembled or joined together. The first segment 40 is inserted between the vertebral bones while avoiding contact with spinal cord 19. The second segment 42 is subsequently inserted between the vertebral bones while avoiding contact with spinal cord 19, and assembled or joined with first segment 40, forming an end plate having larger surface area. The first and second segments may be joined in any suitable manner to form an end plate. In one embodiment, the first segment has one or more protrusions and/or ridges that correspond to depressions, notches, or teeth in the second segment. The joining of the protruding regions of the first segment into the depressions of the second helps secure the two segments together. The same procedure is carried out for the second end plate. The size of the assembled end plates may otherwise be too large to insert between vertebral bones while avoiding contact with spinal cord 19.

Figure 5A:
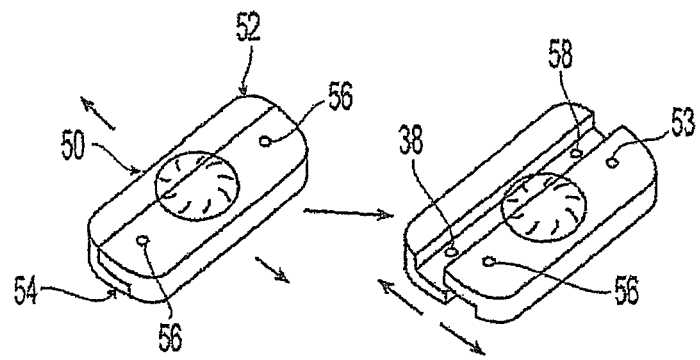
FIGS. 5A-5D depict various expandable posterior prosthetic spinal discs.

FIG. 5A is an expandable posterior spinal disc 50 that comprises expandable end plates 52 and 54 that can slide open or expand to increase the perimeter or contact area of the end plate with the vertebral body onto which it resides. In its collapsed state, the expandable end plate 52 is small enough to insert between vertebral bodies while avoiding contact with the spinal cord. In its expanded state, the expandable posterior spinal disc 50 has a larger surface area on upper and lower surfaces 52 and 54, which increases the contact area between the expandable posterior spinal disc 50 and the vertebral bones, or at least distributes loading over a greater surface of the vertebral bodies.

The expandable end plate may be formed of two or more segments that provide a low profile when in a collapsed state in order to facilitate a posterior approach during insertion. Once it is positioned over the vertebral body, however, it maybe expanded to increase the surface area of the end plate. The increased surface area helps provide greater stability of the end plate. Expansion of the end plate may be accomplished in several ways. In one embodiment, shown in FIG. 5A, a first segment and second segment may be selectively expanded or slid open along a substantially linear edge or surface. Thus, when fully extended the end plate will have a substantially linear slot defined by the edges of the first and second segment edges.

Figure 5B:
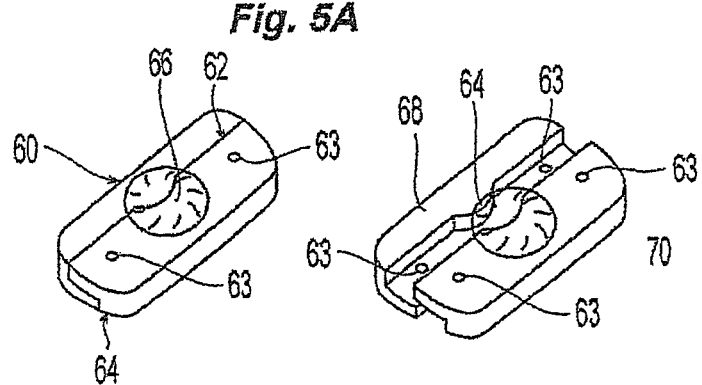

Alternatively, a portion of the edge of the first and second segments may be curved or rounded as shown in FIG. 5B. In this embodiment, the first and second segments may provide more balanced peripheral support of the core along its edges or sides. For instance, a curved or rounded portion of the first and second segments may help form a lip 66 that provides extended support of the core on one side than may be achieved from a linear slot. This configuration may help avoid cantilever loading of the core over the slot or opening between the edges of the first and second segments. In other words, lip 66 helps ensure that the connecting portion of the end plate 68 provided more evenly distributed support to the seat member 70.

Figure 5C:
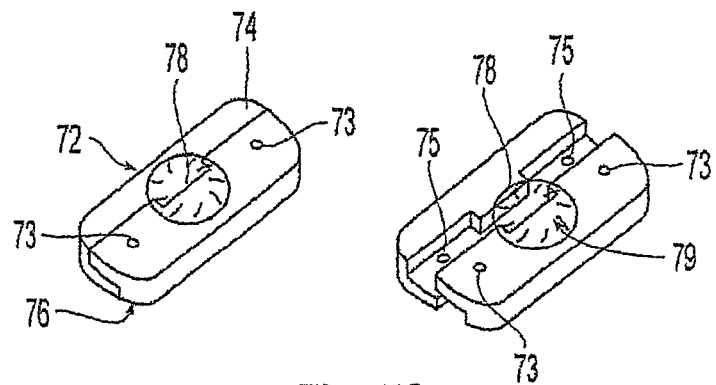
Figure 5D:
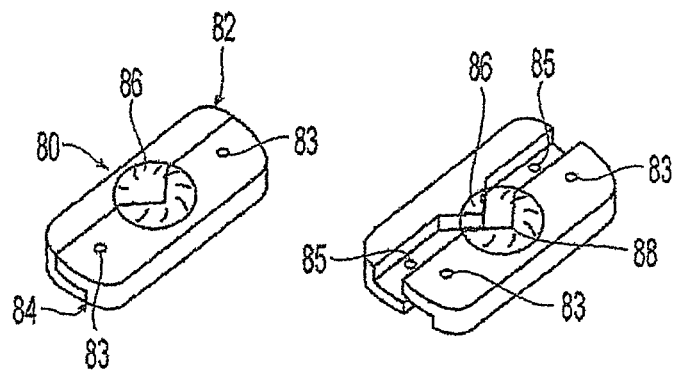

The additional lip of expandable posterior spinal discs can have other shapes, preferably being configured to reduce or minimize the occurrence of cantilever loads. For example, FIG. 5C shows an expandable posterior spinal disc 72 that comprises expandable end plates 74 and 76 that can expand along the latitudinal axis and comprises an additional lip 78 having a rectangular shape on end plate 74 and/or end plate 76. In another example, FIG. 5D shows an expandable posterior spinal disc 80 that comprises expandable end plates 82 and 84 that can expand along the latitudinal axis and comprises an additional lip 86 having a triangular shape on end plate 82 and/or end plate 84. Additionally, a posterior spinal disc may comprise expandable end plates that can expand along the latitudinal axis and comprise an additional lip having a convex curve. In both FIG. 5C and FIG. 5D, additional lips 78 and 86 have sufficient overlap with seating members 79 and 88 respectively that facilitates reduction of cantilever loads.

Figures 6A, 6B:
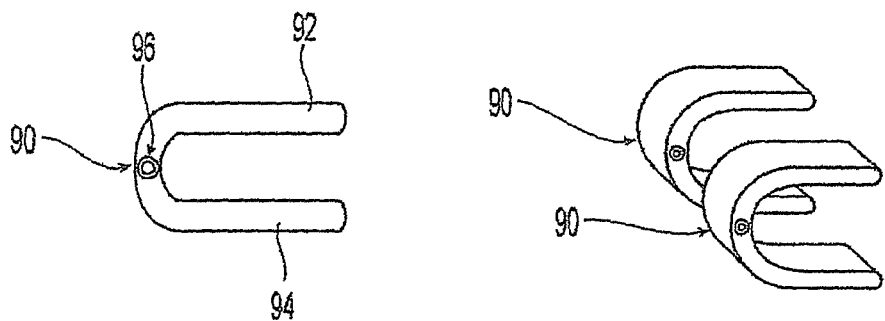
FIGS. 6A-B show open-sided or C-shaped disc implants having a spring.

FIGS. 6A-B illustrate a non-articulating posterior prosthetic spinal disc 90 comprising a top end plate 92 and a bottom end plate 94 that are joined together at one end to form a C-shaped disc. A spring 96 is located where top end plate 92 and bottom end plate 94 meet or are joined at one end of each plate 92 and 94 and allow for flexible motion of vertebral bones. The spring can be modified to have various tensions depending on the desired range of motion. The portion that joins the top end plate 92 and bottom end plate 94 also may be flexible itself and, in conjunction with spring 96, facilitates motion of the end plates 92 and 94. FIG. 6B shows two separate non articulating posterior prosthetic spinal discs 90, both of which can be inserted between the same two vertebral bones. The small size of non-articulating posterior prosthetic spinal discs 90 allows for easy insertion while avoiding contact with the spinal cord, and further provides greater freedom of motion because each non-articulating posterior prosthetic spinal disc 90 functions independently of one another. In general, the non articulating posterior prosthetic spinal discs encompassed by the invention have a C-shaped design, where openings, slots or springs create flexibility in the material to allow motion.

Figure 7A:
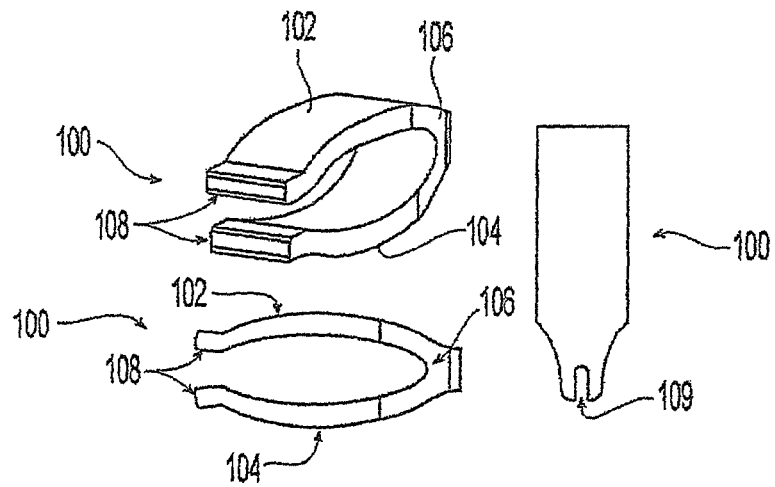
FIGS. 7A-B show open-sided or C-shaped discs having a flexible portion, curved end plates and stops.

FIG. 7A shows a C-shaped disc 100 having convexly curved end plates 102 and 104, flexible portion 106, and stops 108. The outer surface of end plates 102 and 104 may contain a plurality of teeth, may be coated with an osteoconductive material, antibiotic, or other medicament, or may have a porous or macrotexture surface to rigidly attach the C-shaped disc to the vertebral bodies and promote formation of new bone. The flexible portion 106 is tapered and the amount of taper controls the flexibility of the C-shaped disc. For example, increasing the amount of taper increases the flexibility of the C-shaped disc. Flexibility may further be controlled by providing a slot 109 located at the flexible portion 106. The slot may be cut in any shape and oriented in any manner within the flexible portion. The size of the slot may be varied to fine tune flexibility. For example, larger slot sizes provide flexibility of C-shaped discs. In another embodiment, more than one slot may be provided to increase flexibility. The stops 108 are located at the end opposite of the flexible portion 106 and limit the motion of the C-shaped disc 100. The size of the stops 108, as well as the amount of curvature of end plates 102 and 104 may be varied to control the range of motion of the end plates before the stops 108 touch. Once the stops 108 touch under moderate loads, the curved end plates 102 and 104 provide another range of motion under heavy loads that flatten and decrease the curvature of end plates 102 and 104.

Figure 7B:

FIG. 7B shows a C-shaped disc having stops 110 that are convexly curved to provide lateral flexibility. Once the stops 110 touch under moderate load, the curved surface allows the stops 110 to roll in order to facilitate some lateral spinal movement. The curvature of the stops can be varied to provide more or less lateral flexibility. In one embodiment, both stops 110 may be curved. In another embodiment, one stop may be curved while the other stop may be flat, convex, or have a different curvature. The stops also can have other surface shapes that allow for lateral flexibility, such as angled edges. In addition, slots may be formed on the lateral sides of the flexible portion to facilitate movement of end plates 102 and 104 in the lateral plane. The stops also may be curved or shaped to allow a greater degree of lateral movement in one direction than in another.

Figure 8A:
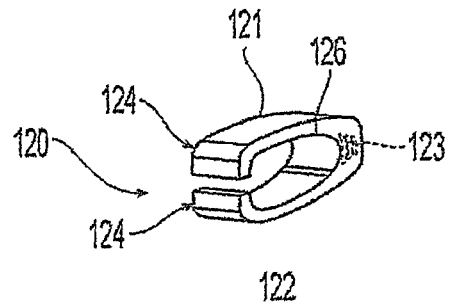
FIGS. 8A-B show open-sided or C-shaped discs having slots that provide flexibility.
Figure 8B:
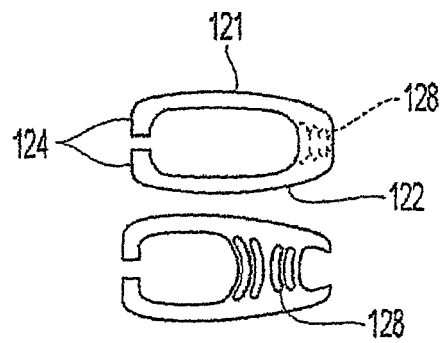

FIG. 8A shows a C-shaped disc 120 having end plates 121 and 122, stops 124, and a flexible portion having an opening 126 and slots 128. Stops 124 are located at the end opposite of the flexible portion and limit the motion of the C-shaped disc 120. The size of the stops 124, as well as the amount of curvature of end plates 121 and 122 may be varied to control the range of motion of the end plates before stops 124 touch. Once stops 124 touch under moderate loads, the curved end plates 121 and 122 provide another range of motion under heavy loads that flatten and decrease the curvature of end plates 121 and 122. The flexible portion contains slots 128 running through the lateral axis and can have any shape. The flexible portion also contains an opening 126 that is bored out along the longitudinal axis and helps provide flexibility. The number of slots, the size and shape of the slots, and the size and shape of the opening enable fine tuning of flexibility, where, for example, increasing the number of slots, as well as increasing the size of the slots or opening, provides for greater flexibility. In one embodiment, the flexible portion may be located closer to the middle of the disc, forming a skewed H-shaped disc, such as illustrated in FIG. 8B. The H-shaped disc allows for greater flexibility in the anterior and posterior directions. The outer surface of end plates 121 and 122 may contain a plurality of teeth or be coated with an osteoconductive material, have a porous or macrotexture surface to rigidly attach the C-shaped disc to the vertebral bodies, as well as to promote formation of new bone.

Figure 9:
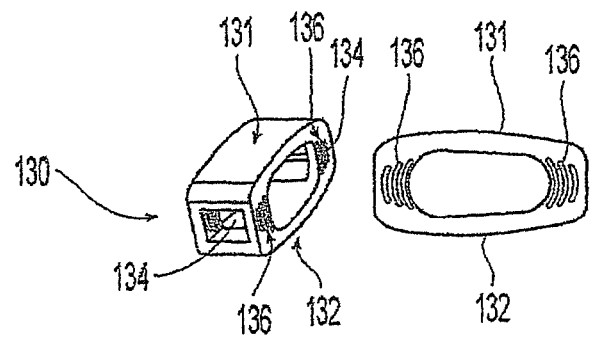
FIG. 9 shows a flat, generally rectangular or O-shaped disc having two slotted side columns.

FIG. 9 shows a generally oval-shaped or O-shaped disc having end plates 131 and 132 and two flexible portions joining end plates 131 and 132 at the longitudinal ends. Each flexible portion contains slots 136 running through the lateral axis and can have any shape. Each flexible portion also contains an opening 134 that is bored out along the longitudinal axis and helps provide flexibility. The number of slots, the size and shape of the slots, and the size and shape of the opening enable fine tuning of flexibility, where, for example, increasing the number of slots, as well as increasing the size of the slots or opening, provides greater flexibility. Each flexible portion may have the same or different configuration of slot shapes, numbers and sizes, positioning, as well as size and shape of the opening. The flexible portions can also be placed near the midline of the disc. In addition, the end plates can have convex curvature such that at heavy loads, the O-disc can flex by decreasing the curvature of end plates 131 and 132. The amount of curvature can be varied to provide different flexibilities. The outer surface of end plates 131 and 132 may contain a plurality of teeth or be coated with an osteoconductive material, have a porous or macrotexture surface to rigidly attach the C-shaped disc to the vertebral bodies, as well as to promote formation of new bone.

Figure 10:
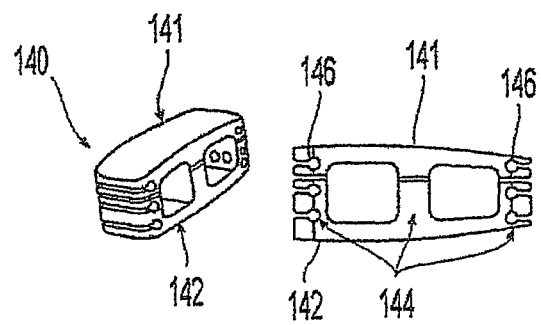
FIG. 10 shows a flat, generally rectangular or O-shaped disc having an additional column in the center portion of the disc and slots in the outer columns.

FIG. 10 shows a relatively flat double oval or O-shaped disc having an additional column in the center portion of the disc and slots in the outer columns. The disc has end plates 141 and 142, and columns 144 having slots 146 that provide flexibility. With the additional column in the center of the disc, end plates 141 and 142 will have a lesser degree of flex when compared to the O-disc described in FIG. 9. Such a configuration is desirable in applications where a more rigid disc is required. The slots 146 may any shape, size or positioning and as shown, slots 146 are rectangular notches having a cylindrical hole formed at the inside end of each notch. The outer surface of end plates 141 and 142 may contain a plurality of teeth or be coated with an osteoconductive material, have a porous or macrotexture surface to rigidly attach the C-shaped disc to the vertebral bodies, as well as to promote formation of new bone.

As shown in FIG. 10, the central column may have a gap or opening where the lower portion of the column terminates below the terminus of the upper column. This gap, which in one embodiment can be from about 0.5 mm to about 5 mm, allows the end plates 141 and 142 to have some ability to flex initially until the upper and lower columns meet to prevent further compression. In another embodiment, one or more columns may be formed from a highly resilient material that can provide some limited motion followed by cushioning that increasingly resists further displacement as loading on the prosthetic disc increases.

Figure 11:
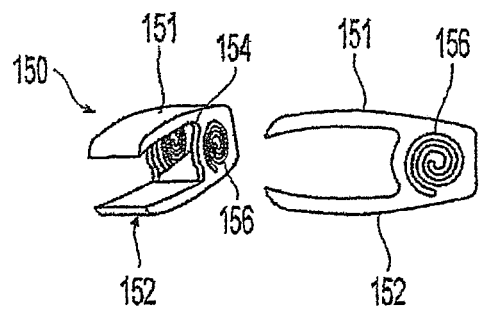
FIG. 11 is an open-sided or C-shaped disc having a coil slot.
Figure 25:
Figure 26:
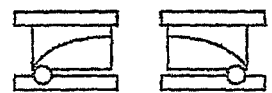

FIG. 11 illustrates another embodiment of the present invention where a C-shaped disc has two end plates 151 and 152, the posterior ends of which are connected by a flexible portion, and the flexible portion, and the flexible portion contains a coil slot 156 and an opening 154 that is formed along the longitudinal axis of the disc. The coil slot 156 and opening 154 provide flexibility and can be controlled by varying the size of the coil slot, number of spirals in the coil slot, as well as the size and shape of the opening 154. The outer surface of end plates 151 and 152 may contain a plurality of teeth or be coated with an osteoconductive material, have a porous or macrotexture surface to rigidly attach the C-shaped disc to the vertebral bodies, as well as to promote formation of new bone. Thus, the end plates and flexible portion may be integrally formed from one material.

In another embodiment of the invention, illustrated in FIGS. 12-14, utilizes a combination of tensioned and compressed elements disposed between the upper and lower end plates. The tensioned and compressed elements may be springs, as shown in FIG. 13, or may be made of resilient material that provides suitable resistance to stretching or compression. The compression element helps support axial loading along the treated vertebral bodies so that their relative positions approximate a healthy vertebral body supported by a natural disc. Additionally, at least one tension element helps provide controlled bending or movement of the vertebral bodies relative to each other.

The tensioned or compressed elements may likewise be configured and adapted to allow for compression and translation as shown in FIG. 12. Referring to FIGS. 13 and 14, the compression element can be pivotally connected to the upper and lower end plates, thereby allowing translation of the end plates in at least one direction by rotating the compressed element about the pivots. FIG. 14 shows that additional translation can also be provided in a second direction by configuring the pivoting connection such that the compressed element may slide along a rod or bar connected to one or more of end plates. As shown in FIG. 13, the first and second direction of translation can be generally orthogonal to each other. In this manner, a limited degree of translation permitted in any direction can be accomplished without affecting the range of translational motion in the second direction.

FIGS. 15-20 illustrate another embodiment of the invention including two or more implants that complement each other to form an arced or curved surface in the medial-lateral direction and in the anterior-posterior direction. Figure IS illustrates the curvature created in the medial-lateral direction, while FIG. 16 shows the curvature created in the anterior-posterior direction. As shown in FIGS. 17 and 18, the complementary curved surfaces of the upper and lower portions of the implants allows the upper vertebral body to move relative to the lower vertebral body while also maintaining a distance between the bodies that approximates the height of a natural disc. In one embodiment it is preferred that the curvature of the implant components is spherical so that they cooperate and function similarly to a ball and socket.

The implants may be space close together or far apart according to factors such as the size of the vertebral bodies, the loading that the implants will undergo, and the range of motion desired. As the implants are moved either closer together or farther apart, however, the curvature of the sliding surfaces may be changed. For instance, in the embodiment shown in FIG. 18, the curvature of the upper and lower portions of the implants in the lateral-medial direction is based on a radius R1 or R2. For implants separated further apart, the radius R2 is larger to account for the increased space between the implants. Changing the radius R according to the spacing between the implants helps maintain a relatively uniform radius of curvature across the full length of the implants.

Referring to FIGS. 19 and 20, which are similar in orientation to FIGS. 15 and 16, the upper and/or lower portions of the implants may have stops to help limit motion in one or more directions. As shown in FIG. 19, for example, medial-lateral movement can be controlled or limited by including a stop on one or more sides of an upper or lower portion of the implant. As the stop engages with the opposing surface of the implant, further movement in that direction is restricted. Alternatively, a resilient material may be disposed between the stop and the opposing surface in order to provide cushioning and to allow resistance to further movement to increase progressively. FIG. 20 illustrates that stops may be similarly used on one or more sides of the implant to limit the range of motion in the anterior-posterior direction. While the stops in FIGS. 19 and 20 are illustrated protruding upwards or downwards, other configurations also may be used to create a stop or to limit motion. For instance, the sliding surface of the portions of the implants may be prevented from further movement simply by contacting the end plate of the opposing portion.

FIGS. 21-26 illustrate one embodiment of the invention where different surfaces of the prosthetic disc provide for different types of movement. For instance, upper portion indicated as B in FIG. 22 may be configured so that the interfacing surface permits only lateral bending, while the lower portion A may have an interfacing surface that is a ball or rail having a radius that can translate for axial rotation.

Normally, during lateral bending the space between one side of neighboring vertebral bodies becomes larger while the space between the opposite side of the neighboring vertebral bodies gets smaller. One embodiment of the present invention helps mimic this characteristic of lateral bending by using a plurality of implants with upper and lower portions separated by oblong inserts.

Figure 27:
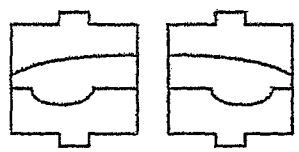
FIGS. 27-29 illustrate one embodiment of the invention using oblong inserts.
Figure 28:

As shown in FIG. 28, the oblong inserts are configured within the upper and lower portions of the implants at an angle so that during bending one insert rotates to help raise one lateral side while the other insert rotates in the same direction to help lower the opposing lateral side. To accomplish this combination of rising and lower of opposing sides of the vertebral body during lateral bending, the oblong inserts are positioned such that the upper ends of the insert are further apart than the lower ends Preferably, the oblong inserts are positioned such that they are angled from abut 5° to about 20° from a vertical axis when the vertebral bodies are in a neutral position, i.e., under conditions when there is no lateral bending. More preferably, the oblong inserts are positioned such that the axis from the upper end to the lower end is from about 70 to about 130 off of a vertical axis when the vertebral bodies are in a neutral position. As shown in FIG. 27, the insert on the opposing side of the vertebral body is positioned at approximately the same angle, but at a mirror image of the first insert. In this manner, one side will become lower during lateral binding while the opposing side increases in height.

The amount of increase or decrease in height from rotation of the inserts during lateral bending can be controlled in part by the length of the inserts from the upper end to the lower end. Thus, a longer insert will permit a greater range of lifting or lowering than a shorter insert. In one embodiment, the length of the insert is from about 3 mm to about 15 mm. In another embodiment, the length of the insert is from about 5 mm to about 10 mm.

Figure 29:
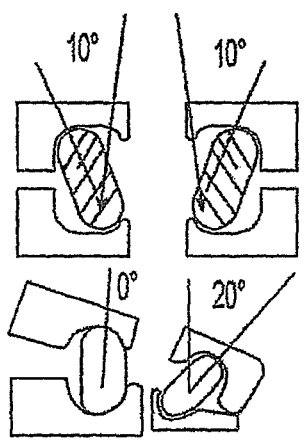

Additionally, the angle at which the inserts are initially positioned when the vertebral bodies are in a neutral position will also affect the degree to which there is a rise or fall in height from rotation of the inserts during lateral bending. For example, inserts that are angled only slightly off of a vertical axis will only be able to slightly raise or lower the height of the sides, whereas increasing the initial angle off of the vertical axis will allow more significant differences in height to occur. Thus, it is possible to control the degree of increase or decrease of height during lateral bending at least by either changing the length of the inserts or by changing the angle at which the inserts are positioned. For example, for the configuration shown in FIG. 29, the inserts may be positioned such that they are about 100 off of a vertical axis when the vertebral bodies are in a neutral position. In another embodiment, the angle may be from about 3° to about ISO.

Figure 30:
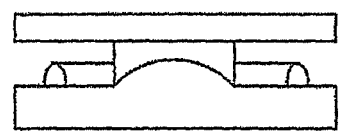

As discussed previously, the contacting surfaces of the upper and lower portions of an insert may be configured to have curved surfaces that allow varying degrees of lateral-medial movement or posterior-anterior movement. Stops also may be used to help further control or restrict movement. In addition to these features, stiffness mechanisms also may be used to provide greater resistance to movement. FIG. 30, for example, illustrates an upper and lower portion of an insert. A ring of elastomer is disposed in the space where the surfaces of the upper and lower insert meet. When compressed, the ring of elastomer adds non-linear resistance.

Figure 31:
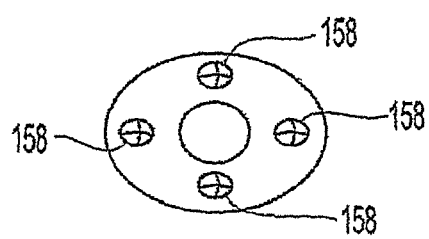
Figure 32:
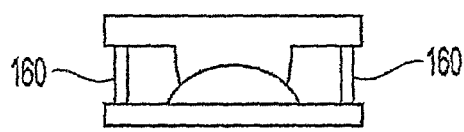
Figure 54:
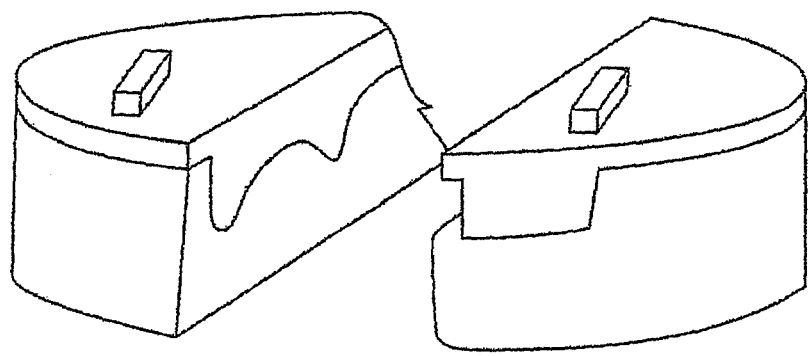
Figure 55A:
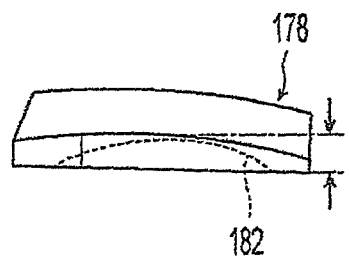
Figure 56:
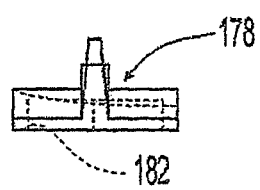
Figure 55B:
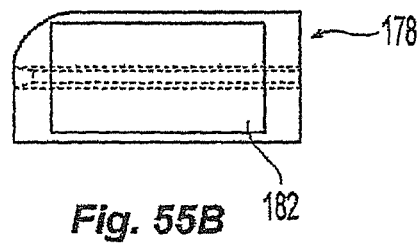
Figure 83A:
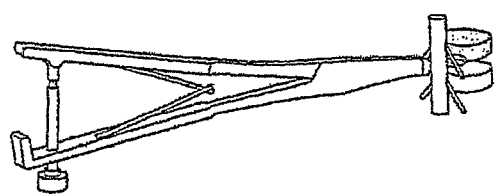
FIGS. 83A-B illustrate two optional methods for distracting the treated area during insertion of a prosthetic disc.
Figure 84A:
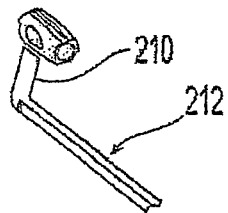
FIGS. 84A-B illustrate selective interaction between a free end of an angled guide and a keyed recess of a trial.
Figure 83B:
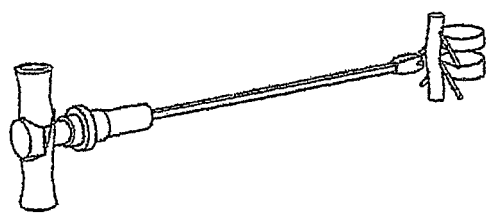
Figure 84B:
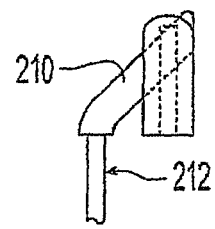
Figure 85A:
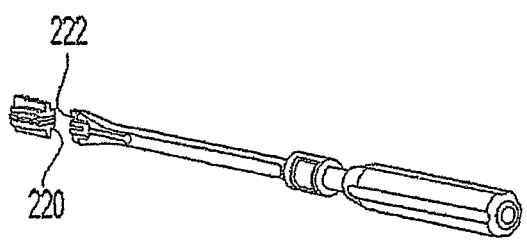
FIGS. 85A-B show one embodiment of a disc assembly holder selectively engaged with a disc assembly.
Figure 85B:
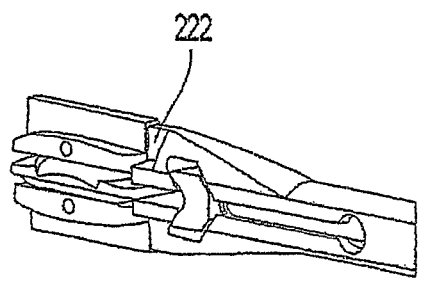

The use of elastomer to provide non-linear resistance to compression may be used in a wide variety of configurations in addition to a ring. In FIG. 31, for example, a plurality of elastomer protrusions or nubs 158 may be used to add stiffness or non-linear resistance to compression. Skilled artisans would likewise appreciate those other materials or structures may be used to increase resistance to compression. For example, one or more of elastomer nubs or protrusions in FIG. 31 may be replaced with springs. Further illustration of this embodiment is shown in FIG. 32, where springs and/or elastomer 160 can be placed in tension at various locations between the upper and lower portions of the insert.

Yet another variation of this embodiment is to use one or more flexible cantilevers to provide increased stiffness or resistance to compression. Referring to FIG. 33, one or more rods 162 may extend from one portion of an insert, i.e., an upper or lower portion, toward the surface of the opposing portion of the insert. In one embodiment, one end of each rod is fixed to a portion of the insert, but is not fixed to the other portion of the insert.

Thus, one end is fixed to one portion of the insert while the other end is free to move or bend in response to loading. The free end may be in contact with the surface of the opposing portion of the insert or alternatively may be preloaded by pressing it against the surface of the opposing portion of the insert. In another embodiment, the free end does not contact the surface of the opposing portion of the insert until a predetermined amount of movement of one portion relative to the other has already occurred.

Once the free end contacts the opposing surface, the bar or rod will begin to bend in response to additional movement. As the bar bends, the bending forces resist any further movement or compression, and as the movement in a particular direction increases, the resistance increases as well.

As shown in FIG. 33, the free end may be curved, bent, or otherwise shaped to prevent or minimize wear of the surface of the opposing portion. The flexibility of each cantilever rod may be altered or adjusted to allow greater or more rapid resistance to motion in one direction than in another. For instance, cantilever rods placed to resist lateral bending may be more flexible or less resistant to movement than a cantilever rod used to resist anterior-posterior movement.

Cantilever rods also may be used to provide controlled resistance to rotational movement of the vertebral bodies. FIG. 34 shows a top view of an insert having this embodiment of the invention. Mechanical stops may be disposed near the free ends of the cantilever rods so that once rotation increases beyond a certain point the free end engages with one of the stops and causes the cantilever bar to bend or resist further rotational movement. The torsional resistance created from the stops increases as rotation continues.

Another embodiment of the invention utilizes a flexible rod or shape memory metal rod near the center of the insert to provide a stop or to generate progressive resistance to flexing, extension, lateral bending, or rotation. One example of this embodiment is shown in FIG. 35, which illustrates a rod connected to a lower portion of an insert and extending upwards into a cavity of the upper portion of the insert. As with any of the embodiments described herein, the upper and lower portions of the insert may be configured to have a ball and socket configuration or a simple radius protruding portion and corresponding simple radius receiving portion, thereby permitting lateral medial movement, anterior-posterior movement, and rotational movement.

As the upper portion 164 of the insert moves relative to the lower portion 166, the cavity wall eventually will contact the free end of the rod. If the rod is very stiff, contact with the cavity wall will stop further movement. In contrast, if the rod is flexible, it may bend in response to contact with the cavity wall, thereby providing progressive resistance to further movement in that direction.

The cross-sectional profile of the cantilever rods described herein may be any shape, and are not limited to circular cross-sections. For instance, the cantilever bars may have a generally rectangular cross-section, such as in FIGS. 37A-C, so that it is more resilient to bending loads in one direction than in another.

Different cross-sectional shapes also may be used to provide resistance to rotational movement in the embodiment illustrated in FIG. 35. For instance, if the cantilever rod has a rectangular cross-section as illustrated in FIGS. 37A-C, and extends into a non-circular cavity, rotational movement can cause the free end of the cantilever to contact the cavity wall. Once again, the stiffness of the cantilever can be varied to either prevent further rotation beyond a certain point (i.e., the cantilever acts as a full stop to further rotation), or the cantilever can flex or twist to provide progressively increasing resistance to further rotation.

In an alternative embodiment (as depicted in FIG. 36A-B), two or more rods may be disposed within the central portion at spaced apart locations so that rotation causes the plurality of rods to bend and impart torsional resistance to further rotation. FIG. 38 illustrates another socket and ball compression mechanism according to the invention. The hinges may be placed at A to allow the socket and ball to "float". Under compressive axial loading of the spine, torsion bars 168 may bend or flex to cushion the spine.

FIGS. 39-41 show a non-articulating insert according to the invention having two endplates attached to springs, preferably at least 2 or more independent springs. The springs allow for motion (translation), compression, and a combination of both (flexion/extension and lateral bending). As illustrated in FIG. 42A (showing an axial view of the spine), a single insert may be used with posterior or posterior lateral implantation. In addition, two or more inserts may be used, jointly or independently of each other. For example, FIGS. 42B-C shows two inserts, which may be oriented generally in an anterior-posterior direction or in a medial-lateral direction, whereas FIG. 42D depicts three inserts. Multiple inserts may have the ability to attach to one another after implantation.

FIGS. 43-45 illustrate an insert where pivots 170 are added to the non-articulating insert of FIGS. 39-41. The pivots allow motion, whereas the springs act as shock absorbers and restore the implant to a neutral position. The endplates may have teeth, a textured surface, chemical treatment, or other means to secure the implant to the vertebral body.

A hollow braid 172 may also be used to make the insert of the invention. As shown in FIGS. 46-47, the braid may be reinforced with metal struts for strength and fixation. In addition, the insert may have a hollow pocket 174 filled with a balloon or a bladder of a gel, fluid, elastomer, gas, or other material to mimic the annulus or nucleus. The balloon may be filled with air or fluid and can have various shapes, e.g., cylindrical, oval, circular, etc.

The following three examples further illustrate how several of the features described above may be implemented in a prosthetic disc.

The first example, shown in FIGS. 48-49 and 50A-B, describes a prosthetic disc that may be designed to have an IAR that is either substantially fixed one location or alternatively may be configured to move in the axial plane. As shown in FIG. 49, a plurality of upper and lower portions may be inserted at spaced apart locations. Preferably, one upper and one lower portion forms an assembly that can be inserted at the same time. By forming, the disc from two assemblies as shown in the figures one assembly can be inserted on each side of the spinal cord, thereby greatly reducing the space needed in order to insert the disc. In this manner, many of the risks commonly associated with a posterior approach can be avoided or minimized.

As explained in detail below, the upper and lower portions may have segments that can be repositioned after the assembly has been positioned inside the patient in order to bring the interfacing surfaces of the upper and lower portions into their final position.

For example, the upper and/or lower portions may be configured with a movable segment that allows repositioning of the interfacing surface once the portion has been inserted into the patient's body. In this manner, the overall size of the assembly can be made more compact when inserting it into the body while also allowing the components of the assembly to be reconfigured once inside the body in order to achieve optimal positioning of the interfacing surfaces of the prosthetic disc. This, while FIG. 49 illustrates the final positioning of two assemblies after the segments have been repositioned, the segments initially may be inserted into the body in a low-profile configuration, such as illustrated in FIG. 50A, and then reconfigured to a second position, such as shown in Figure SOB, once in the treated area. The second position allows the implant to perform its intended function, while the first position provides a low-profile insertion of the assembly. As shown in FIG. 48, one way to allow repositioning of the segments is to provide a track on which the segments may slide.

The segments may be configured such that a first assembly may be inserted independently and then interlock with corresponding segments of a second assembly, as shown for example in FIG. 49. Alternatively, the segments may be configured such that even after repositioning they do not contact a corresponding segment. In any of these embodiments, a locking mechanism may be used to fix the position of the segment relative to the portion it is associated with in order to prevent unintended repositioning of the segment after the surgical procedure is completed. One example of such a locking mechanism is the use of a protrusion or detent.

To help minimize the profile of the assembly during insertion, one segment may be configured such that the assembly has a lower overall height during insertion than when all of the components of the assembly are in their final position within the patient. FIGS. 50A-B illustrate this feature of the invention. In particular, the segment associated with the upper portion of the assembly is configured such that it slides along the interfacing surface of the segment associated with the lower portion of the assembly. The upper portion may be configured with one or more tracks or channels that guide a corresponding number of protrusions or keels on the upper portion of the upper segment. Thus, the upper segment is able to rotate and slide down the surface of the lower segment in order to lower the height of the assembly during insertion. Once inside the body, however, the segment can be slid into its final position. As this occurs, the overall height of the assembly will be increased. In one embodiment, the overall height of the assembly may be increased from about 0.1 mm to about 3 mm, and in another, the distraction caused by repositioning the segment may be from about 0.5 mm to about 1.5 mm.

The second example of the present invention, illustrated in FIGS. 51 to 54, also uses two assemblies and is configured to have a fixed IAR. The upper and lower portions of the assembly may have interfacing surfaces that are substantially spherical in curvature and that have substantially the same radius of curvature so that the overall configuration of the sliding surfaces provides a surface contact over an area as opposed to a line or point. In this example, the assemblies of the upper and lower portions are not configured with slidable segments as described in the example above. Because the sliding surfaces in this example are substantially spherical in curvature, proper alignment of each portion of each assembly is important to achieve a desired surface contact over an area instead of a line or point.

The third example of the present invention is shown in FIGS. 55-61. This example uses two articulating surfaces in a three component assembly to provide a moving IAR in the anterior-posterior direction only. As described in the examples above, two assemblies may be used to provide a low profile during insertion. Each assembly is formed of three components: an upper portion 176, a lower portion I 78, and a central element 180 having upper and lower surfaces that interface with corresponding surfaces of the upper and lower portions. It should be understood that the orientation of the surfaces described below may be placed on an upper or lower component and that the invention is no restricted or limited to only the orientation described below. One interfacing surface is configured in a similar manner as provided in Example 2, above. That is, the interfacing surface is substantially spherical in curvature such that the surface contact is over an area instead of over a line or a point. FIGS. 58A-C illustrate the spherical surface interface 184 that may be disposed between the upper portion and the central element.

The second interfacing surface is formed of two cylindrical surfaces 182 that permit rotational sliding essentially in one direction (I.e., about one axis). As shown in FIGS. 57A-C, the lower surface of the central element has a generally cylindrical shape 182 protruding downward, while the lower portion has a corresponding cylindrical shaped groove 182 formed therein that receives the cylindrical shape of the central element. Preferably, the radii of curvature of both cylindrical shapes are approximately the same such that the surface contact is over an area instead of a line. In this manner, the cylindrical surfaces can be configured to permit bending while restricting rotation. Thus, during flexion or extension both interfacing surfaces permit movement, while only one interfacing surface may permit lateral bending or axial rotation.

In an alternative embodiment, however, a second cylindrical interfacing surface can be substituted for the spherical surface. This second cylindrical interfacing surface may be disposed orthogonally to the direction of the first cylindrical interfacing surface. In this manner, one surface will permit motion in one direction, such as flexion and extension, while the second will permit lateral bending.

FIGS. 59-61 illustrate the types of motion that may be achieved using a first interfacing surface that is generally spherical with a second interfacing surface that is generally cylindrical. FIG. 59 illustrates a disc disposed in a neutral position having a disc height H. During extension and flexion, the disc can provide rotational translation in the axial and in the anterior-posterior direction. Under these conditions, the overall height of the disc can change. Additionally, however, the disc also permits linear translation without changing the height of the disc. As shown in FIG. 61, the upper and lower portions can translate with respect to each other without also having to rotate.

As shown in FIGS. 62A-H, a pair of disc assemblies may be used to form a prosthetic disc of the present invention. One advantage of using multiple assemblies is that a posterior approach may be used to position them into a treated area. A plurality of disc assemblies having varying heights, widths, lengths, and ranges of translation and rotation capability may be provided in a kit to a physician so that the final selection of the proper disc assembly can be made during the surgical procedure. For instance, a plurality of disc assemblies may be provided having disc heights varying from about 10 mm to about 20 mm. In one embodiment, the disc heights may differ by a uniform increment, such as differing by about I mm or by about 1.5 mm within a range.

Likewise, the length of the disc assembly may be varied to accommodate different anatomies. For instance, disc assemblies may have longitudinal axes that range from about 20 mm to about 28 mm. Incremental changes in the length of the assemblies may also be provided in a kit, such as by providing disc assemblies of different lengths in 2 mm increments. In another embodiment, a plurality of assemblies may have at least 2 different lengths that differ by more than about 3 mm. For instance, one set of disc assemblies may have a length of about 22 mm, while another set is about 26 mm in length. The length of the disc assembly preferably may be selected to maximize implant/endplate contact area.

A plurality of assemblies may also be provided with differing ranges of axial rotation. For instance, one or more assemblies may have no restriction on rotational movement, or may have stops or other devices that prevent rotation only after the rotation has exceeded the range of motion of a natural, healthy spine. Some assemblies may limit a range of axial rotation to ±15°, ±10°, 5°, or ±2°.

Other disc assemblies of the present invention may permit a range of axial rotation in one direction, but restrict it in the opposite direction. In other words, a disc assembly of this embodiment may permit limited disc rotation so that a patient may rotate or turn their body to one side or in one direction, but not in the other. For example, a disc assembly may allow rotation or movement between a 0° position, where the spine is not rotated or turned, to up to about 5°, up to about 8°, up to about 10°, or up to about 15° in one direction only.

As described above, a cylindrical surface may be provided in a disc assembly in addition to a second, curved surface corresponding to a portion of a sphere. One feature of this combination of surfaces is that the disc can permit translation between the upper vertebral body and the lower vertebral body neighboring the treated area.

In one embodiment, the disc is capable of permitting translation of up to about 3.0 mm in the anterior-posterior direction, while in another embodiment the disc is capable of translation of up to about 5 mm. Some disc assemblies may permit even more translation, such as up to about 7 mm or even up to about 10 mm. As illustrated in FIGS. 62A-H and described in depth above, mechanical stops 186 may be provided to limit the range of motion of the disc assembly. FIG. 62C also illustrates that spacing of multiple assemblies may be important for providing a generally spherical surface, if one is desired. For instance, it may be desirable for the central longitudinal axes of the assemblies to be approximately 9-16 mm apart, and more preferably from 11-14 mm apart.

The upper and lower portions of a disc assembly may be configured with a keel 188 that can engage with or contact a neighboring vertebral body. One advantage of providing a keel is that it may be used to guide the assembly into position during insertion into a treated area of the spine. For instance, as illustrated in FIGS. 63A-B and 64-65, a channel or groove may be cut out of a vertebral body next to the treated area. Then, a physician may insert the assembly into the vertebral body so that the keel slides in the groove or channel. The keel and grove or channel may be substantially linear or straight, or alternatively, may be curved or arched so that the assembly rotates and slides into position.

The use of one or more keels may also increase bone to implant surface contact, thereby decreasing the likelihood that the assembly will shift or move about of position. In one embodiment, the increase in surface contact may be about 5% or more, which in another embodiment the increase may be about 15% or more.

The cross-sectional profile of the keel may have different shapes. For instance, the cross-sectional profile of the keel may have the shape of a wedge, a truncated wedge, a rectangle, or a square. As shown in FIG. 63A, the channel or groove may be cut to have a cross-sectional profile corresponding approximately to the shape of the keel. One advantage of the keel having a truncated wedge cross-section is that a similarly shaped channel or groove may ensure that the keel engages with the bony surface. This configuration may also provide increased resistance to expulsion of the disc assembly.

Over time, it is believe that the stability of the disc assembly in the treated area will further increase as bone growth engages with outer surfaces of the disc assembly. To facilitate this growth and increased stability, all or part of the surfaces of the disc assembly that engages or otherwise contacts bone may be treated to promote bony on growth. For instance, titanium plasma may be provided on the keel or other portions of the assembly to provide a matrix for bone growth. In addition, the keel may be configured with notches, slots, or openings formed along its length. As bone grows into these openings, the disc assembly will become more securely anchored in place.

As a disc assembly is first inserted into a treated area, it may need to be repositioned, rotated or otherwise moved. For instance, repositioning the disc assembly may be needed so that the keel can properly engage with the channel or groove. As shown in FIG. 62G, the leading edge Le of the disc assembly may be configured without a keel. Thus, in one embodiment the assembly can be partially inserted into the treated area without the keel engaging with or contacting the vertebral body. In one embodiment, the length of the leading edge is from about 1 mm to about 10 mm, while in another embodiment the leading edge is from about 2 mm to about 5 mm. Alternatively, the length of the leading edge may be from about 1% to about 20% of the length of the component on which it is disposed, or may be from about 2% to about 10%. The length of the component may be determined by measuring the longitudinal central axis of the portion or component on which the leading edge is disposed.

In addition, referring again to FIG. 62O, the keel may have an initial portion that is sloped or gradually increases in height. Providing a ramped portion may aid in aligning and inserting the keel into a groove or channel formed in a vertebral body.

The present invention also encompasses a method for implanting a posterior prosthetic spinal disc. In particular, the method comprises removing a defective vertebral disc using conventional methods and instruments; separating or distracting adjacent vertebral bodies to permit insertion of the posterior prosthetic spinal disc; inserting and positioning the posterior prosthetic spinal disc using a posterior or posterior lateral insertion that avoids contact with the spinal cord; and relieving the separation or distraction of the adjacent vertebral bodies.

As will be explained in detail below, there are several variations in which the present invention may be used to provide a replacement or prosthetic disc for a patient that restores or maintains a more natural range of motion. While a single disc assembly may be used to establish the artificial disc within a patient, it may be preferred in some cases to provide more than one artificial disc assembly. Vertebral bodies having larger sized endplates, for instance, may benefit from using two or more disc assemblies, or subassemblies to create an artificial disc in a treated area. For example, a disc assembly that is from about 9 mm wide may only need an insertion window that is from about 9 mm to about 11 mm of wide. In one embodiment, the insertion window needed to deploy a disc assembly is from about 7 mm to about 15 mm wide, and more preferably is from about 9 mm to about 12 mm wide.

Several benefits may be realized from using multiple disc assemblies. For instance, one result of using multiple assemblies may be that the smaller insertion windows may not require as significant motion or retraction of the aorta or vena cava. For example, in one embodiment, movement of the aorta in the present invention for inserting one of a plurality of disc assemblies is less than half the distance of repositioning that would be required if the prosthetic disc were made of a single, full size assembly. In addition, using multiple disc assemblies may allow a shorter duration of time during which the aorta, vena cava or other anatomy is moved out of its natural position. In one embodiment, for example, the duration of time that the aorta or vena cava is moved for inserting one or a plurality of disc assemblies is less than half of the duration of time normally required to insert a prosthetic disc made of only one assembly or unit. In addition, the smaller insertion windows that can be achieved from using multiple disc assemblies will likely make it easier to access the disc space from as well as allow for greater options in the approaches that may be used.

Furthermore, the use of multiple assemblies may reduce the frequency and/or the amount of retraction needed during insertion and positioning of the assemblies. For example, if two disc assemblies are used in a posterior approach, a central region of the treated area in the anterior-posterior direction may have sufficient space for placing a distractor. As a result, other benefits from this configuration may also be achieved. For instance, in many embodiments of the invention it may be useful to ensure that the prosthetic disc is positioned properly along the midline of the vertebral body in the anterior-posterior direction. By using a distractor in the central region of the treated area, the present invention may allow a physician to select a midline of the prosthetic disc with respect to the vertebral body, distract the vertebral bodies with the distractor in the central region, conduct an x-ray or other procedure to confirm that the selected midline of the prosthetic disc is approximately the same as the midline of the vertebral body, and make any desired adjustments of the distractor location before inserting a disc assembly. In one embodiment, the physician's selected location of the midline of the prosthetic disc differs from the midline of the vertebral body by less than about 3 mm, and more preferably differs by less than about 1 mm at any point along the length of the part of the distractor located between the vertebral bodies. If the difference between the selected location of the midline of the prosthetic disc and the confirmed midline of the vertebral body falls outside an acceptable tolerance, the physician may then reposition the distractor and either reconfirm its new position or continue with inserting the disc assemblies after the adjustment is made. Once the distractor is in an acceptable or desired position, the disc assemblies may then be placed within the treated areas. The distractor location may be used with or without other tools or devices to help ensure correct placement of the assemblies with respect to the anterior-posterior midline of the vertebral bodies.

A disc assembly may comprise tree component parts: an upper rigid plate, a lower rigid plate, and a central core or core element. The core element is disposed generally between seating surfaces of the upper and lower plates. The seating surfaces of each plate may be contoured to provide a desired range of motion. For example, one or more of the seating surfaces may have a substantially spherical curvature. In this manner, the seating surface may generally correspond to a portion of a ball or a socket. The central element may likewise have a contoured surface that generally has the same curvature as the seating surface it contacts. Thus, a spherical-shaped seating surface can receive or contact a portion of the central element having a spherical contour having a similar radius of curvature. The contact between the two surfaces may therefore correspond to a portion of a ball and socket.

Providing a spherical surface allows the two components to rotate and slide across the contacting surfaces in a manner that would permit bending and rotation ozone vertebral body relative to another. If these two contacting surfaces were the only elements allowing movement, the IAR of the disc would be constant. Providing a second contacting surface allows the disc to mimic a variable JAR of a healthy disc. For example, a second contacting surface between the second rigid plate and the central element may have a cylindrical contour, preferably allowing the core element to provide rotation in the anterior-posterior direction. Thus, it is preferred that the cylindrical surfaces of the second rigid plate and core element have an axis of rotation that extends approximately in a lateral direction.

The combination of a spherical shaped surface contact between one plate and a portion of the core element with a second generally cylindrical contacting surface between another plate and another portion of the core element allows the disc to have a variable JAR. This configuration also allows for translation ozone vertebral body relative to another vertebral body without requiring either vertebral body to rotate and without requiring the distance between the vertebral bodies to increase or decrease.

The curvature of the seating surfaces of the plates may be concave and the corresponding contoured portions of the core element may be convex to provide contact between the surfaces. Alternatively, one or more of the contoured surfaces of the core element may be concave and the seating surface for which it engages likewise may be inverted. For example, in one embodiment the core element may have a contoured convex surface that it semi-spherical or generally corresponds to a portion of a spherical surface, and a contoured concave surface that is semi-cylindrical or generally corresponds to a portion of a cylinder. One advantage of this configuration is that is may be capable of achieving a lower overall height than a core element having two convex contoured surfaces.

As described previously, more than one assembly may be used to form a disc. For example, a second assembly may be provided having a similar arrangement of plates and a core element. When disposed in a treated area, one or more components of an assembly may contact or even interlock with a corresponding component of another assembly. For instance, the seating surfaces of plates disposed on the bottom of two assemblies may be independently inserted into the treated region and subsequently joined. Conversely, the assemblies may be disposed at a predetermined distance from the other. For example, if two or more assemblies have contoured semi-spherical surfaces with a large radius of curvature, the assemblies may be separated by a predetermined distance so that the two contacting surfaces operate as component parts of a ball and socket configuration.

The configuration of the contacting surfaces of the disc may be varied depending upon the surgical approach used to insert the assembly. For instance, in one embodiment a facet capsule may be removed from one side of a vertebral body to provide access to the treated area from a transforaminal approach. The endplates of the vertebral bodies in the treated area may then be cut or otherwise prepared for receiving an assembly. Preferably, the bony anatomy of the vertebral body that defines the vertebral foramen still encloses this region after the removal of the facet capsule. Once the treated area is prepared, an assembly may be inserted. In addition to a posterior or transforaminal approach, other approaches can be used with the present invention, including, but not limited to posterior-lateral, lateral, or anterior approaches.

With a transforaminal approach, the direction or path in which the assembly is inserted may form an angle with an axis extending in the anterior-posterior direction. Because the approach to the treated area is at an angle, the seating surfaces may be configured to provide a desired functionality. For example, as described above, the assembly may have a cylindrical seating surface having an axis that extends generally in a lateral direction of the spine. Thus, the plates of the assembly may have a longitudinal axis that generally corresponds to the path in which the assembly is inserted, and the axis of rotation of the cylindrical contoured surface of the core element may form an angle from about 20° to about 70° of the longitudinal axis. More preferably, the angle between the longitudinal axis of the plate and the core element axis of rotation forms an angle from about 30° to about 60°.

When a facet capsule is removed, the rotational stability of the vertebral body may be compromised. Since anatomy that helps prevent excessive rotation of the vertebral body is removed, it may be beneficial to provide a mechanical stop that prevents rotation in the compromised direction. In one embodiment, the stop only permits rotation of less than 10 degrees in one direction, and more preferably prevents rotation greater than 7 degrees. In other embodiments, the stop only permits rotation from about 1 to about 7 degrees or from about 1 to about 5 degrees in one direction. If the facet capsule on the opposing side of the vertebral body is still intact, it may not be necessary to provide a mechanical stop for rotation in the opposite direction. In this manner, a rotational stop may be provided only when anatomy aiding in this functionality has been removed.

It is preferred that the contact between the seating surface of a plate and a contoured surface of a core element extends over an area rather than a line or a point. More preferably, all contact surfaces of the invention extend over an area. However, if a convex surface semi-spherical surface were formed with a smaller radius of curvature than the corresponding concave surface, it would be possible to have the contact between the two surfaces correspond to a point contact. Likewise, a convex cylindrical surface may be formed to be smaller than the concave cylindrical surface it engages with in order to form a contact surface corresponding to a line.

The plates also may be configured to engage more securely with the vertebral bodies that they contact. For instance, one or more raised ridges or keels may extend at least partially into the endplate of the vertebral body. The vertebral body likewise may be prepared by cutting a similar number of grooves or channels that will receive the keels. The grooves or channels may help guide the assembly into proper position in the treated area. This feature may be particularly beneficial when a certain orientation of the assembly relative to the vertebral body is desired.

The ridges or keels and corresponding channels or grooves also may be straight or curved to match the desired insertion path of the assembly. In one embodiment, the cross-section of a ridge or keel may be triangular or have a truncated triangular shape. As mentioned above, if more than one assembly is being used, it may be desirable for the assemblies to be separated by a predetermined distance. The grooves or channels formed in a vertebral body may help achieve the proper orientation and distance of the assemblies.

To date, no tool or device has been developed that can provide these features to ensure proper insertion of a multi-assembly artificial disc. As shown in FIGS. 63A-B and 64-65, a trial 190 may be used to accurately form channels or grooves at a predetermined distance. Turning to FIG. 64, a trial 190 may be used to aid in cutting upper and/or lower channels in facing endplates of two vertebral bodies. Additionally, the trial may smooth portions of the endplate surfaces where an assembly may travel or ultimately be disposed. The trial may be inserted in a direction that corresponds to the path that will be used to insert the assembly. As mentioned above, the insertion path of the assembly may not always correspond to anterior-posterior axis of the vertebral bodies. For instance, an angle formed between the direction of the insertion path for the assemblies and the anterior-posterior axis may be from about 20° to about 70°, or may be from about 30° to about 60°. The path also may form a circular arc having a radius of curvature corresponding to the curvature of the ridges or keels of the plates. In this manner, the assembly may be rotated or turned into its final position as it moves along the channels or grooves.

Once the first channel and groove or plurality of channels and grooves has been formed, a guide 192 may be used to determine where a second set of channels or grooves may be formed. In general, the guide 192 is in communication with and extends from the first trial 190. As shown in FIGS. 63B and 64-65, the guide 192 may be disposed within a central portion of the trial 190. Once the trial is in its proper position, the guide may then be deployed a predetermined distance. Turning to FIG. 65, a portion of the free end of the guide may have a configuration that can receive a second cutting tool 194. The second cutting tool 194 may then be used to form a second plurality of grooves or channels and to prepare a second region of the treated area to receive a second assembly. The guide 192 and trial 190 may then be removed and the assemblies inserted into the treated area.

The plates used to contact with the endplates of the upper or lower vertebral bodies of the treated area should have sufficient size to distribute loading over an area of the vertebral body to prevent failure of the endplates. Thus, one or more of the rigid plates may have a length from about 25 to about 32 mm, and more preferably from about 28 to about 30 mm. Likewise, the width of one or more plates may be from about 10 to about 18 mm, and more preferably is about 12 to abut 14 mm.

In another embodiment illustrated in FIGS. 66-67, a trial may be capable of connecting with a handle having a detachable grip. In one embodiment, the trial may have a chisel guide 196 and keyed recess 198. This tool, among others may be used to facilitate installation of one or more disc assemblies from a posterior approach in the following exemplary manner.

As shown in FIG. 68, a physician may first perform a discectomy in the treated area. In one embodiment, the discectomy is performed so that a perimeter region of the annulus is not removed. For instance, 1 mm to 7 mm, and more preferably 3 mm to 5 mm, wide region along the perimeter of the anterior side of the vertebral body may remain after the discectomy is completed.

When viewed from the posterior side, the spinal cord may obstruct the view of a central portion of the vertebral bodies thereby leaving two posterior sides of the vertebral body for inserting disc assemblies. If desired, a distractor may be used on the contralateral side while a trial is inserted on the other side. When a posterior approach is used, a preferred embodiment of the invention is to use 2 disc assemblies where one is placed in the treated area from one side of the spinal cord and the other is inserted from the other side.

In another embodiment, the trial itself may be used to distract the vertebral bodies. The physician may assess the treated area and select a suitable disc a suitable disc assembly from a plurality provided in a kit. Factors that may be considered when selecting a disc assembly may include, among others, the footprint of the disc assembly, lordosis, disc assembly height, and size.

As shown in FIG. 62C, if one or more sliding surfaces of the prosthetic disc is substantially spherical in curvature, it is desirable to position the disc assemblies a predetermined distance apart from each other and in proper alignment to allow portions of the 2 disc assemblies that form the sliding surface to cooperate. Providing a keel on each disc assembly may be useful for properly separating (if needed) and aligning each assembly with respect to each other and possibly also with respect to the treated area. For instance, 2 disc assemblies may be configured such that a keel on one assembly should be approximately 13 mm from the center of a keel on the second disc assembly. The distance between keels may be varied to account for differences in the radius of curvature of the sliding surfaces, the location of the keel on each disc assembly, the condition of the anatomy in the treated area, and the like.

While the precise distance between keels does not need to be specified, the physician should understand how to align and position the disc assemblies. For instance, the distance between keels for proper alignment may be selected from a range from about 5 mm to about 20 mm, or from about 10 mm to about 15 mm, and the selected distance may then be provided to the physician or accounted for in the tools provided to the physician.

In one embodiment, each of the two disc assemblies is positioned and aligned a predetermined distance from the midline of the vertebral body in the anterior-posterior direction. For instance, as shown in FIG. 71, the trial may be inserted into the treated area on one side of the spinal cord such that the center of the chisel guide, when properly positioned, is from about 3 mm to about 10 mm from the midline of the vertebral body. More preferably, the center of the chisel guide when properly positioned is from about 4 mm to about 8 mm from the midline of the vertebral body.

Once the trial is in its proper position, the grip of the handle may be removed. Preferably, the handle is formed oat least a detachable grip and a shaft in communication with the trial. When the grip is removed, the shaft may then be used as a guide rod for additional tooling and instruments.

For example, once the grip is removed, the shaft may be used as a guide for applying a chisel to form grooves or channels in the treated area. More specifically, with reference to FIGS. 70-72, a chisel 200 may be provided that can slidingly engage with the shaft of the handle to help ensure that the chisel is positioned properly for forming a channel or groove in one or both vertebral bodies adjacent to the treated area. In one embodiment, a portion of the chisel 200 forms a tube 206 or aperture having a cross-section corresponding approximately in the cross-section of the handle shaft. The tube or aperture may be slightly larger to allow the chisel to move more easily along the length of the shaft.

As shown in FIG. 70, the end of the chisel that impacts against, cuts or otherwise contacts the vertebral bodies has chisel blades 202 that may be shaped and configured to form grooves or channels in the vertebral bodies of a desired shape. Thus, in one embodiment, the cross-sectioned shape of the chisel blade is a truncated wedge. In one embodiment, the cross-section of the chisel blade may be approximately the same as the cross-section of the keel of the disc assembly. The end of the chisel opposite the chisel blade may have an enlarged impaction face 204. Thus, the physician may align and position the chisel blades 202 against one or more vertebral bodies neighboring the treated area and strike the impaction face 204 to drive the blades into the vertebral bodies. As the chisel blades are worked into the treated area, the blades may be guided and maintained in proper position by slidingly engaging with the chisel guide 196 formed on the trial. Preferably, the length of the chisel may be selected such that the chisel blades have progressed to their desired position when the impaction face is flush with the handle shaft.

In one embodiment, the chisel blade may be selectively detached from the chisel. As shown in FIGS. 72-74, for example, the impaction face 204 and chisel tube 206 may be separated from the chisel blades and removed. Likewise, the trial may be selectively detached from the handle shaft. Thus, it is possible to remove these components of the instruments and leave the trial and chisel blade in the treated area, as shown in FIG. 74.

Turning to FIG. 75, with the trial and chisel blades remaining in position, the spinal cord may be repositioned or moved slightly to provide access to the contra-lateral side of the treated area. As previously discussed, the trial may be configured with a keyed recess 198. The keyed recess 198 is positioned so that it faces toward the contralateral side of the treated area (i.e., toward the midline of the vertebral body in the A-P direction). Alternatively, the trial may be configured with two keyed recesses 198 formed on opposing lateral faces of the trial. This configuration would permit the trial to be inserted on either side of the spinal cord. As shown in FIG. 76, an angled guide 208 may then be inserted into the treated area on the contra-lateral side of the area from the trial and chisel blade. Preferably, the angled guide comprises an angled head 210 and a shaft 212 that is substantially straight. Thus, the shaft 212 may be substantially parallel to the longitudinal axis 214 of the chisel blades when the angled guide is properly connected into the keyed recess.

The angled guide may be selectively engaged with a keyed recess of the trial so that is may be attached or removed as desired. Preferably, the angled guide is only capable of engaging with the keyed recess at one angle and orientation. In other words, the angle with which the angled guide is inserted into the keyed recess is predetermined and known. In some embodiments, the angled guide and the keyed recess may have complementary surfaces that allow a surgeon to determine when the angled guide has been fully inserted into the keyed recess. Once the angled guide is in communication or proper registration with the keyed recess, the shaft extending outward of the treated area may then be used to insert a second chisel blade into the treated area. As shown in FIG. 76, the cross section of the shaft of the angled guide may be generally oval, but it also may be rectangular, square, triangular, oblong, elliptical, or have some other shape that helps prevent rotation of a chisel blade as it is being inserted. Of course, it is preferable that the second chisel blade has a tube or aperture corresponding generally to the shape of the cross-section of the angled guide. Preferably, the second chisel is substantially the same size as the first. The blade may then be placed on the shaft of the angled guide and positioned near or adjacent to the vertebral bodies. A chisel tube and impaction face may once again be employed to drive the chisel blade into the treated area.

One advantage of engaging the angled guide with the keyed recess is that the chisel blades into the contra-lateral side of the vertebral body may be inserted at a known distance away from the first set of chisel blades. Another advantage of using the angled guide may be that the chisel blades on the contra-lateral side of the vertebral body may be inserted substantially parallel to the first set of inserted chisel blades. In one embodiment, the angled guide is preferably configured and dimensioned such that the chisel blades on the contra-lateral side are inserted between about 8 mm and about 16 mm away from the first set of chisel blades. More preferably, the chisel blades on the contra-lateral side are inserted between about 10 and about 15 mm away, and most preferably, the chisel blades on the contra-lateral side are inserted between about 12 mm and about 14 mm away from the first set of chisel blades.

Once the chisel blade has been fully placed or inserted into in the contra-lateral side of the treated area, it may then be removed from the treated area along with the angled guide. In one embodiment, both the chisel blade and angled guide are removed at the same time (i.e., the angled guide may be removed with the chisel blade still disposed on the shaft). As shown in FIG. 78, a disc assembly 216 may then be deployed into the contra-lateral side. To facilitate insertion of the disc assembly 216, an implant holder 218 may be used to securely grip the assembly until its keels are inserted into the grooves or channels formed by the chisel. FIG. 78 illustrates one embodiment where the implant holder may selectively engage with the rear-most or posterior side of the disc assembly. As shown in FIGS. 62A and 78, rearward ends of the upper and lower portions of the assembly may have receptacles 220 that allow the holder to securely grip the assembly. In addition, hooked tips 222 formed on the holder may selectively engage with the assembly components. Configuring the disc assembly and implant holder in this manner allows the overall height and width needed for insertion of the disc assembly to remain at a minimum.

Alternatively, the implant holder 218 may engage with the outermost upper and lower surfaces of the disc assembly, on either side of the keels. However, this configuration may require the vertebral bodies to be distracted during insertion, thereby potentially causing the first chisel blade and/or the trial to become dislodged from their positions. Additionally, an implant holder may grip the disc assembly from the lateral sides; however, this too may require an increase in the overall size of the window or opening needed in order to insert the disc assembly. Thus, while the use of these alternative embodiments may fall within the scope of the invention, some may have disadvantages.

Once the keels of the disc assembly have begun to be positioned on over the channels or grooves, the implant holder may be used to push the disc assembly into the treated area. As the disc assembly nears its final position, resistance between the vertebral bodies and the surfaces of the disc assembly may significantly resist further progress. If desired or needed, gentle impact forces may be applied to the implant holder to aid in moving the disc assembly into position.

The first chisel blade and trial may then be removed and a second disc assembly inserted in a similar manner. In particular, the chisel blade may be operatively connected with the chisel tube or another instrument and then withdrawn from the body. Likewise, the handle shaft, and optionally the grip, may be reconnected to the trial so that it too can be withdrawn. The removal of the trial and chisel blade can be performed at the same time or sequentially. Once the trial and chisel blades have been removed, the second disc assembly may be inserted. FIGS. 68-80 generally illustrates how two disc assemblies may be inserted from a posterior approach into their desired positions.

As mentioned previously, the keel of a disc assembly may be configured to promote or permit bony ingrowth that may help hold the disc assembly in place more securely. FIG. 82 illustrates one embodiment of a keel having a plurality of slots or cuts formed in it. FIGS. 62E and 62H also show other examples of slotted keels. Returning to FIG. 82, the slots or cuts may extend at an angle, such as from about 5° to about 40° off from a vertical direction, and more preferably from about 10° to about 30°. A keel may have two or more, or even three or more slots or cuts. One skilled in the art would appreciate that other configurations may also be used to promote bony ingrowth that might help further secure the disc assembly in place. For instance, the keel may have holes or apertures drilled into it, longitudinal or horizontal slots may be formed, and the sidewalls of the keel may be textured with one or more grooves or channels that does not extend fully through the keel to the opposing sidewall.

In addition, the face of the keel that first inserted into a groove or channel may have a taper or chamfer. One potential advantage of configuring a keel with a taper or chamfer on its face is that it may assist in aligning the keel with the opening of the channel or groove. In addition, a chamfered or tapered face may help reduce drag forces and undesired cutting or gouging of the channel or groove as the keel is pushed toward its final position.

One advantage of providing multiple assemblies to form the artificial disc is that it allows the assemblies to be placed into position without significant vessel retraction. Thus, insertion from the anterior of the vertebral bodies can be achieved with minimal repositioning of the vena cava or aorta. Because the wall of the vena cava is a thin, it punctures or tears more readily than other vessels.

Conversely, the wall of the aorta is thicker than the vena cava, and therefore more resistant to tearing or punctures, but the pressure of the blood supply is considerably higher. As a result, damage to the aorta can result in significant blood loss. Therefore, one benefit of a multi-assembly artificial disc is the reduced need to disturb or move these major blood vessels.

Another advantage to using a multi-assembly configuration is that it permits a physician to adjust or replace one or more assemblies from a different approach than used during the original insertion of the disc. When an implant is placed in a region of the spine, a region surrounding the area of insertion can become obscured or blocked by scar tissue that gradually forms after the procedure. This scar tissue can also bind to neighboring anatomy, including the major blood vessels so that it is extremely difficult to reuse the insertion window again without substantial risk to the patient.

When multiple assemblies are used, however, it is possible to use a second approach to adjust, remove, or replace the artificial disc. For instance, if disc assemblies are inserted into position from the anterior side of the vertebral body, it would be possible to remove or adjust the assemblies using a posterior approach using the methods, tools, and techniques described herein. Likewise, a multi-assembly artificial disc can be inserted from a posterior direction, thereby leaving the anterior side available for future access to the disc.

In some instances, it may be desirable to use a second approach to adjust, remove, or replace an artificial disc at a later time. For example, a disc may be inserted during a first surgery. Normal body movement over a period of time may then necessitate adjustment of the artificial disc. The present invention allows a surgeon to re-enter the vertebrae using a second approach. The second approach may be done at any desired time. For example, a second surgery using a second approach may be performed about six months or more after the first surgery. More preferably, a second surgery using a second approach may be performed about one year or more after the first surgery. Most preferably, a second surgery using a second approach may be performed about five years or more after the first surgery.

As discussed previously, where more than one implant or assembly is inserted into the intervertebral space, precise placement of each insert may be desired. Because the articulating surface of each assembly relies or cooperates with the articulating surface of its corresponding assembly, precise placement of the assemblies is preferable. More particularly, precise placement refers to the placement of one assembly such that it is aligned and spaced apart from the other assembly or assemblies in such a way that each articulating surface of the respective assemblies may cooperate with each other to form an effective range of movement as if there were a unified articulating surface. For example, with respect to the embodiment disclosed in FIGS. 86 to 110, precise placement means that each keel of each assembly lie parallel to each other. Additionally, each assembly would be spaced apart from the other assembly such that each independent articulating surface allows the articulating surface of its corresponding assembly to act as or mimic one complete surface, i.e. one semispherical articulating surface. In one particular embodiment, each assembly should be inserted at a proper predetermined depth within the intervertebral space, and each assembly should be inserted generally to the same depth. In assuring such precise placement, methods and tools have been developed in accordance with the present invention for ease of implantation and accuracy. Furthermore, in controlling each of these positioning variables, a surgeon should be careful during the entire procedure to avoid contact with the spinal cord while working within confined spaces.

In an exemplary embodiment of the present invention, methods and tools are provided for inserting more than one assembly of a prosthetic disc. The methods and tools relate to positioning a second implant based on the position of a first implant. As discussed previously, any number of methods may be used to position a second implant based on the position of the first implant. As used herein, "based on" means the positioning or placement of a second object, path, cut, or other item as determined by a position or placement of a first item. In the embodiment described below, the positioning of a second implant may be accomplished by using a path cut by a first chisel to determine the path cut by a second chisel.

In general, prior to insertion of the prosthetic disc, the intervertebral space is prepared. In one variation, a surgeon performs a lamenectomy or laminotomy to remove all or part of the lamina. This procedure is used to create a "window" through which the surgeon may access the intervertebral space. In some instances, a surgeon may perform a total discectomy, in which the disc between two vertebrae is removed. Alternatively, a surgeon may perform a partial discectomy, in which only a portion of the disc is removed. Partial discectomies typically leave a portion of the annulus of the disc intact on the anterior portion of the interverterbral disc space. The present invention is not limited to any particular type of disectomy, whether complete, partial or otherwise.

In one embodiment, another step in the process of inserting a prosthetic disc according to the present invention may include preparation of the upper and lower surfaces of the vertebral bodies. In this step, a surgeon may scrape the upper and lower surfaces of the vertebral bodies. Scraping the surfaces may cause some bleeding, which may improve the chances of bony growth into the inserted assemblies.

In another embodiment, the disc space is prepared by inserting various tools to help loosen the muscles and ligaments that keep the disc space together. In this embodiment of the present invention, a paddle distractor may be used. With reference to FIG. 86, a paddle distractor 250 is provided. Paddle distractor may have a handle 252 that is attached to an elongated shaft portion 254. At the end of elongated shaft portion 254 the paddle distractor has an area shaped as a paddle 256, or an area that is wider than its thickness. The length of paddle area or paddle head 256 may vary, although one of skill in the art would recognize that said length would be sized appropriately so as to enter the intervertebral space without interfering with surrounding tissue or other internal body parts. The shape of the paddle area allows a surgeon to insert the instrument in one direction, Le. generally flat or so that face 258 of paddle area 256 is generally parallel to the upper and lower surfaces of the upper and lower surfaces of the vertebral bodies between which it is being inserted. Once inserted, a surgeon may rotate handle 252 in turn causing paddle area 256 to rotate within the vertebral space. As sides 260 and 262 contact the upper and lower surfaces of the vertebral bodies, the disc space is distracted and the muscles and ligaments are loosened. This helps prepare the disc space for insertion of the trial.

As one of skill in the art would understand, the size and shape of the paddle distractor may vary and various sized instruments may be provided to accommodate different areas of the spine or distraction preferences by the surgeon. Furthermore, distractors of various sizes may be used to within the same space to distract the space in a step wise fashion. As seen in FIG. 86 handle 252 may be releasably attached to shaft 254. In this fashion, a single handle may be provided with a set of paddle distractors with various sizes of paddle heads such that a surgeon may select different paddle distractors according to surgeon preferences and patient anatomy. While any number of sizes may be used, in one embodiment a set of paddle distractors with paddle heads having widths of 10 mm to 17 mm, with a separate paddle distractor for each different millimeter width, is provided. In some embodiments, a set of paddle distractors are provided wherein there is a paddle distractor, with an appropriately sized paddle head, for each trial in the set or kit.

Figure 87:
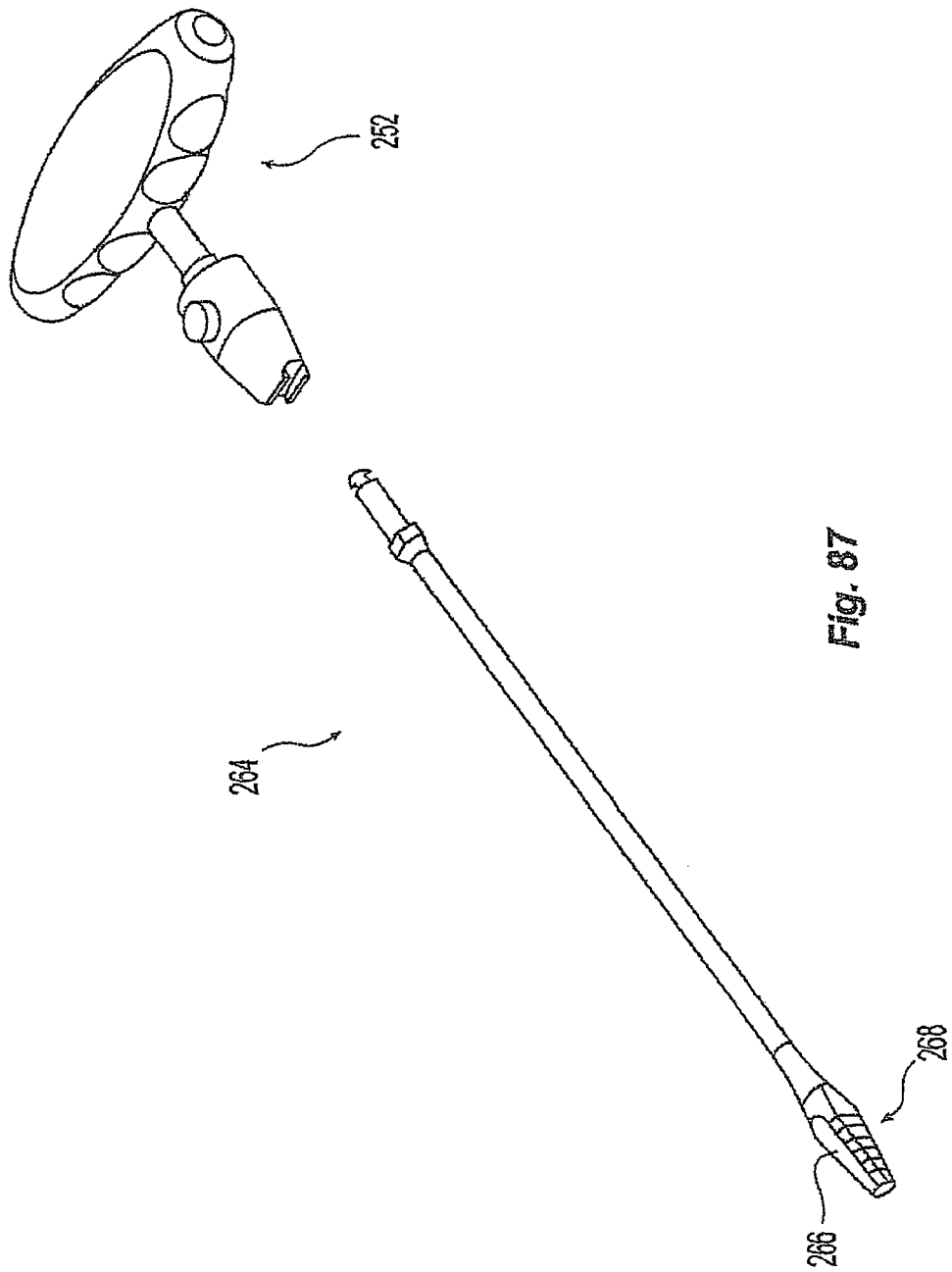
FIG. 87 illustrates one embodiment of a tool used in the methods of the present invention.

In an alternate embodiment, a dilator may be provided. With reference to FIG. 87, a dilator is shown. As seen in FIG. 87, dilator 264 is similar to paddle distractor 250 except that the end of dilator 264 is configured as a generally regular pyramid. As one of skill in the art would understand, the shape and configuration of the dilator can aid the surgeon in preparing the disc space by serving as a wedge as the dilator is inserted into the intervertebral space. As further seen in FIG. 87, demarcations 266 along the generally pyramid area 268 correspond to the thickness or width of the area at that point. Thus, a dilator with widths or thickness between 8 mm and 12 mm may be used and the surgeon may distract the intervertebral space by a desired amount by inserting the dilator to the appropriate depth. In an embodiment of the present invention, a set of dilators may be provided that correspond to a range of distraction sizes. For example, in one embodiment, a surgeon may be provided with three dilators that contain a range of sizes of about 6-12 mm, 8-14 mm, and 10-16 mm. As with the paddle distractor, handle 252 may be releasably attachable such that a surgeon may use the same handle for different dilators. As one of skill in the art would understand, a kit may be provided that contains both dilators and paddle distractors. In this embodiment, a single handle may be used for both the different dilators and different paddle distractors.

After preparing the intervertebral space the next step performed according to one embodiment, a surgeon determines the appropriate size of the assembly to use in the procedure as well as the desired position of the assembly. The present invention contemplates tools and assemblies of various sizes to help a surgeon determine the appropriate prosthetic disc to implant. Trials, of various sizes, are commonly used in this type of surgery to "test fit" items inserted into intervertebral spaces. Specially configured trials may be provided to aid in the positioning of a second assembly based on the position of a first assembly.

Figure 88:
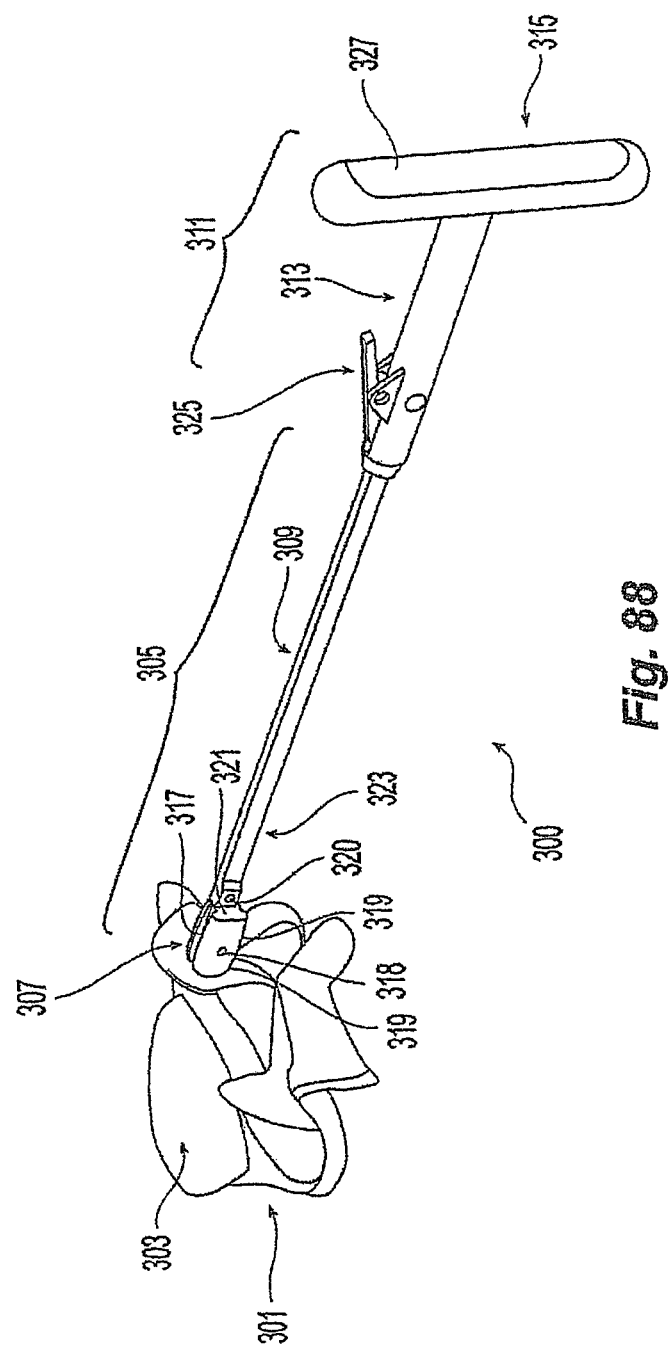

As seen in FIG. 88, a first trial 300 is shown. In FIG. 88, only lower vertebral body 301 is shown. Also, in the following figures, the various instruments and assemblies are shown offset from the vertebral body. This view is provided to show more of the various tools and assemblies and one of skill in the art would understand that in practice, the assemblies and tools would lie within the intervertebral space. As one of skill in the art would also understand, an upper vertebral body is also present but, for the sake of visual clarity, not shown. In operation, first trial 300 may be inserted into the intervertebral space 303 and the surgeon may then orient the trial 300 to determine the best position for the implant.

As discussed previously, a number of different trials of varying sizes may be provided. The surgeon may test different trials to determine the size, angle, and length of the implant appropriate for the patient. The surgeon may select the appropriate size trial based on a number of criteria including restoring disc height to the appropriate level or implanting assemblies based on the structural characteristics of the upper and lower vertebral bodies, including for example, surface area and strength of the surfaces.

As seen in FIG. 88, trial 300 comprises a first portion 305 that includes a trial head member 307 and a trial shaft member 309 and a second portion 311 having a shaft member 313 and a handle member 315. Trial head member 307 is configured to mimic the size and shape of a prosthetic disc assembly. Trial head member 307 is further configured with keyed recesses 317, 319. Keyed recesses 317, 319, as discussed in more detail below, are configured to receive and help guide chisel blades.

Trial shaft member 309 of first portion 305 of trial 300 extends along an axis. Trial shaft member 309 of first portion 305 is connected to trial head member 307. As seen in FIG. 88, in one embodiment, trial shaft member 309 is connected at a position offset from the centerline of trial head 307 in the direction away from the spinal cord (not shown). As one of skill in the art would understand, the offset connection imparts increased functionality to trial 300. The offset connection decreases the amount of distraction of the spinal cord to access the intervertebral space. The offset further reduces the risk that the trial might contact the spinal cord, thus reducing the chance of injury to the nervous system of the patient.

Trial head member 307 is further configured with a flat face 321 on the proximal side of trial head 307. Flat face 321 is configured as a stop when trial 300 is used with a chisel, which is described in more detail below. As seen in FIG. 88, trial shaft member 309 of first portion 305 may also be shaped to accommodate the spinal cord. Area 323 of trial shaft member 309 of first portion 305 is carved out on the side facing the spinal cord to further reduce the potential contact between trial shaft member 309 and the spinal cord. This area may be carved out from a portion of the shaft such that there is a reduced thickness of the shaft in the area of the spinal cord. The shaft 309, as seen in FIG. 88, has other areas that are thicker to maintain rigidity and add strength to the tool. As one of skill in the art would understand, variations could be employed to achieve similar results.

At the proximal end, trial shaft member 309 of first portion 305 connects to second portion 311 of trial 300. Second portion 311 of trial 300 also includes a handle member 315, which is connected to shaft member 313 of second portion 311. As seen in FIG. 88, trial shaft member 309 and shaft member 313 can be connected to each other. In one embodiment, handle member 315 may include a mechanism by which it may be operatively attached and removed from first portion 305. In one variation, the mechanism is a lever 325 that may be actuated by a user. Shaft member 313 of second portion 311 is configured with a hollow area to receive the proximal end of trial shaft member 309 of first portion 305. Trial shaft member 309 of first portion 305 may also be configured to engage lever 325 (hidden). One of skill in the art would understand that any number of different connection types including but not limited to threaded connections, pins and slots, friction fits, or others may be used to connect trial shaft member 309 of first portion 305 with shaft member 313 of second portion 311.

As further seen in FIG. 88, handle portion 315 is configured for a user to grasp. Handle 315 is designed to provide a surgeon with control over the insertion and positioning of trial 300 within the intervertebral space. In one embodiment, handle 315 may also be configured with a flat face 327. Flat face 327 of handle 315 is designed to give a surgeon an impaction surface. Surgeons or other users may strike the impaction surface with a hammer or other tool to drive or insert the trial into the intervertebral space, if desired.

As further seen in FIG. 88, trial 307 is configured with through holes 318 and 320. Through holes 318 and 320 may be used by the surgeon to position the trial within the intervertebral space. As one of skill in the art would understand, a surgeon may take radiological or other images of the trial position during surgery. Through holes 318 and 320 provide the surgeon with a reference point. For example, in one embodiment, through hole 318 is placed at the center of the trial head. Thus, during implantation, the surgeon may use through hole 318 to position the center of the trial. This may be useful to a surgeon to allow him or her to determine the point at which the assemblies of the prosthetic disc will be implanted, and hence the location(s) of the instantaneous axis of rotations. Similarly, through hole 319 may be used to measure whether the trial head is sufficiently within the intervertebral space. For example, by taking a lateral image of the intervetrebral space, the surgeon can determine whether the trial has been placed at a sufficient depth such that the assemblies will be fully within the intervertebral space when implanted.

Figure 89:
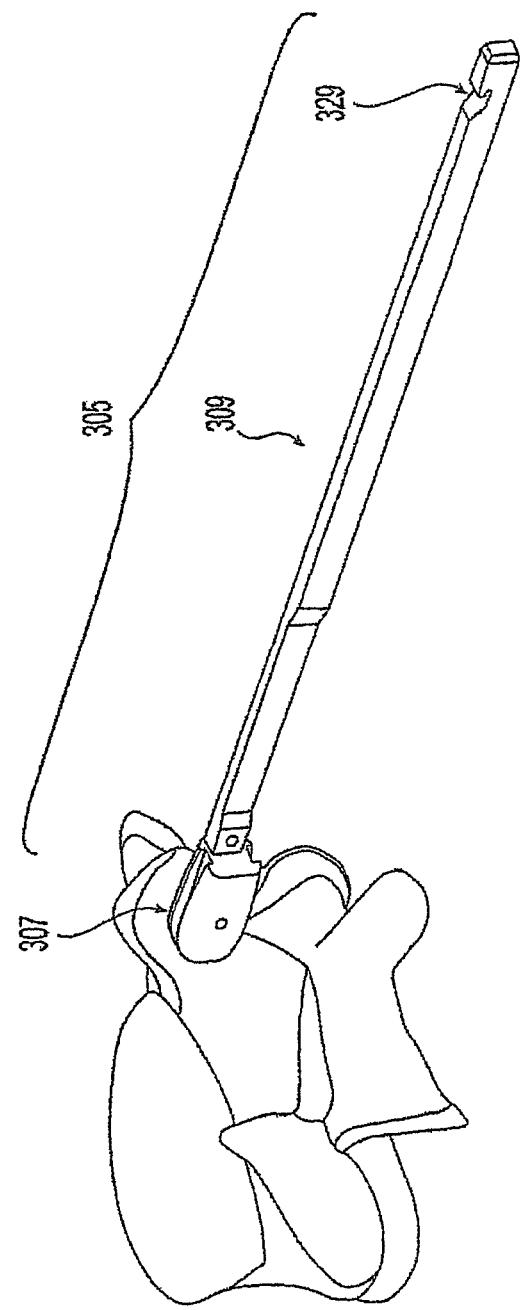

In one embodiment, the trial has been positioned according to the preferences of a surgeon, second portion 311 may be detached. Referring to FIG. 89, first portion 305 of trial 300 is shown after second portion 311 of trial 300 has been detached. Referring to FIG. 89, the proximal end of shaft 309 may be configured with an engagement area 329. Engagement area 329 interacts with lever 325 of second portion 311 of trial 300 (not shown).

Referring to FIG. 89, trial shaft member 309 of first portion 305 of trial 300 may be configured with a particular shape. In an exemplary embodiment, shaft 309 is configured with a generally rectangular shape. The shape of shaft 309 is designed to cooperate with other tools and parts used in the method. Accordingly, the hollowed out area of the second portion 311, and more particularly shaft 313, may be configured to match the generally rectangular shape of shaft 309. Thus as should be readily apparent, the shaft 313 may only be inserted over shaft 309 in two orientations. This provides the tools with orientation preferences, which when applied to other parts of the method prove useful. As one of skill in the art would understand, the particular shape may be changed and may include no limitations on the orientation of the various pieces (such as in circular shapes) or only one orientation allowed (such as a scalene triangle shape).

Figure 90:
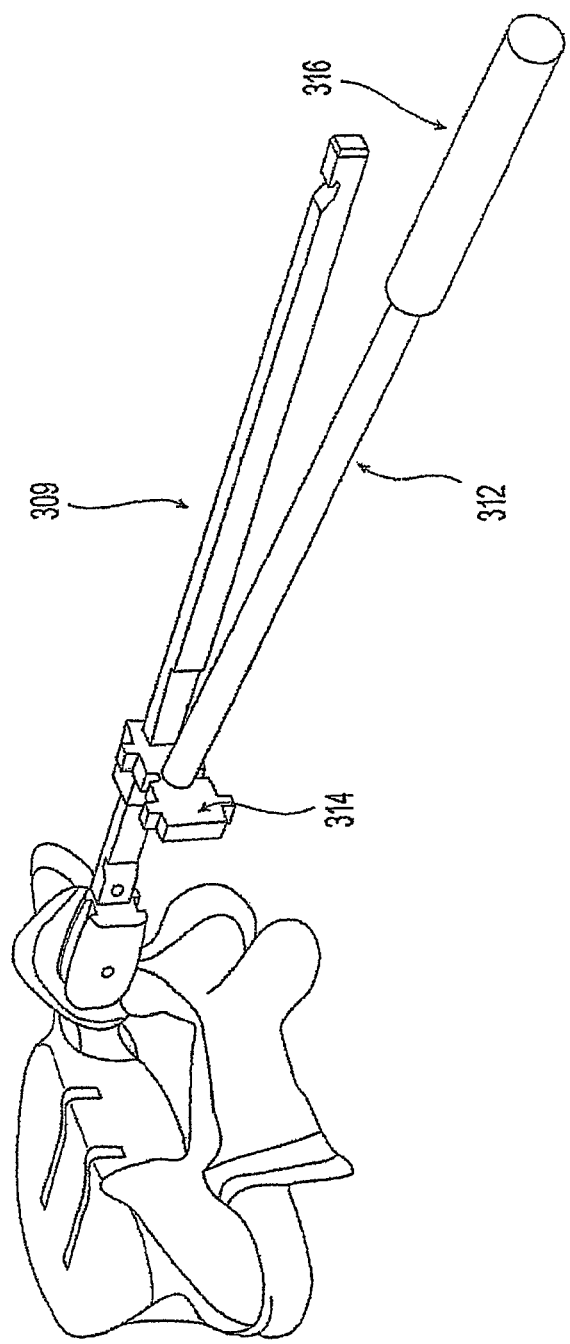

In one embodiment, a laminectomy centering guide is provided. Referring to FIG. 90, lamenectomy centering guide 312 comprises a template piece 314. Template piece 314 is sized and dimensioned to approximate the needed window or space that needs to be created in the lamina. Template piece 314 may be keyed to trial shaft portion 309, as seen in FIG. 90. Template piece may also be connected to a handle 316 so a surgeon may position the template piece 314 over the lamina to use said template piece 314 as a guide and then excise the required tissue/bone as desired. In an embodiment of the present invention, the handle is angled with respect to the front face of the laminectomy centering guide to provide the surgeon with a better line of sight. In an embodiment of the present invention, the handle is angled by 10°. In an embodiment of the present invention, the handle is angled by between about 3° and 20°. A kit may be provided wherein there is more than one laminectomy centering guide. In such an embodiment, various sizes of a guide are provided. Accordingly, a kit may contain a guide for each of the differently sized implants. In some embodiments, the handle may be detachable from the template guide. In this fashion, various templates may be provided and only one handle is needed. As one of skill in the art would understand, the precise configuration of the template piece and handle may vary, and the methods of the present invention contemplate providing template pieces of varying sizes to accommodate different patient requirements or surgeon preferences.

In one variation of an embodiment of a method according to the invention, after detaching second portion 311 of trial 300, paths may be cut in the upper and lower surfaces of the vertebral bodies within the intervertebral space. The paths cut into the surfaces of the intervertebral space are generally configured and dimensioned to correspond to accommodate the keels on the endplates of the prosthetic disc assemblies. Accordingly, the paths cut, their size, their angle, etc. each relate to the specific type of keel (and their configurations) used in the prosthetic disc being inserted.

Figure 91:
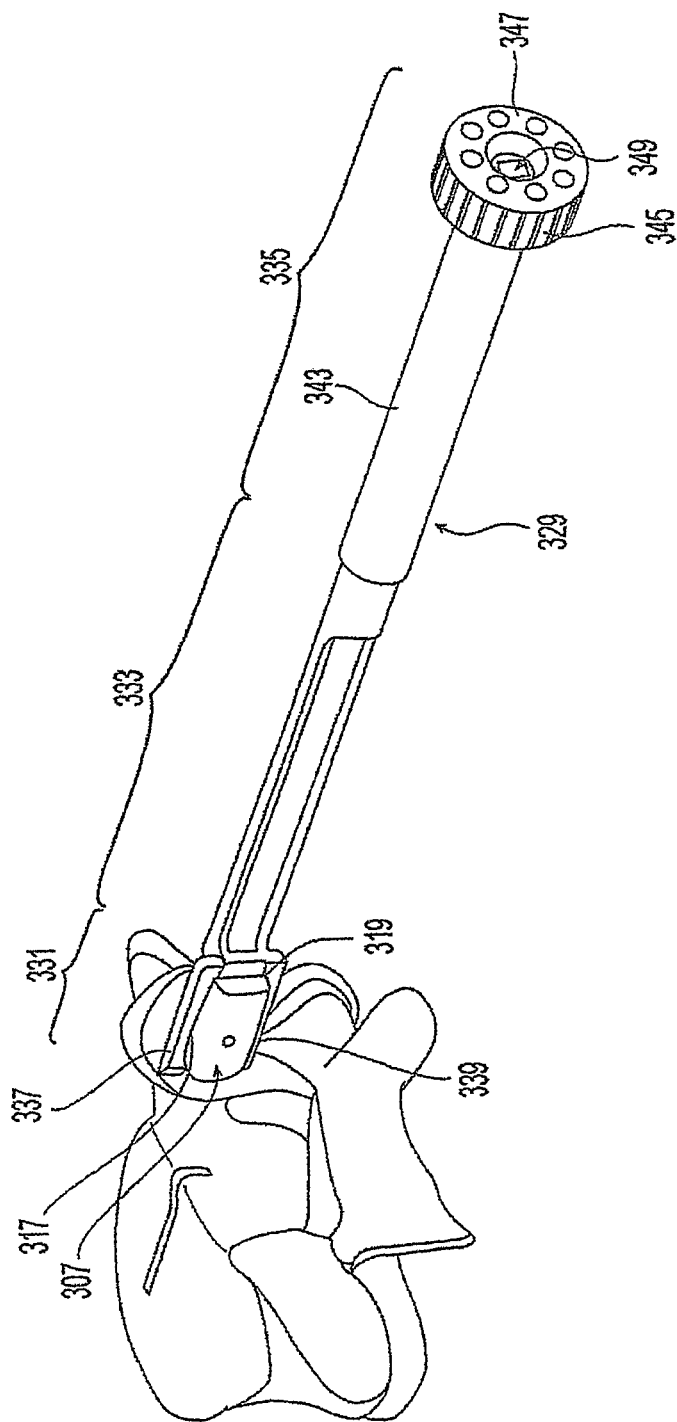

Referring to FIGS. 89 and 91, trial head 307 of trial 300 is configured to aid in the alignment and guidance of the chisel. In FIG. 91, chisel 329 is shown after insertion onto first portion 305 of trial 300. Chisel 329 has a blade portion 331, a shaft portion 333, and a handle portion 335. Blade portion 331 is forked having two blades 337 and 339 connected to a central member 341. Blade portion 331 is configured and dimensioned such that upon insertion, blades 337, 339 partially extend above and below trial head 307. As best seen in FIG. 91, trial head 307 is configured with two recesses 317 and 319, which are keyed into the upper and lower surfaces of trial 307. Blades 337 and 339 partially ride within keyed recesses 317 and 319 as the chisel blades are driven into the vertebral bodies to create or clear a path in the bone. As one of skill in the art would understand, trial head 307 is configured to receive and guide blades 337 and 339 of chisel 329, however, alternate chisels and blade designs may be employed to achieve similar results.

Referring to FIG. 91, chisel portion 331 is connected to shaft portion 333. As described above, in one embodiment, the chisel portion 331 may be offset from the shaft portion 333 of chisel 329. This design feature maintains the offset configuration discussed with respect to the trial to maintain the path-cutting tool away from the spinal cord.

Shaft portion 333 of chisel 329 is configured with a hollow section so that it may fit over and slidingly engage shaft 309 of trial tool 300. Similar to shaft 309 of the trial tool 300, shaft 333 of the chisel tool 329 may be cut away on the side facing the spinal cord, as seen in FIG. 91. This feature (as the similar feature does in the trial tool) creates additional space on the side of the spinal cord to minimize potential contact or injury with the spinal cord. In one embodiment, the hollow section of shaft portion 333 of chisel 329 is shaped to match the shape of shaft 309 of trial tool 300. As discussed previously, this feature requires insertion of chisel 329 over trial 300 at a particular orientation that ensures that the blades will be positioned correctly, i.e. with the blades cutting a pathway into the upper and lower surface of the vertebral bodies. As one of skill in the art would understand, a two-orientation configuration is adequate where the upper and lower keels of the prosthetic disc are similar, equivalent, or the same. Where the keels of the prosthetic disc assembly have different keels (and hence the paths that need to be cut need to be different), a single orientation device may be desired.

Handle portion 335 is connected to shaft portion 333 of chisel 329. In one embodiment, handle portion 335 contains a shaft member 343 connected to an impact member 345. Shaft member 343 is hollow and shaped to receive shaft 309 of trial 300. In one variation, impact member 345 is cylindrical in shape and has a flat face 347, which serves as an impact area. Flat face 347 may have a through hole 349. As chisel 329 is driven into position (guided by trial 300), central member 341 will contact trial head 307 at the final insertion point, i.e. the insertion point determined by the trial. Similarly, the length of shaft 309 and chisel 329 are configured such that when chisel 329 reaches its final insertion point, the end of shaft 309 is flush with the flat face 347 of handle portion 345. Accordingly, the end of shaft 309 fits through bore hole 347 and, if chisel 329 is driven by impacting flat face 347 including bore hole 349, the impaction tool will stop driving chisel 329 into bone. This combination of features provides a guide for the surgeon to indicate when the appropriate path has been cut into the vertebral bodies as well as acting as a stop to safeguard against creating longer pathways than required by the keels of the prosthetic disc assemblies.

Figure 92:
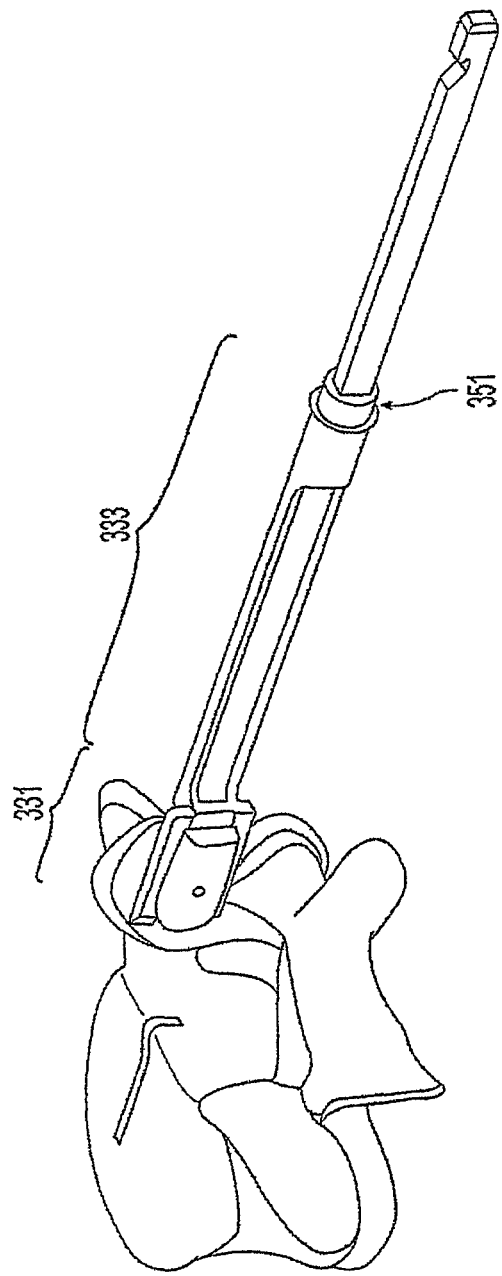
Figure 9A:
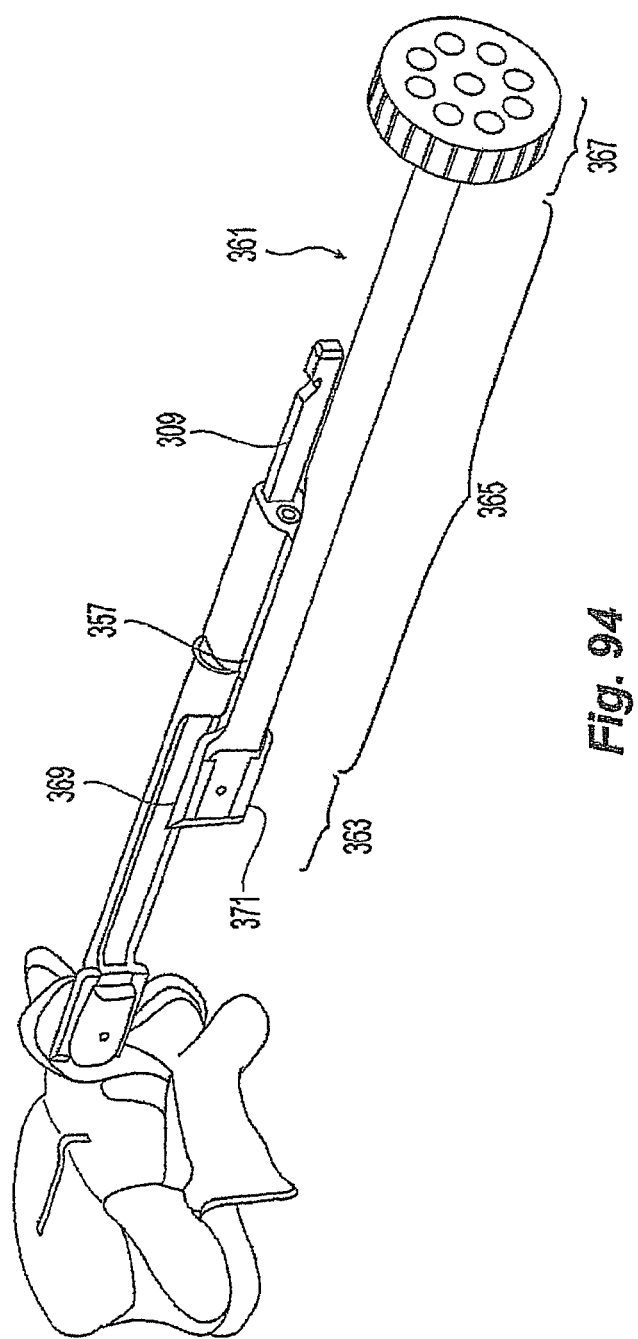

According to one embodiment of a method of the present invention, once the appropriate paths have been cut, handle portion 335 of chisel 329 may be removed. Referring to FIGS. 91 and 92, handle portion 335 has been removed from shaft portion 333 of chisel 329. As seen in FIG. 92, handle portion 335 and shaft portion 333 of chisel 329 are engaged with respect to each other at area 351. As handle portion 335 slides over shaft 309 of trial 300, handle portion 335 engages shaft 333 of chisel 329. As best seen in FIG. 92, handle portion 335 is configured to interface with shaft 333 of chisel 329. One of ordinary skill in the art would understand that any variety of configurations, including tongue and groove, threaded connections, or other configurations could be employed to achieve similar results.

According to one embodiment of a method of the present invention, after removing the handle portion 335 of chisel 329, an outrigger or positioning member may be slid onto trial shaft 309. As seen in FIG. 93, positioning member 353 slides onto shaft 309 until it engages with shaft portion 333 of chisel 329 at engagement area 351. Positioning member 353 is configured with a hollow section that is shaped to match the shape of shaft 309 of trial 300. In this embodiment, due to the rectangular configuration, the positioning member 353 is placed in a particular orientation, which will not move radially with respect to shaft 309 of trial 300.

In one embodiment, shaft 333 and blade portion 331 may remain inserted. Such a feature may provide a stop against which positioning member 353 may contact (at area 351) and may serve to lock trial 300 in place as a result of a friction fit between blades 337 and 339 and the vertebral bodies with which they may contact. Such a feature may secure the position of trial 300 and make it less likely that trial 300 will move during the remaining steps.

In one embodiment, positioning member 353 comprises an attaching portion 355, i.e. the portion that slides over shaft 309 of trial 300, and a guiding portion 357. Guide portion 357 is attached or connected to attaching portion 355 by a linking member 359 as seen in FIG. 93. Guide portion 357 serves as a hitch or post onto which a second chisel tool may be placed. While guide portion 357 is shown as generally cylindrical, any number of different shapes and configurations could be used. For example, guide portion could be generally rectangular, pyramidal, or square. The invention contemplates a guide portion shaped and configured to mate or key with the shape and configuration of the elongated shaft. Accordingly, one of skill in the art would understand that guide portion 357 is shaped to act as a guide and direct a chisel tool along a path parallel to trial 300.

With reference to FIG. 94, second chisel tool 361 is shown. Second chisel tool 361 has a chisel portion 363, shaft portion 365, and handle portion 367. As seen in FIG. 91, chisel portion 363 of second chisel 361 is configured similar to first chisel portion 331 of first chisel 329, except that the chisel portion 363 of second chisel 361 is not forked as it is in first chisel 329. In this regard, chisel portion 363 of second chisel 361 does not accommodate a trial head and accordingly is designed or constructed from one piece. The upper and lower surfaces 369, 371 of chisel portion 363, however, have blade portions or sharp edges configured similar to blades 337, 339 of chisel portion 331 of first chisel 329.

A shaft portion 365 is attached to the second chisel portion 363 of second chisel 361. Second chisel portion 363 may be similarly offset from shaft portion 365 as in previous descriptions to accommodate the spinal cord. Shaft portion 365 extends from chisel portion 363 and may comprise a sleeve or hollow body. As one of skill in the art would understand, the interior walls of shaft portion 365 may be shaped to match the external shape of guiding portion 357. In one embodiment, an opening may be formed along shaft portion 365 to provide access to the interior of shaft portion 365. Said opening is sized to accommodate guiding portion 357. Accordingly, second chisel 361 may be placed onto guiding portion 357 and slid towards the vertebral bodies. As guiding member 357 rides within the hollow body, which is shaped to match the hollow body of shaft portion 365 of second chisel 361, the second chisel is directed along a path which is parallel to trial 300 and spaced apart a set distance from trial 300.

In alternate embodiments, guiding portions and attaching members may be integral to the second chisel, and thus slidably engage or attach with the shaft of the first chisel. In alternate embodiments, a central member may be used that selectively engages the shafts of both the trial, first chisel, or second chisel. Accordingly, as one of skill in the art would understand, the precise mechanism by which the pathways are created may be any number of means.

Figure 95:
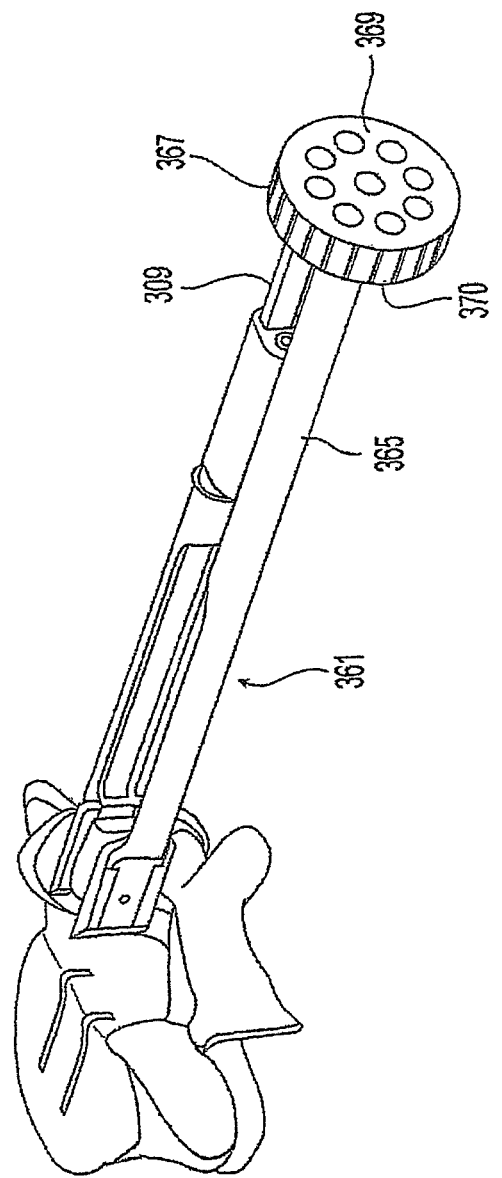

According to one embodiment of a method of the present invention and as seen in FIG. 95, the second chisel 361 may be driven into position by the surgeon. Shaft portion 365 is attached to handle portion 367. A surgeon may grip handle portion 367 and use it to position second chisel 361. In one embodiment, handle portion 367, as seen in FIG. 95, is a cylindrical body attached to shaft portion 365. Handle portion 367 may have a plurality of bore holes to decrease the weight of the overall tool. Handle portion includes a flat face 369, which serves as an impaction surface. Accordingly, a surgeon may use an impact tool to drive the second chisel 361. In alternate embodiments, shaft portion 309 is configured with a length that abuts underside face 370 of handle portion 367 when chisel 361 is in its final position. In these embodiments, flat face 370 may act as a stop. At this point in the method, four pathways have been made, two pathways in the upper and lower vertebral bodies each of the disc area being treated.

Figure 96:
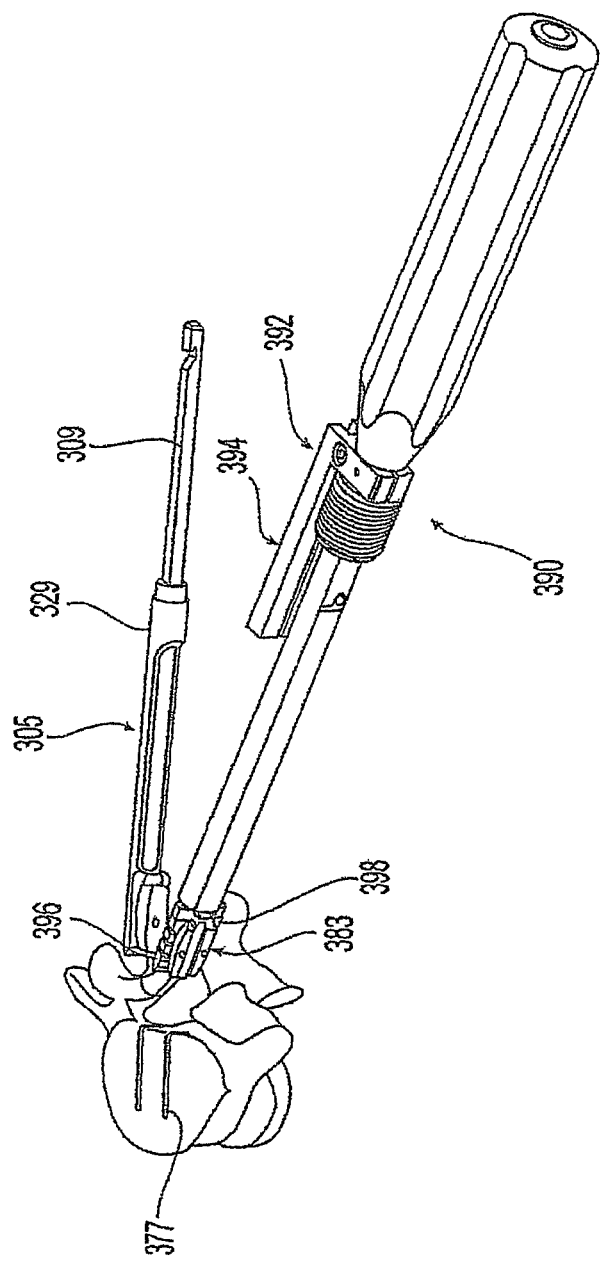

In an embodiment of the method presented herein, after cutting both paths into the vertebral bodies, a surgeon may remove only the second chisel 361. With reference to FIG. 96, a surgeon would remove the second chisel 361 and outrigger 353 from first trial 305, thus leaving first trial 305 in place. First trial 305 and first chisel 329 are left in place to both keep the intervertebral space separated as well as allow shaft 309 of trial 305 to serve as a guide for assembly implantation.

Figure 97:
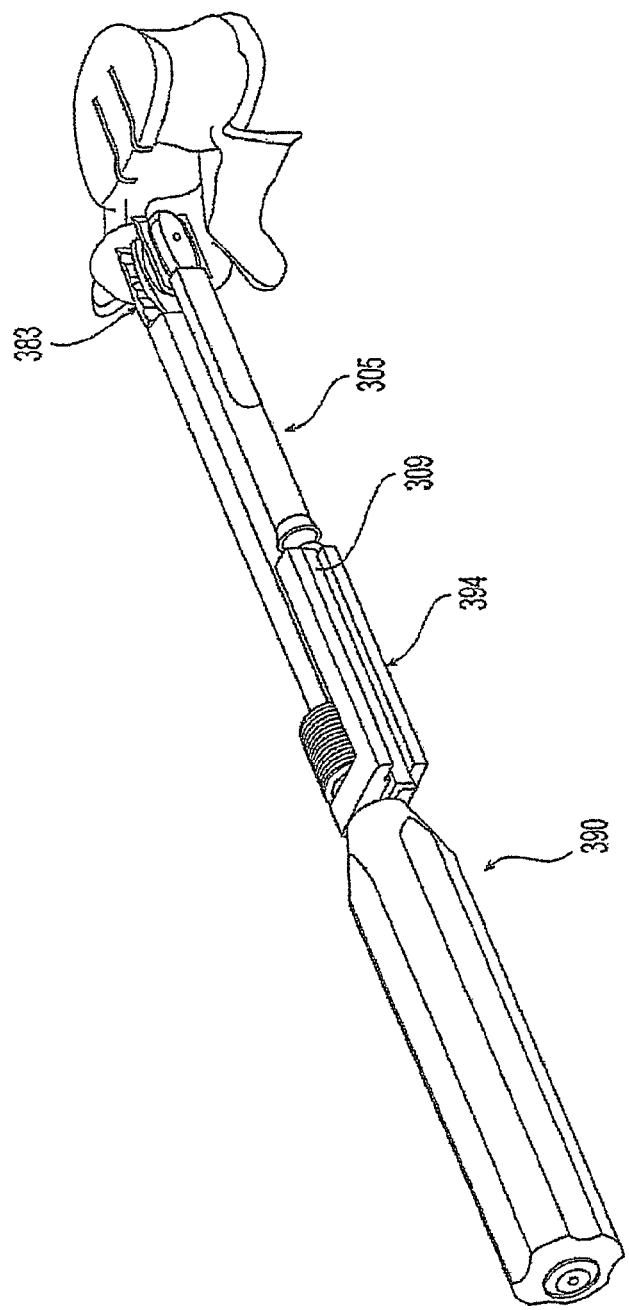

As seen in FIG. 96, an implant holder 390 attached to one assembly 383 is shown. Implant holder 390 is releasably attached to assembly 383. Implant holder 390 also comprises an implant guide 392. Implant guide 392 is rigidly attached to said implant holder and comprises a mating portion 394 that is configured to mate with shaft portion 309 of first trial 305. In an embodiment, mating portion 394 is configured as an elongated rectangle with a groove sized to accommodate the shape and configuration of shaft portion 309 of first trial 305. As one of skill in the art would understand, mating portion 394 attached to implant holder 390 keys implant holder 390 to shaft portion 309. Accordingly, a surgeon may place assembly 383 in an approximate position by introducing keels 396 and 398 into paths 371 (not shown) and 377. The surgeon may then swing implant holder 390 and key mating portion 394 onto shaft portion 309 of first trial 305. At that point, a surgeon may then drive assembly 383 into position. As one of skill in the art would understand, mating portion helps guide assembly 383 into position by maintaining a proper spacing between implant holder 390 and first trial 305. Additionally, mating portion 394 ensures that the assembly is inserted parallel to first chisel 305. With reference to FIG. 97, implant holder 390 is shown with assembly 383 60 inserted. As seen in FIG. 97, mating portion 394 is configured to provide a keyed mating connection before assembly 383 is inserted as well as allow implant holder 392 to drive assembly 383 along a path parallel to first trial 305 until assembly 383 has been inserted to a proper depth.

Figure 98:
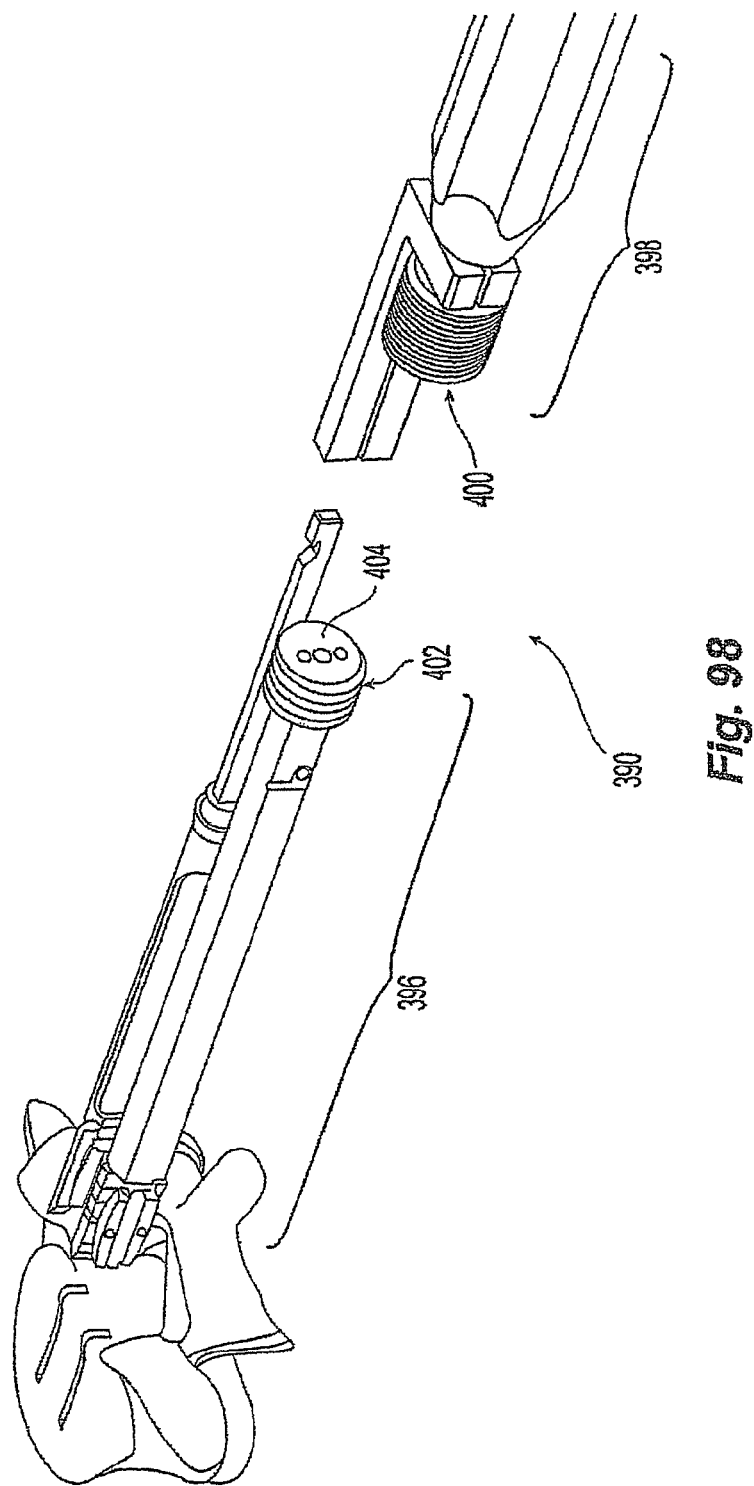

With reference to FIG. 98, implant holder 390 is comprised of a shaft portion 396 and handle portion 398. As seen in FIG. 98, handle portion 398 may be detached from shaft portion 396. The attachment mechanism may be any number of means although in this embodiment, handle portion contains an internally threaded rotatable cylinder 400 attached to handle portion 398 of implant holder 390. Internally threaded rotatable rod 400 is configured to mate with one end of shaft portion 396, which comprises an externally threaded cylindrical portion 402. Accordingly, rotation of internally threaded cylinder 400 can thus serve to either attach or release handle portion 398 from shaft portion 396 of implant holder 392.

Figure 99:
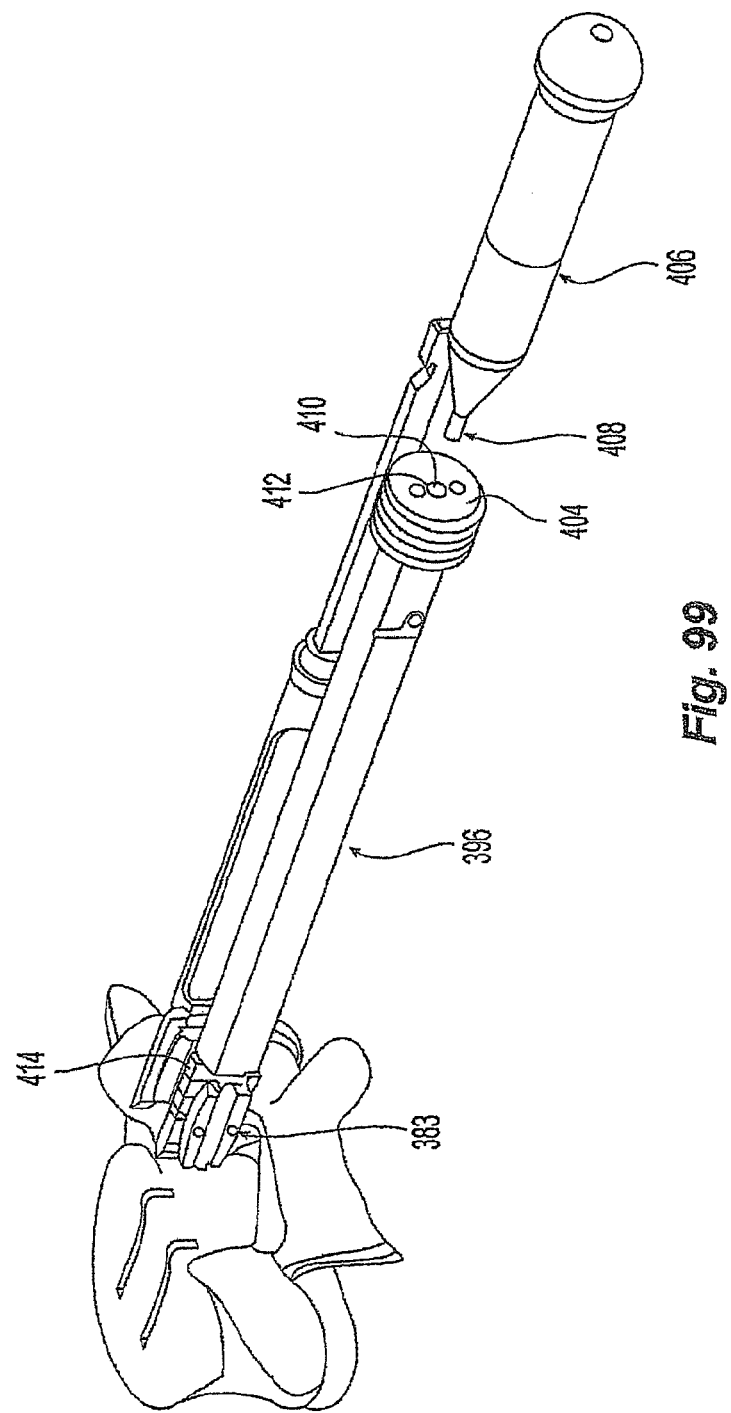
Figure 100:
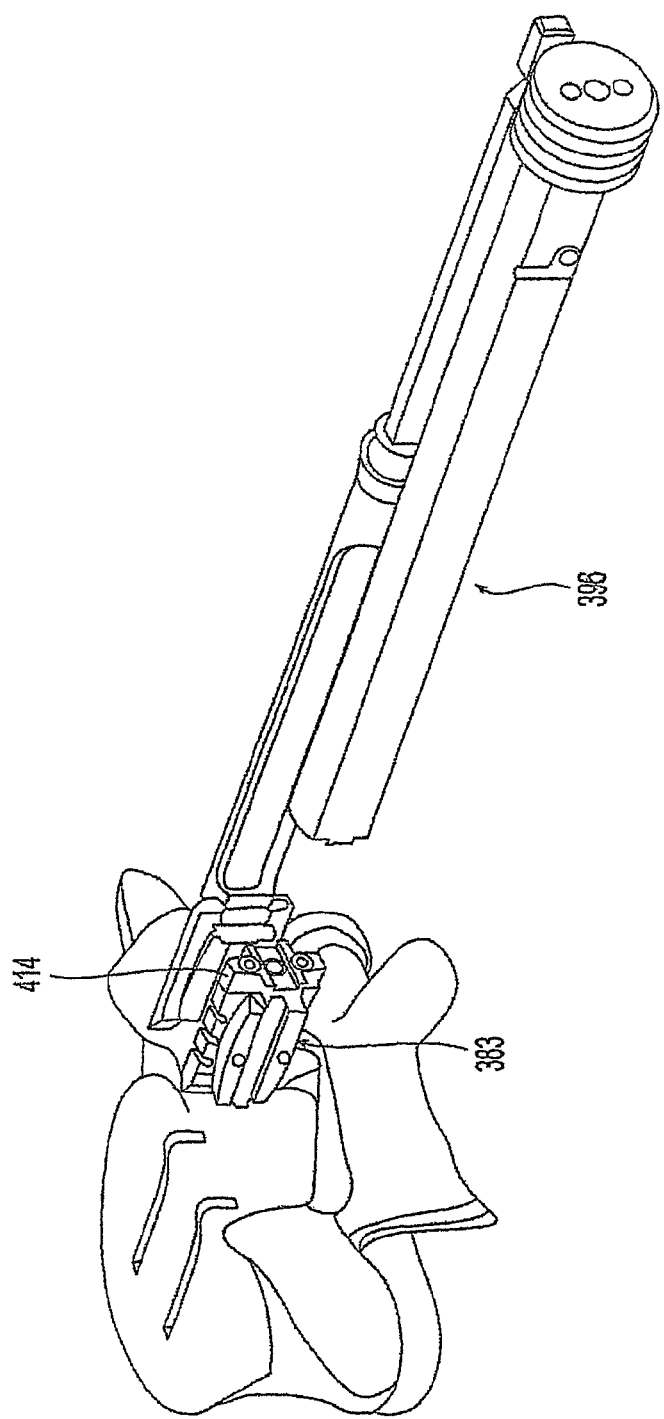

In an embodiment of the present invention, releasing handle 398 from implant holder 392 exposes a proximal end 404 of shaft 396 of implant holder 390. With reference to FIG. 99, shaft 396 of implant holder 390 may be releasably attached to prosthetic disc assembly 383. To release shaft 396 from assembly 383, a surgeon may use a driver 406 as seen in FIG. 99. Driver 406 may be configured with a head 408. Shaft 396 has a first internal rod or elongated screw 410 comprising a threaded end (hidden) and a shaped receiving end 412. As one of skill in the art would understand, head 408 of driver 406 is shaped to mate with receiving end 412 of first internal rod 410 and driver 406 may rotate first internal rod 410, which in turn rotates the threaded end of said rod. Threaded end of rod 410 engages assembly 383, and more particularly, an internally threaded bore hole in a stabilizing member 414 attached to assembly 383. Threaded end of shaft 410 provides the attachment and release mechanism of the implant holder to assembly 383. As one of skill in the art would understand, the attachment can be by any number of different mechanisms. Accordingly, as seen in FIG. 100, shaft 396 is seen released from assembly 383 after assembly 383 has been inserted into the intervertebral space.

Figure 101:
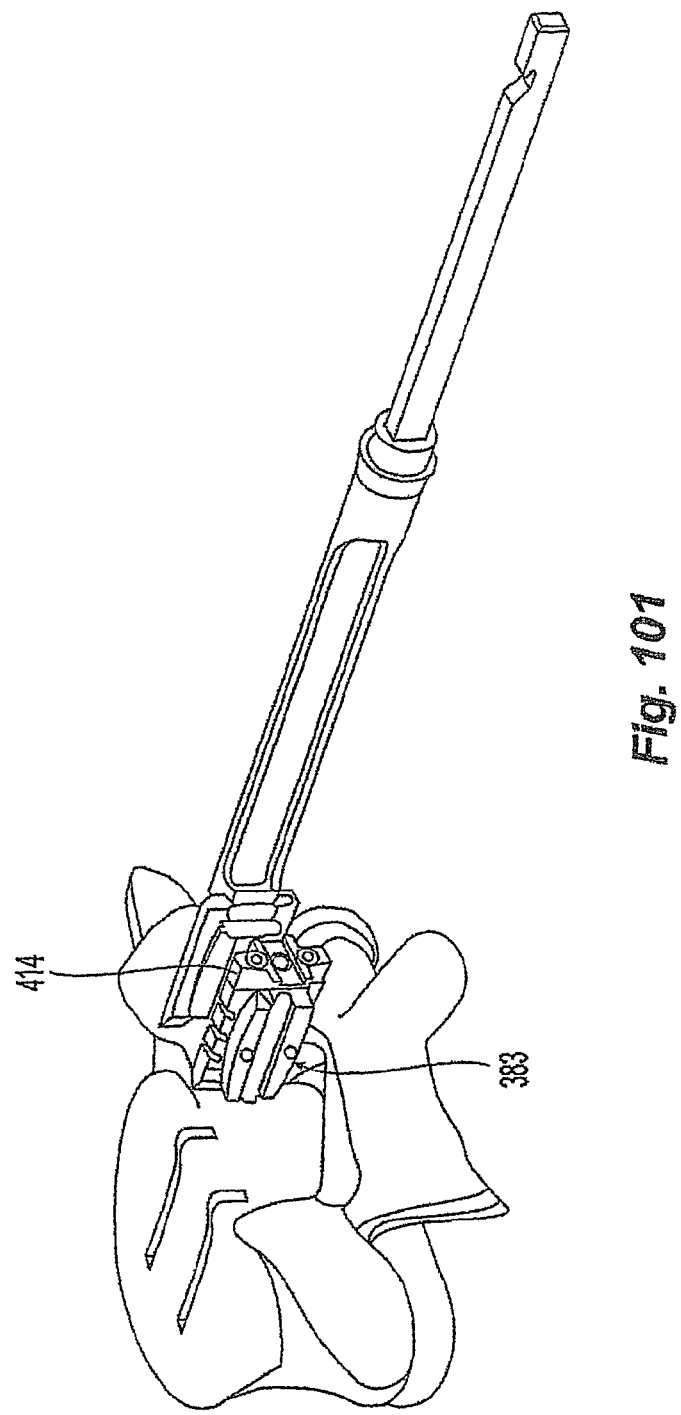

In an embodiment of the present invention, assembly 383 has a stabilizing member 414 attached to assembly 383. With reference to FIG. 101, stabilizing member 4 I4 is shown attached to assembly 383. Stabilizing member 4 I4 is configured to prevent the articulating surfaces of assembly 383 from moving. Stabilizing member 4 I4 is attached to assembly 383 but may disengage or release from the assembly by the surgeon as described in more detail below. Accordingly, during implantation of a two assembly artificial prosthetic disc design, stabilizing member 414 locks the articulating surfaces of assembly 383 until stabilizing member is released.

Figure 102:
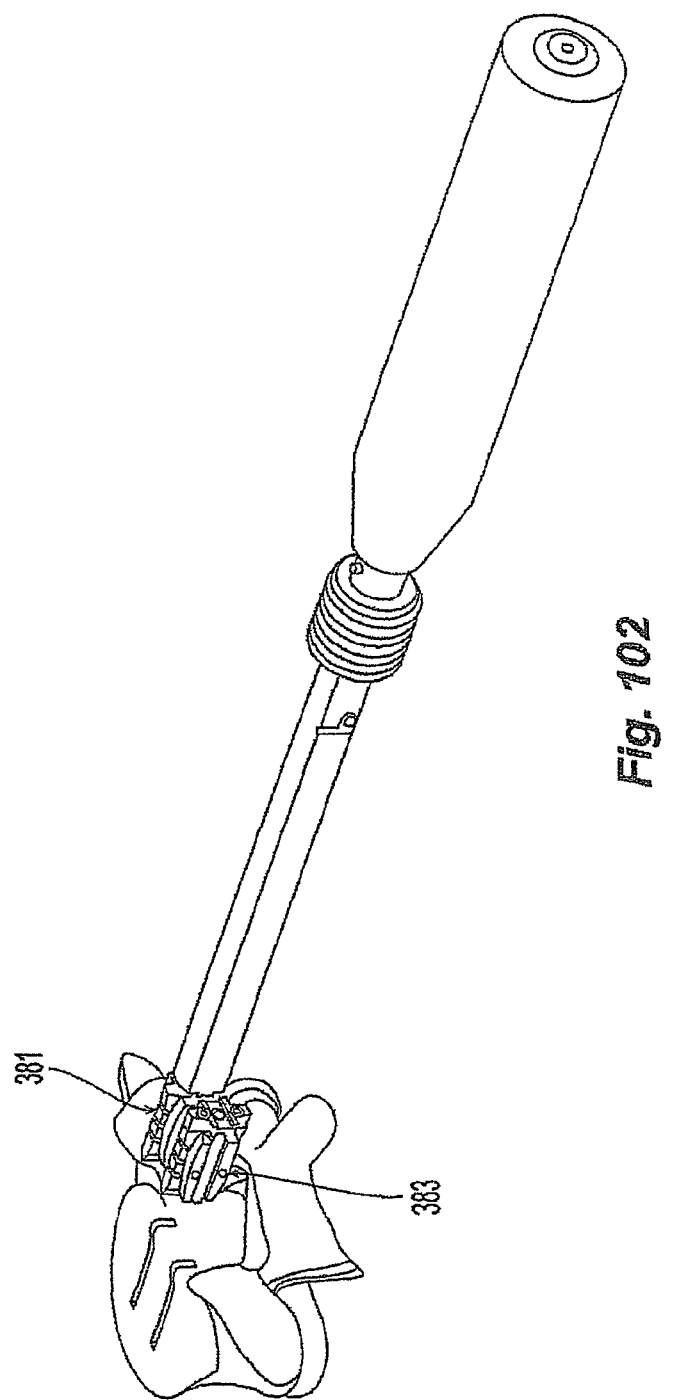
Figure 103:
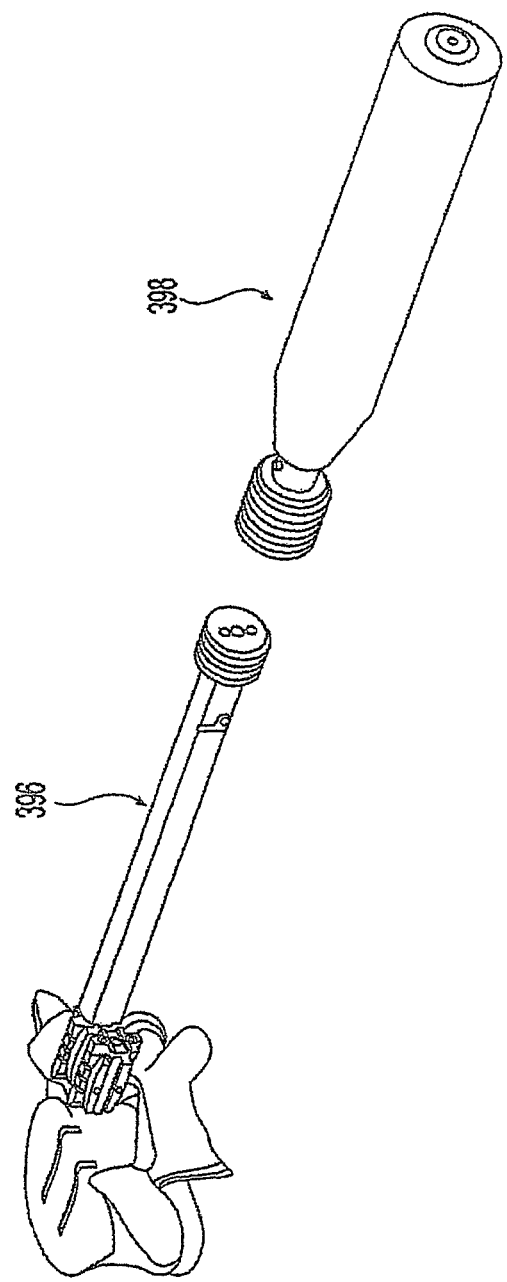
Figure 104:
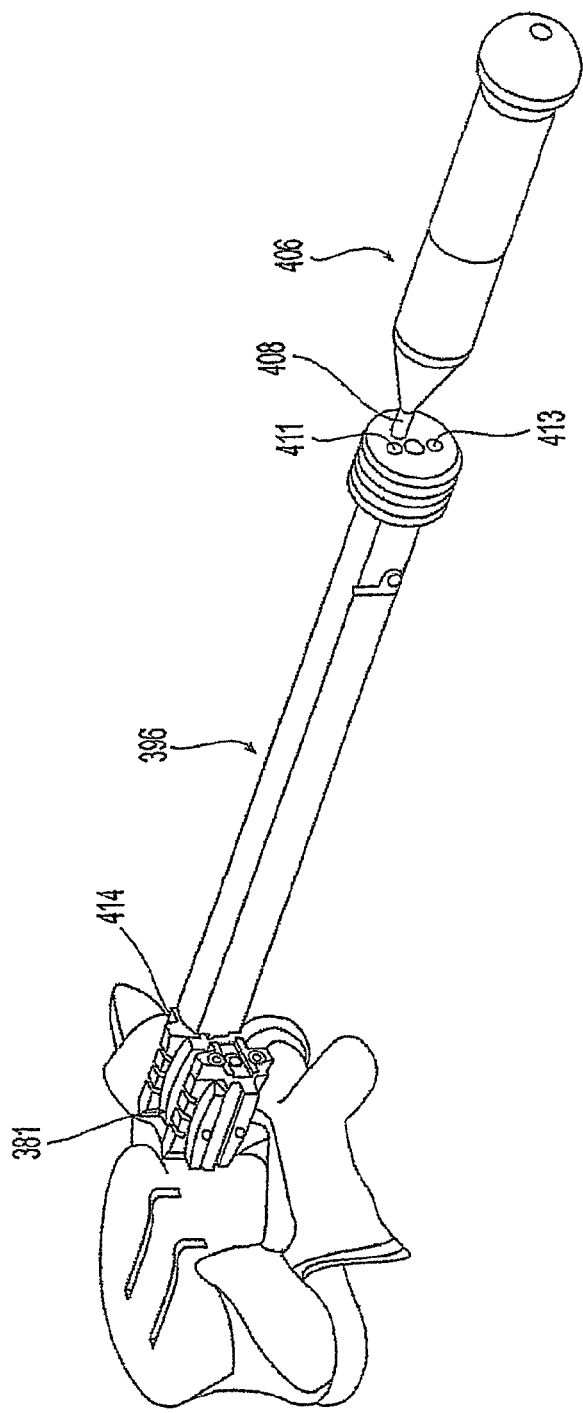

With reference to FIG. 102, after insertion of assembly 383, first trial 305 is removed from the intervertebral space. Second assembly 381 is then inserted using an implant holder as described above and as seen previously except that no guiding member is used in this step. In alternative embodiments, a guiding member may be used if a shaft or other elongated structure is connected to assembly 383. With reference to FIG. 103, handle 398 of implant holder 390 may be separated from shaft portion 396. With reference to FIG. 104, driver 406 may be used to release shaft 396 of implant holder 390 from assembly 381. As seen in both FIGS. 103 and 104, second assembly 381 has a stabilizing member attached. In alternative embodiments, only assembly 383 may have a stabilizing member as stabilizing member 414 attached to first assembly 383 may be sufficient to maintain stability and the need for immobilization of the articulating surfaces of the assemblies may no longer be needed once both assemblies have been implanted. As seen in FIG. 104, shaft 396 has a second internal rod or elongated screw 411 comprising a threaded end (hidden) and a shaped receiving end 413. As one of skill in the art would understand, head 408 of driver 406 is shaped to mate with receiving end 413 of second internal rod 411 and driver 406 may rotate first internal rod 411, which in turn rotates the threaded end of said rod. Threaded end of rod 411 engages a screw in stabilizing member 414, which in turn connects stabilizing member 414 to assembly 381. Threaded end of shaft 411 provides the attachment and release mechanism of the implant holder and stabilizing member 414 to assembly 381. As one of skill in the art would understand, the attachment can be by any number of different mechanisms.

Figure 105:
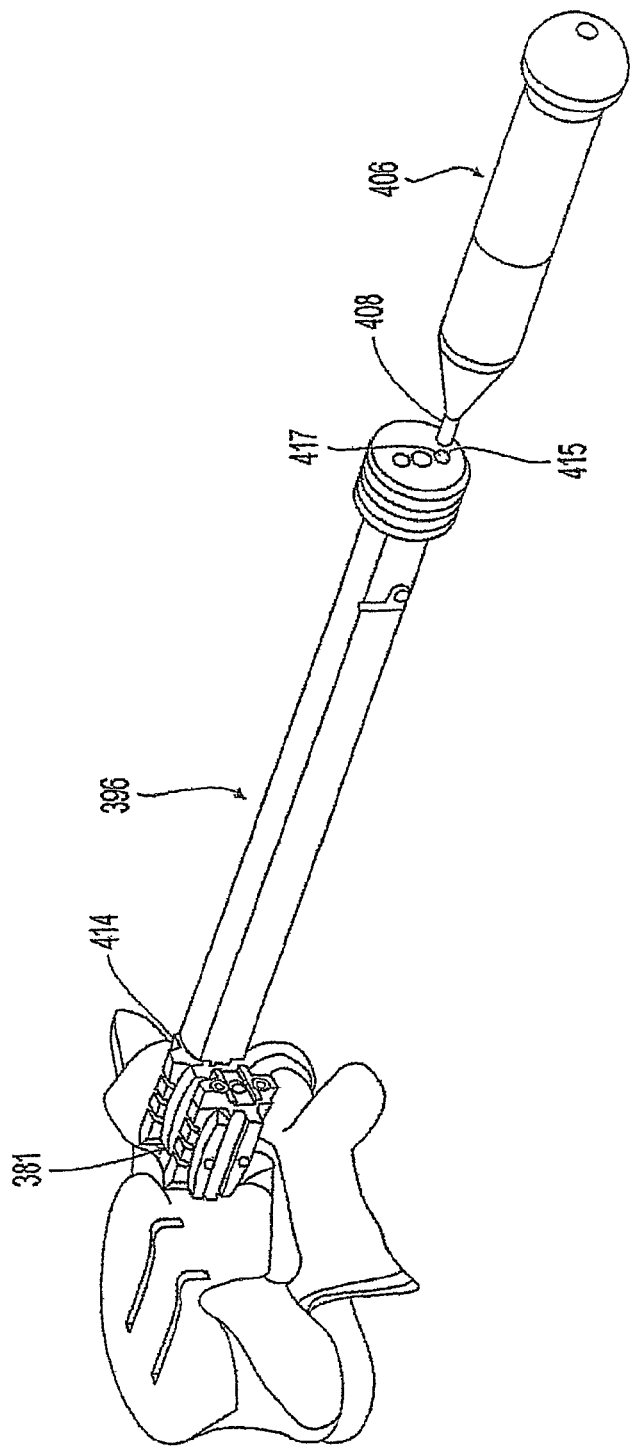

With reference to FIG. 105, shaft 396 may have a third internal rod or elongated screw 415 comprising a threaded end (hidden) and a shaped receiving end 417. As one of skill in the art would understand, head 408 of driver 406 is shaped to mate with receiving end 417 of third internal rod 415 and driver 406 may rotate third internal rod 415, which in turn rotates the threaded end of said rod. Threaded end of rod 415 engages a screw in stabilizing member 414, which in turn connects stabilizing member 414 to assembly 381. Threaded end of shaft 415 provides the attachment and release mechanism of the implant holder and stabilizing member 414 to assembly 381. As one of skill in the art would understand, the attachment can be by any number of different mechanisms.

Figure 106:
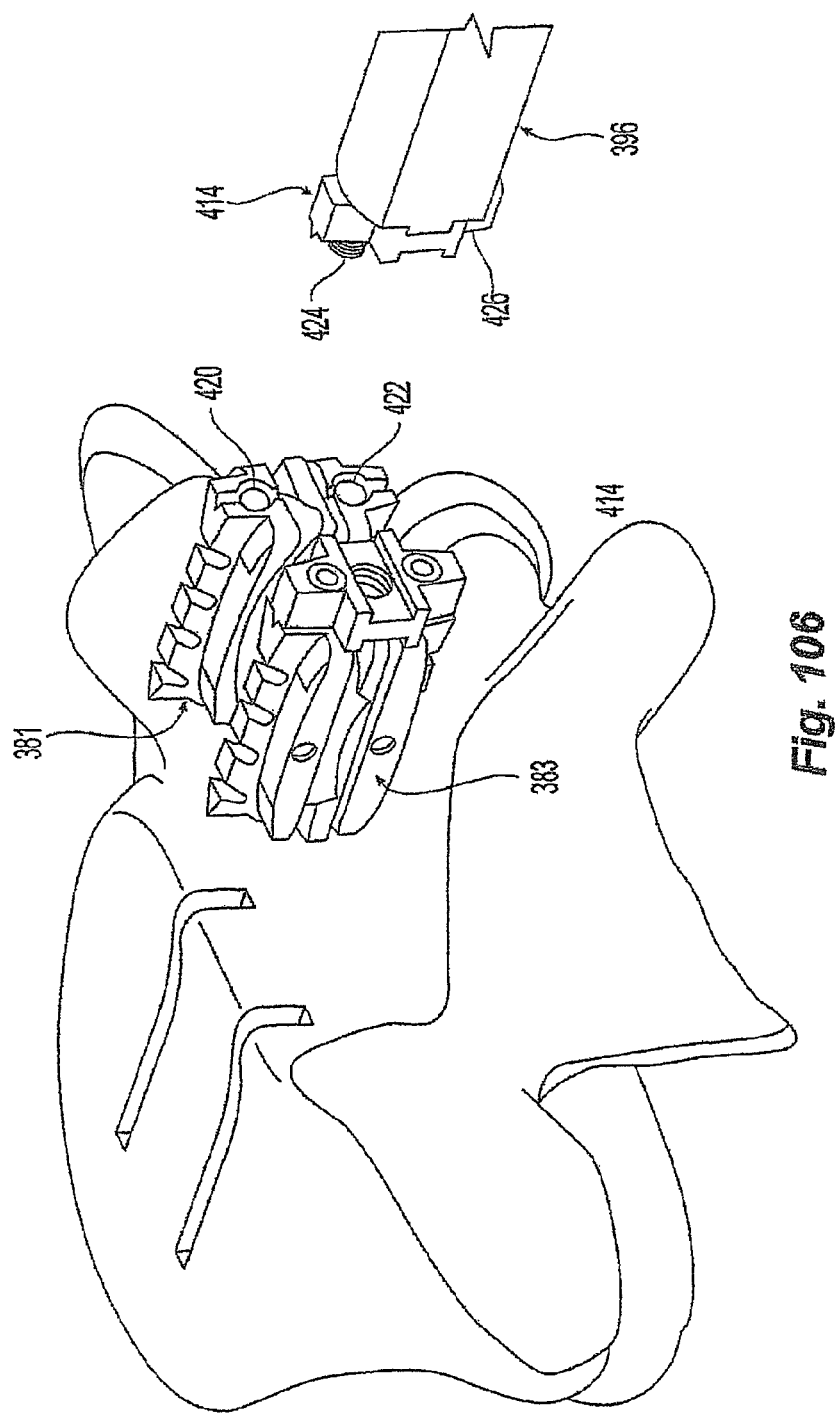

With reference to FIG. 106, assembly 381 is shown implanted into the intervertebral space after shaft 396 of implant holder 390 and stabilizing member 414 has been released. As seen in FIG. 106, threaded bore holes 420 and 422 are configured to interact with screws 424 and 426 (hidden) of stabilizing member 414, said screws having been rotated by the action of driver 408 on rods 41 I and 413 of shaft 396. As further seen in FIG. 106, disc assembly 383 still contains stabilizing member 414 attached to assembly 383.

Figure 107:
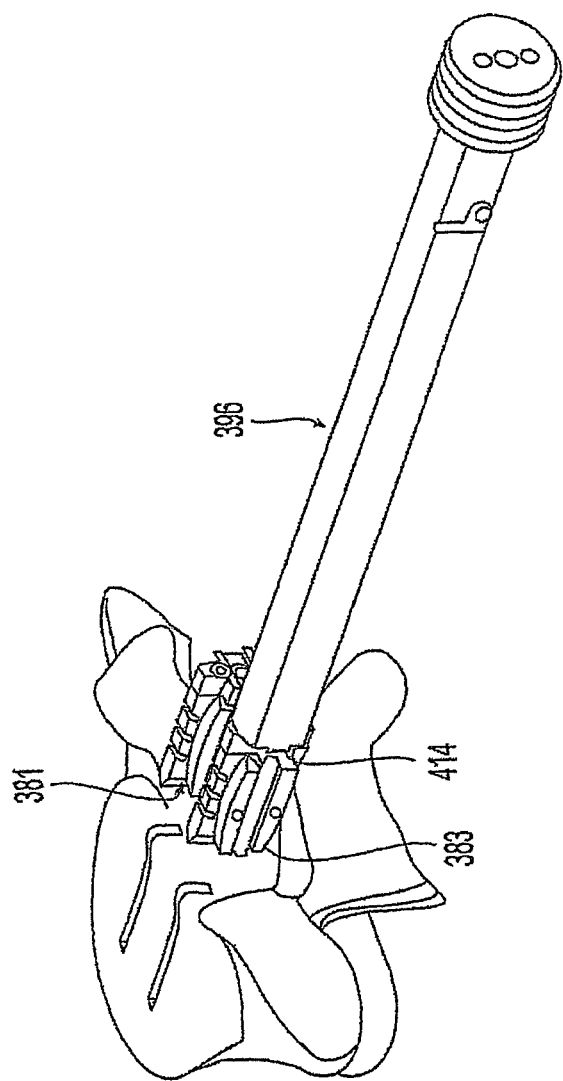
Figure 108:
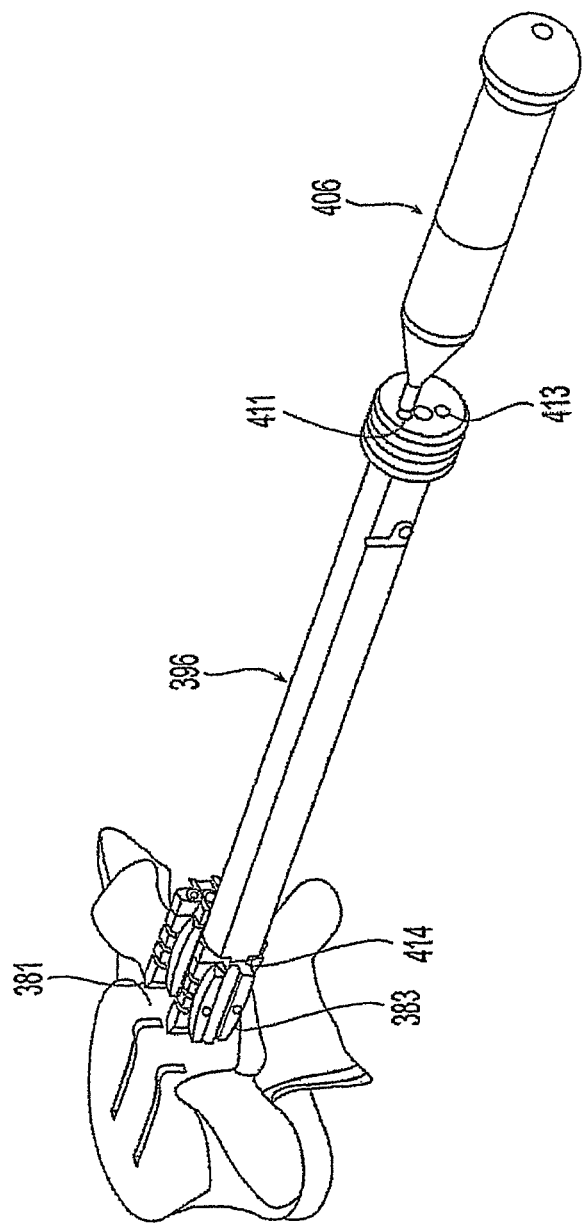
Figure 109:
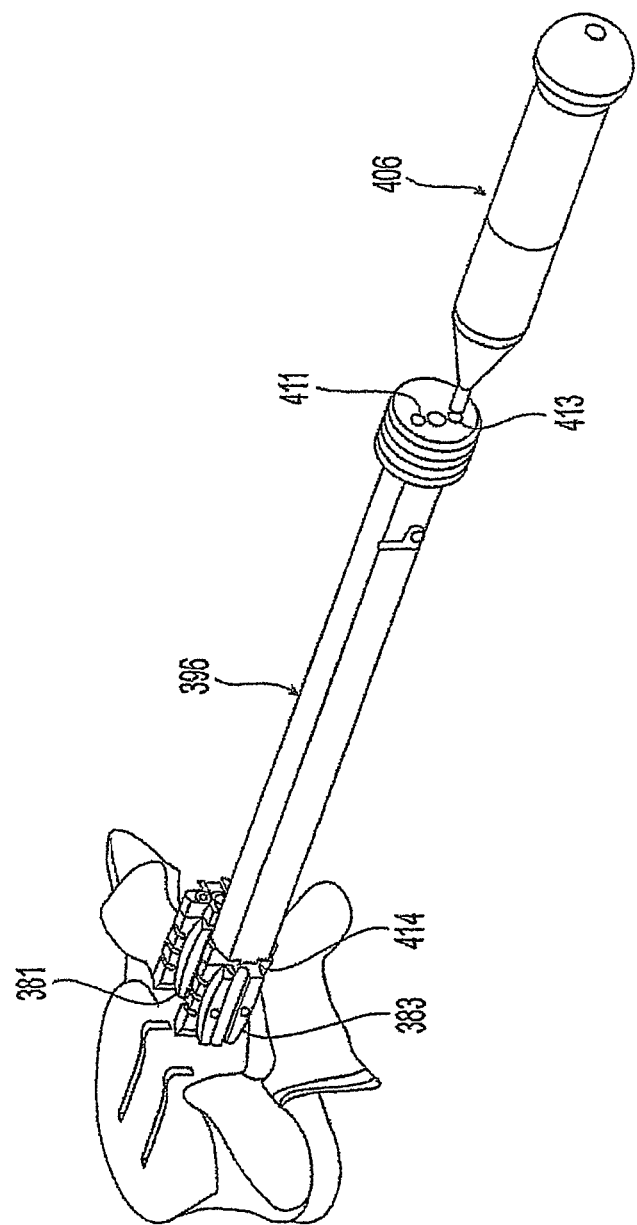

With reference to FIG. 107, stabilizing member 414 of assembly 383 may be released after implantation of assembly 381. As seen in FIG. 107, shaft 396 of implant holder 390 may be reattached to stabilizing member as described above. With reference to FIGS. 108 and 109, driver 406 may then be used to engage mated receiving ends of rotatable internal shafts 411, 413. The opposite ends of rotatable internal shafts (not shown) are configured to engage screws (hidden) in stabilizing member 414, said screws connecting stabilizing member 414 to assembly 383. Accordingly, driver 406 may be used to rotate internal rods 411, 413, which actuate screws in stabilizing member 414 to either attach or release stabilizing member 414 from assembly 383.

Figure 110:
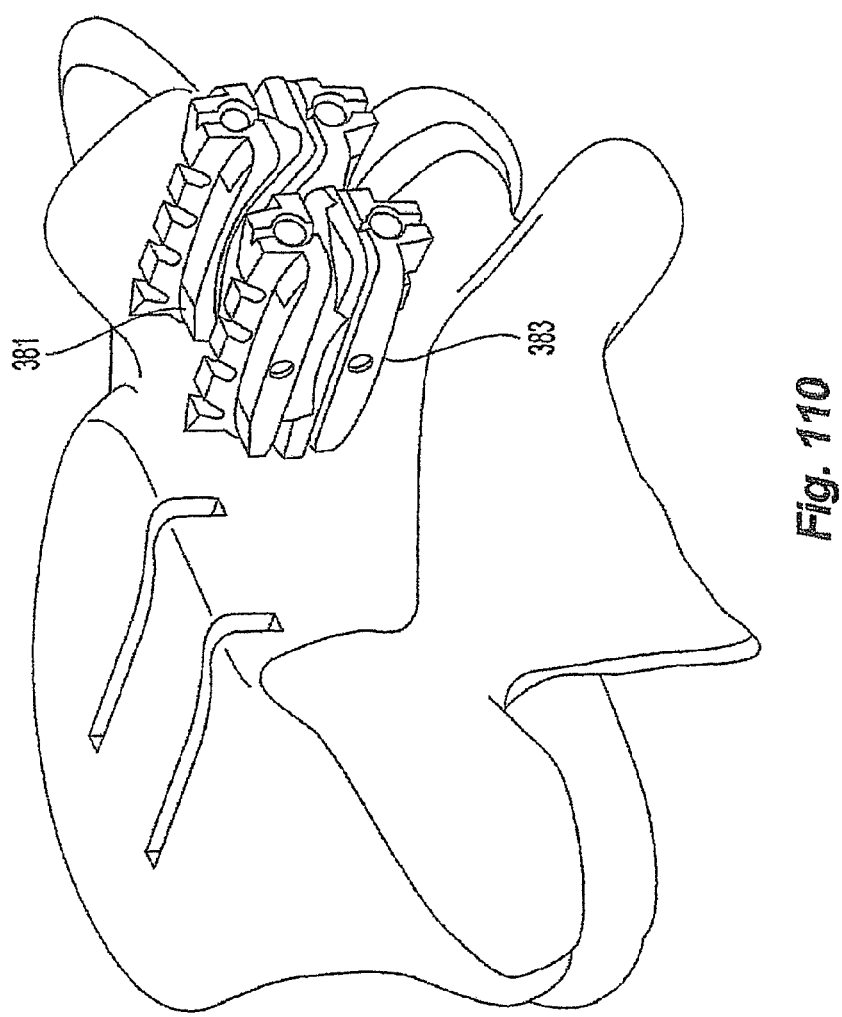

In an embodiment of the present invention, shaft 396 may be connected to stabilizing member 414 through one rod prior to the disengagement of stabilizing member 414 from assembly 396. Accordingly, in an embodiment implant holder connects to stabilizing member via a threaded rotatable rod and stabilizing member connects to an assembly of the prosthetic disc via a screw. In an alternate embodiment, the stabilizing member is connected to the implant holder by more than one rotatable shaft. In an alternate embodiment, the stabilizing member is connected to an assembly of the prosthetic disc by more than one screw. Where the stabilizing member is connected to an assembly by only one screw, locking of the assembly may be accomplished by physical interference of the stabilizing member with the endplates or other structure of the assembly to physically limit rotation of the assembly. Where the stabilizing member is connected to the assembly by more than two screws, the rigidity of the stabilizing member locks the assembly in place. As stabilizing member is used to lock or prevent articulation of the first assembly implanted into the intervertebral space, any number of mechanisms may be used to prevent said articulation or movement. Accordingly one of skill in the art that screws, interference fits, prongs, tabs, or other configurations can be used on the stabilizing member to prevent articulation of the assembly. With reference to FIG. 110, assemblies 381 and 383 are shown in their final position (offset).

Figure 111:
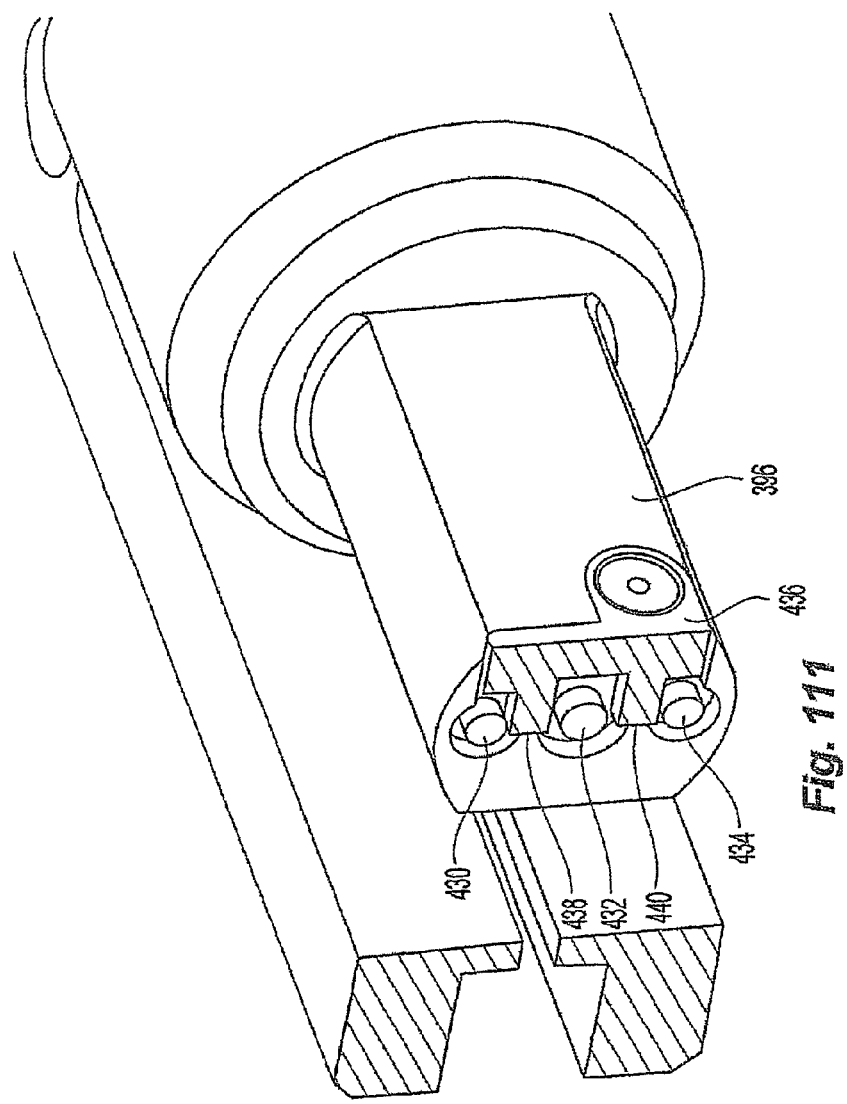

With reference to FIG. 111, a cross section of shaft 396 of implant holder 390 is shown. As seen in FIG. 111, in this embodiment, there are three elongated rods 430, 432, and 434 that act to either connect stabilizing member to shaft 396 or stabilizing member to an assembly. As revealed by the cross section view of shaft 396, the elongated rods may be configured to allow longitudinal movement within the shaft. This movement allows the shafts to individually engage either the threaded bore or screws of the stabilizing member and further allows for proper threading or mating between the end of an elongated shaft and its mating portion. Elongated shafts 430, 432, and 434 may be retained within the shaft and provided a limited range of movement by using retaining clip 436. As one of skill in the art would understand, elongated shafts 430, 432, and 434 may be formed with a portion having a smaller diameter than the rest of the shafts. Clip 436 may then be formed with two arms 438 and 440, which may contact or abut inner walls of the elongated rod but otherwise not contact or interfere with the elongated rod. In this manner, depending on the length of the portions of the rod having a smaller diameter, the elongated rods may translate within the shaft. The length of translation may vary but in an embodiment of the present invention, the elongated rods may translate between about 1 mm and 4 mm.

As described above, methods and tools are provided that allow a surgeon to implant a prosthetic disc from the posterior approach. The methods allow a surgeon to implant more than one assembly, which may have articulating surfaces. In general, the methods provide a means by which the surgeon can properly align each prosthetic disc with respect to each other. In operation, the methods also generally minimize distraction and injury to the spinal cord.

Figure 112:
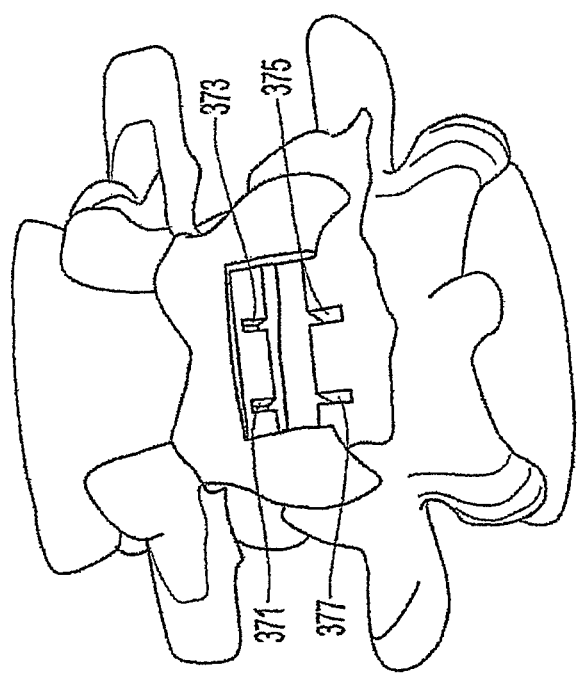
FIG. 112 illustrates an intervertebral disc space in which paths have been cut in vertebral bodies using the methods of the present invention.

In an alternative embodiment, after cutting both pathways or grooves, the second chisel, first chisel, attaching member, and trial may be removed. Referring to FIG. I 12, the intervertebral disc space is shown after it has been prepared by the methods and tools of an embodiment of the present invention. As seen in FIG. 112, four separate pathways 371, 373, 375, 377 have been cut into the surfaces of the vertebral bodies. As one of skill in the art would understand, the paths cut by the methods and tools of the present invention provide spaces for the insertion of keels spaced apart by a predetermined distance. Moreover, each pathway is generally cut parallel to each other. The upper and lower paths are aligned within the same plane. As one of skill in the art would understand, the present methods and tools provide a surgeon with the ability to insert multiple assemblies into the intervertebral space from a posterior approach.

Figure 113:
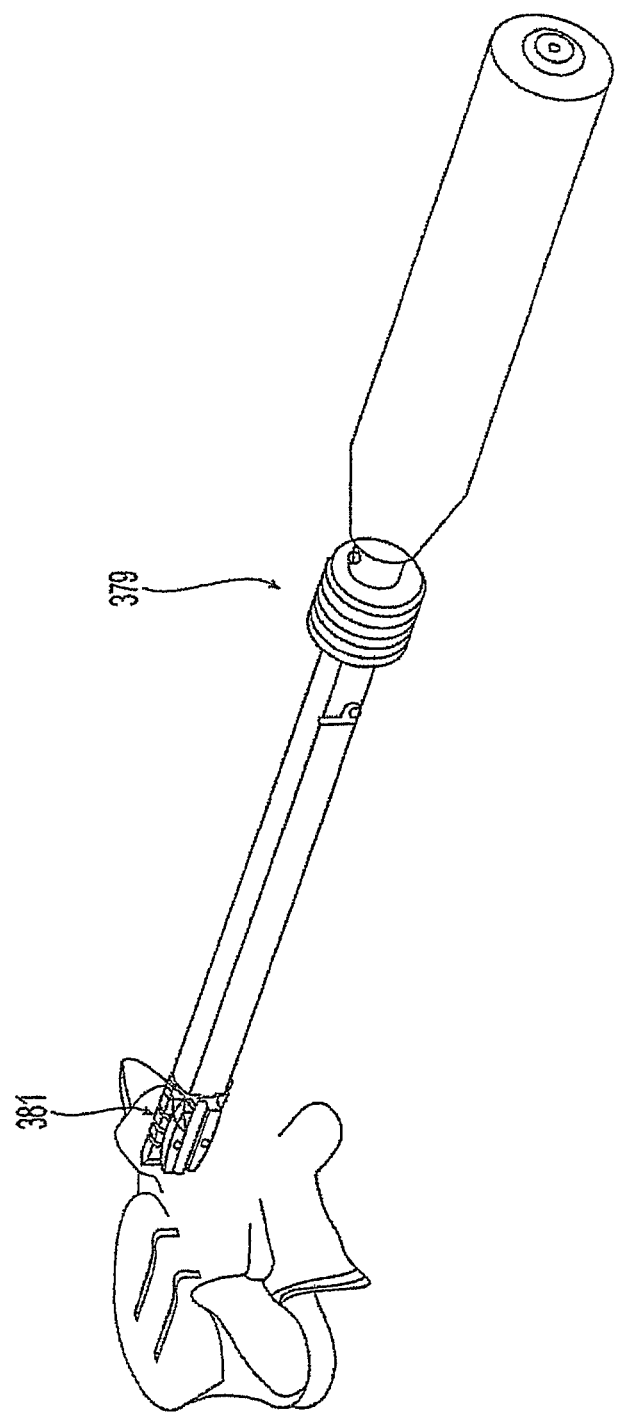
FIGS. 113-116 illustrate various tools used in an embodiment of the methods of the present invention.

According to one embodiment of a method of the present invention, after removing the chisels and trial, an assembly may be inserted into the intervertebral space. Referring to FIG. 113, a disc holder 379 is shown attached to a prosthetic disc assembly 381 according to the present invention. Preferably, disc holder 379 maintains assembly 381 in a neutral position. Disc holder 379 may be of any variety of designs and the methods of the present invention are not limited to any particular disc holders. As one of skill in the art would understand, disc holder is used to insert assembly 381 into the intervertebral space. In one embodiment, a first prosthetic disc 381 has an upper and lower keel that rides within the paths cut by the first chisel.

Figure 114:
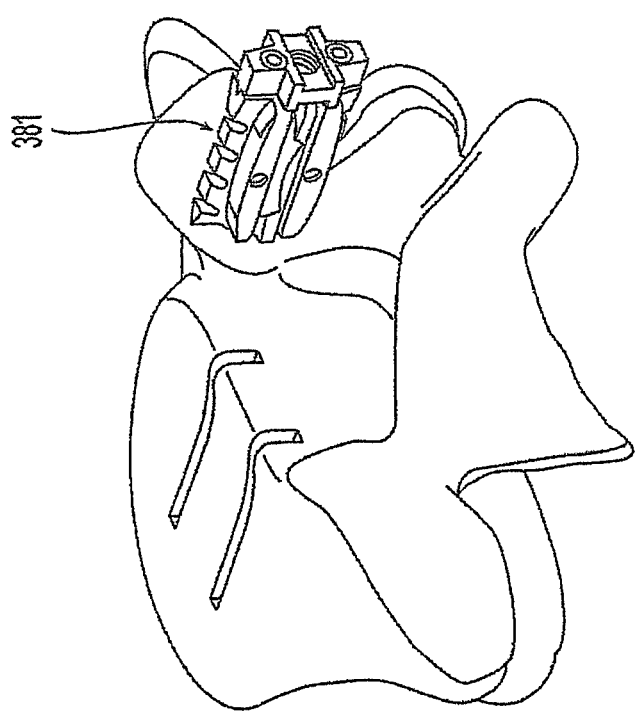
Figure 115:
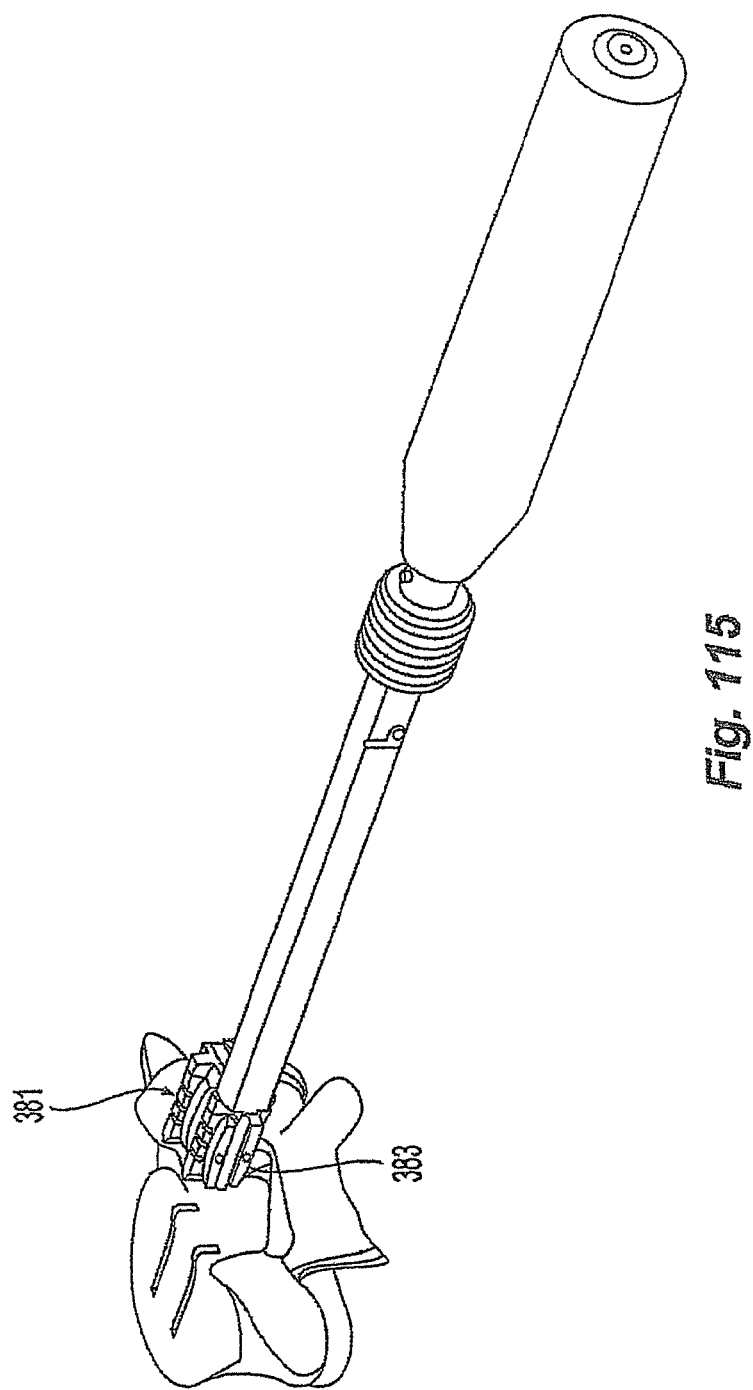
Figure 116:
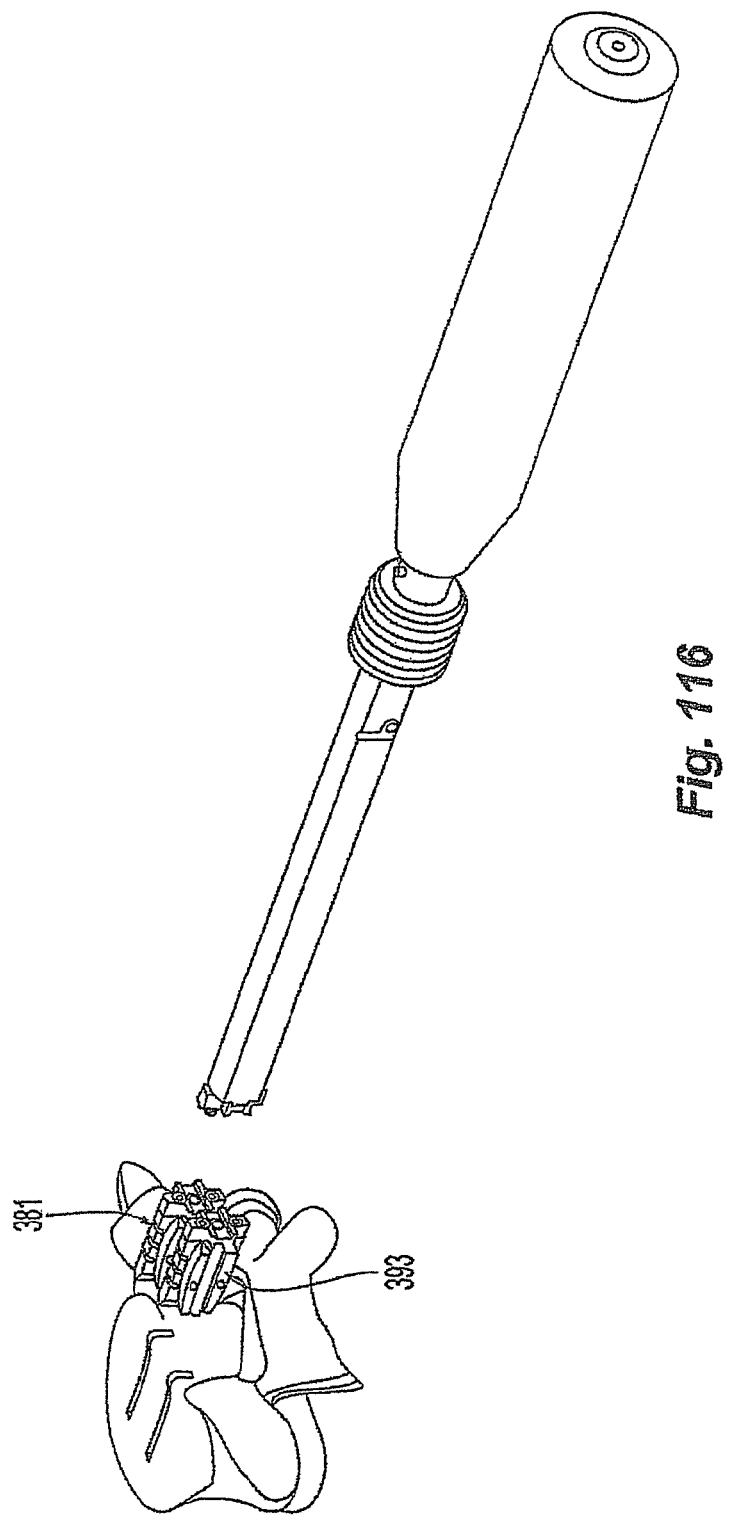
Figure 117:
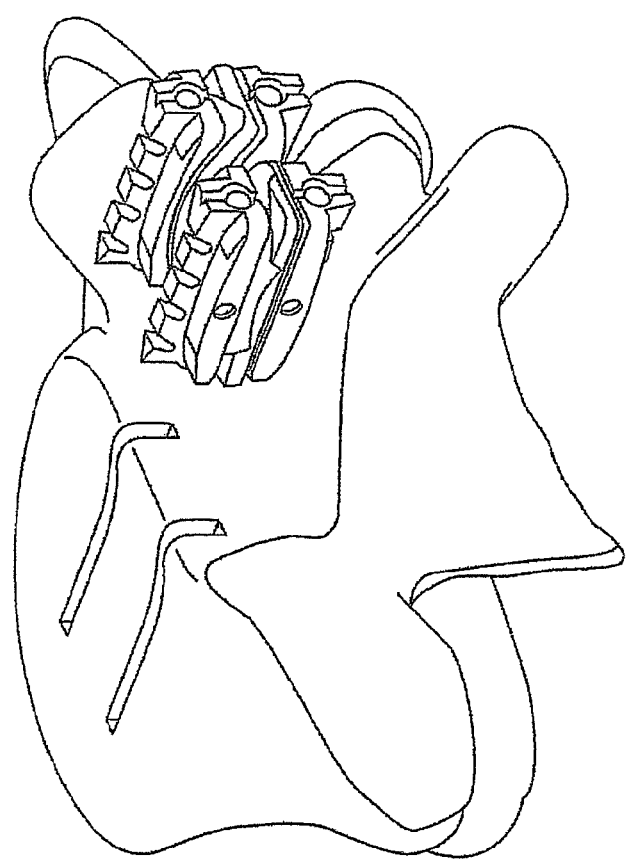
FIGS. 117-118 illustrate prosthetic disc assemblies after implantation according to the methods of the present invention.
Figure 118:
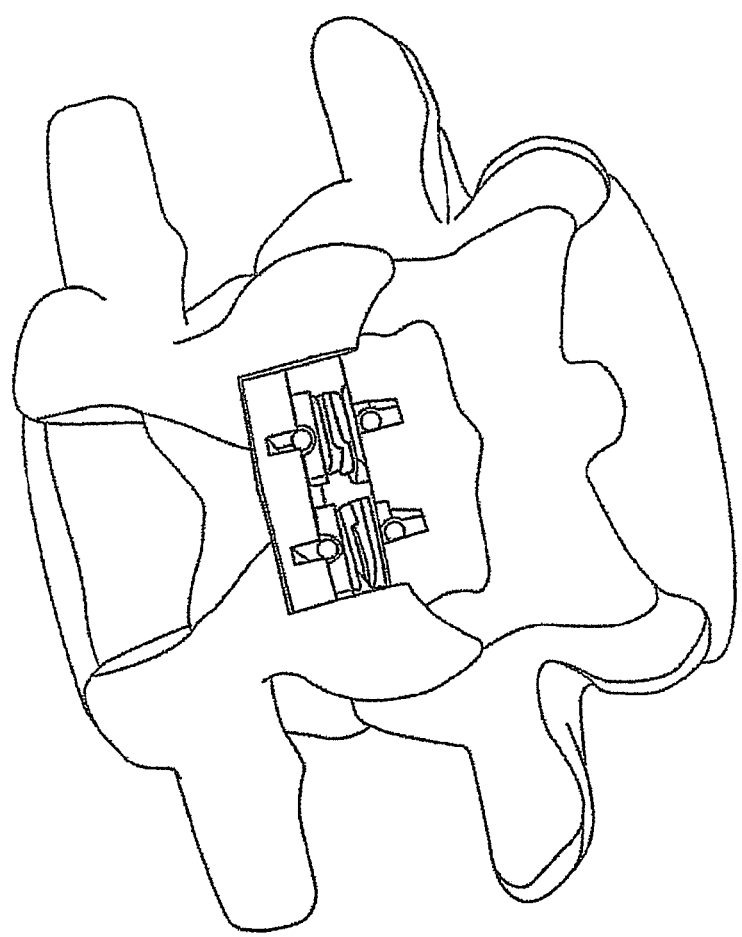

Once the first disc assembly is inserted, the disc holder may release the first prosthetic disc. As seen in FIG. 114, the disc holder has released assembly 381 and assembly 381 is shown in its final or implanted position in the intervertebral space. Referring to FIG. 115, the upper vertebral body is not shown for sake of clarity. Next, the second assembly may be inserted. As seen in FIG. 115, a second assembly 383 is inserted into the intervertebral space. The upper and lower keels of the second assembly ride within the paths cut by the second chisel. Once inserted, the disc holder releases the second assembly (FIG. 116). FIGS. 117 and 118 show the two assemblies inserted into the disc space. The prosthetic disc assemblies are shown in their neutral position. As one of skill in the art would understand, after implantation the spacing between the assemblies is such that the endplates of the assemblies can articulate as if they were a single articulating surface.

Figure 119:
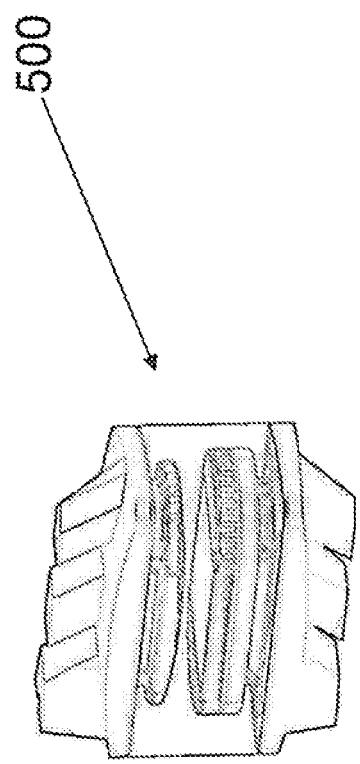
FIG. 119 illustrates yet another embodiment of the prosthetic disc assembly according to the present invention.
Figure 120:
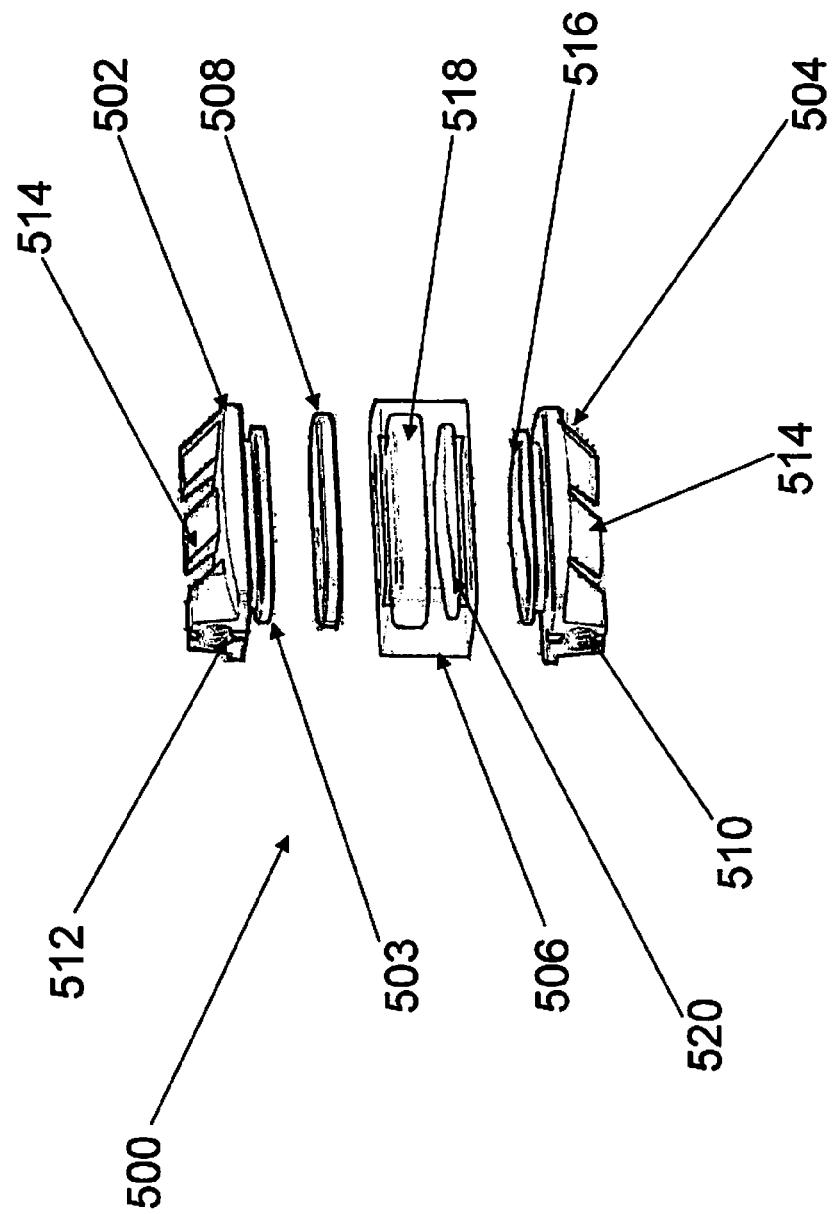
FIG. 120 illustrates an exploded view of the of the prosthetic disc assembly according to the present invention.

Now, turning to FIG. 119, another embodiment of a posterior disc assembly is illustrated. In this particular embodiment a posterior spinal disc 500 which contains multiple elements according to the present invention is shown. FIG. 120 illustrates an exploded view of the disc assembly 500, which more clearly shows the individual elements of the spinal disc 500. FIG. 120 illustrates an upper endplate 502, a lower endplate 504, a flexible core element 506 and a slider plate 508. The endplates 502, 504, flexible core element 506, and the slider plate 508 may be composed of a variety of biocompatiable materials, including metals, ceramic materials and polymers. Such materials include, but are not limited to, aluminum, alloys, and polyethylene. The outer surfaces of the endplates 502, 504 may also contain a plurality of teeth which may be maybe coated with osteoconductive material, antibiotics or other medicament, or may have a porous or macrotexture surface to help rigidly attach the endplates 502, 504 to the vertebral bodies by promoting the formation of new bony ingrowth. Each of these elements and the interconnections between the associated elements will be discussed in greater detail with reference to FIGS. 121-126.

In the present embodiment, the upper endplate 502 is configured with a plurality of keels 514 that engage with an interverterbral body and an extension portion 503 which is configured to be in contact with the slider plate 508. The extension portion 503 is configured with a curvature which corresponds with a curvature associated with the slider plate 508. The extension portion 503 and the plate 508 being in communications allows rotational and translational motion to occur. As mentioned previously, the present disc assembly can mimic or partially mimic the varying IAR and COR to the extent desired by a physician while also preserving the stability of the device.

Although the present embodiment utilizes a keel 514 so that it may be used to guide the disc assembly into position during insertion into the treated area of the spine, ridges, teeth or any other type of mechanism to attach the endplate 502, 504 to the vertebral body may also be used. Also, as mentioned previously, the use of one or more keels 514 may also increase bone to implant surface contact, thereby decreasing the likelihood that the assembly will shift or move out of position.

The extension portion 503 of the upper endplate 502 is spaced apart from the base of the upper endplate 502 and fits into a cavity 518 in an upper portion of the flexible core element 506. The extension portion 503, in the present embodiment, is provided with a flat surface having a length of 17 mm, a width of 7 mm and a height of 2.5 mm. However, in other embodiments the contact surface of the extension portion 503 may be configured with a curvature or dimensioned for optimizing the contact surface. Although in the present embodiment, the extension portion 503 of the upper endplate 502 is configured with a flat surface, any geometry may be used that adapts within the flexible core element 506 and communicates with the slider plate 508. The lower endplate 504 is also configured with multiple keels 514 to engage with an adjacent vertebral body. The lower endplate 504 is also configured with an extension portion 516 which is adapted to fit within a cavity in a lower portion of the flexible core element 506. The extension portion 516 is spaced apart from the base of the lower endplate 504 and is configured to conform to the cavity formed in the lower portion of the flexible core element 506. In this embodiment, the extension portion 516 is configured as an elongated and curved plate having a length of 17 mm, a width of 7 mm and a height of 1.5 mm. It should be noted that the extension portion 516 may be configured to be in any geometry to conform and fit within the cavity formed within the lower portion of the flexible core element 506. The upper endplate 502 and the lower endplate 504 are also provided with screw holes 512, 514 for receiving an instrument for positioning the disc 500 within the intervertebral space.

The flexible core element 506 is composed of a flexible material that may be tensioned, compressed or be a combination of tensioned and compressed elements. The flexible core element 506 may be made of resilient material that provides suitable resistance to stretching or compression. The compression element helps support axial loading along the treated vertebral bodies so their relative positions approximate a healthy vertebral body supported by a natural disc. The flexible core element 506 also helps in controlling the bending or movement of the vertebral bodies relative to each other. The flexible core element 506 is configured and adapted to allow for compression and translation by providing a cavity in the upper portion and a cavity in the lower portion which receives the extension portions of the upper 502 and lower endplates 504. The flexible core element 506 is composed of a resilient material to allow for rotation to occur.

The flexible material in one particular embodiment is composed of Polycarbonate Urethane. However, any flexible material that is No-mechanical and biologically compatible may be used. As mentioned above, the core element 506 has an upper portion and a lower portion. The upper portion is configured to receive and retain the slider plate 508 within the cavity 518. The lower portion is configured to receive and retain the extension portion 516 of the lower endplate 504 within the cavity 520.

The slider plate 508 is a metal plate having an upper and lower surface. The upper surface of the slider plate 508 is generally a flat surface however a curvature that corresponds to the curvature of the extension portion 503 of the upper endplate 502 may also be utilized. Additionally, the slider plate may be configured to be of any geometric shape which is capable of communicating with an extension portion of the upper endplate. In the preferred embodiment the slider plate 508 is composed of metal, however the slider plate 508 may be comprised of any element that allows a friction coefficient that enables the extension portion 503 translate or axially rotate relative to the slider plate 508.

Figure 121:
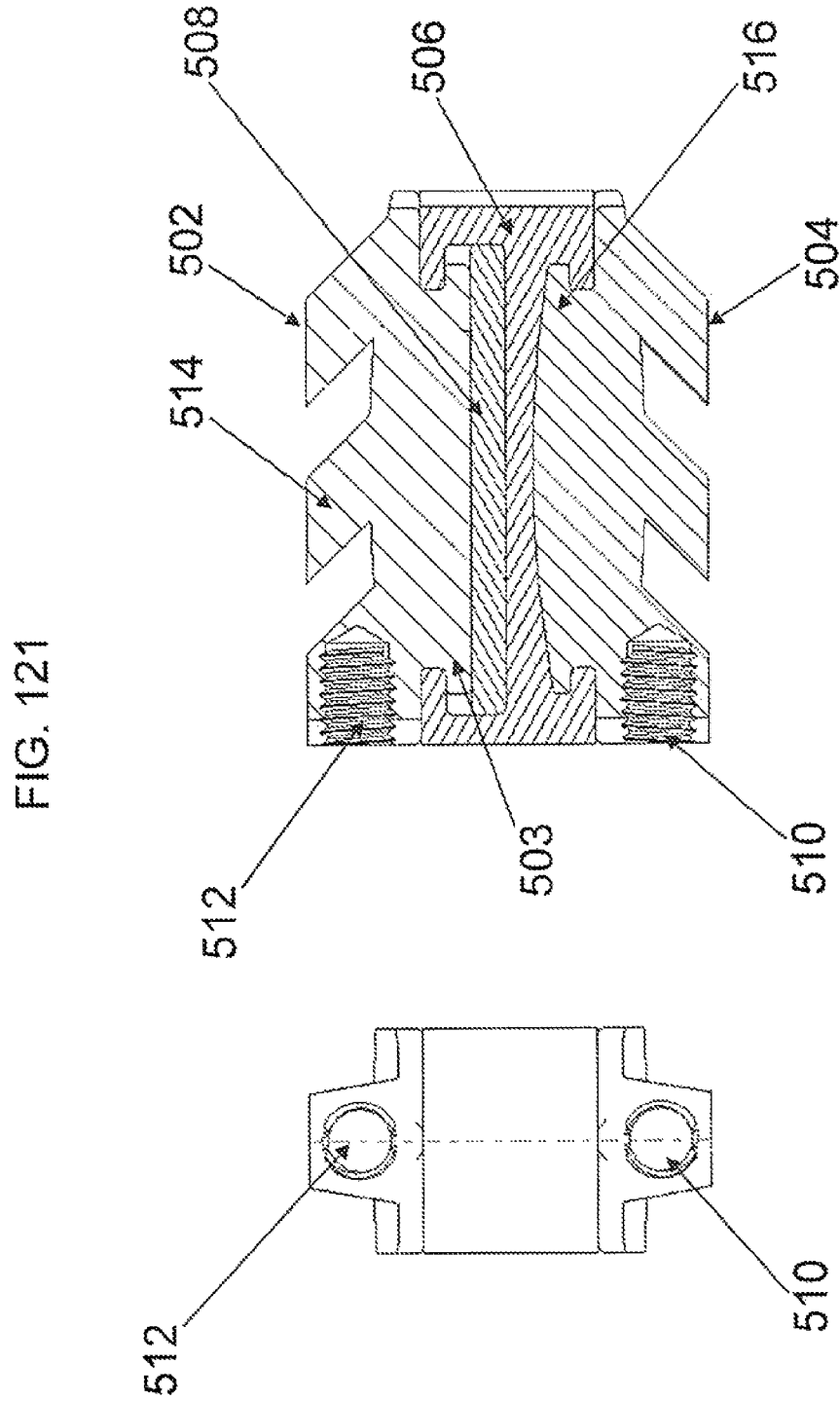
FIG. 121 a illustrates cross sectional views of the prosthetic disc assembly according to the present invention.

FIG. 121 illustrates a cross sectional view of one particular embodiment of the disc assembly 500. In this embodiment of the disc assembly 500, the upper endplate 502 is in communication with the slider plate 508 through the extension portion 503. The extension portion 503 is adapted into the flexible core member 506. The extension portion 503 is slightly smaller than the space provided between one end of the flexible core element 506 to the other end. As a result, the extension portion 503 may translate from 0.5 mm to 1 mm along the slider plate 408. Additionally, the upper endplate 502 may translate and axially rotate relative to the flexible core element 506. Thus, the upper endplate 502 can translate in one direction or in a second direction by configuring the extension portion 503 to communicate with the slider plate 508.

The lower endplate 504 is also provided with an extension portion 516 that is fitted into the flexible core element 506. In this particular embodiment, the lower endplate 504 is adapted to fit tightly within the flexible core element 506 to limit the translational and axial motion of the lower endplate 504 with respect to the flexible core element 506. However, the lower endplate 504 is adapted to extend and flex within the flexible core element 506, as the flexible core element 506 is compressed or stretched. In this embodiment, the length, height, and width of the cavity in the lower portion of the flexible core element 506 is substantially equal to the length, height, and width of the extension portion 516 of the lower endplate 504, thereby limiting translational and rotational motion. As explained above, the lower endplate 504 is configured to compress and flex on the flexible core element 506, providing flexion and extension. The upper and lower endplates 502 and 504 are also provided with screw holes 510, 512 for receiving an instrument which is utilized to position the disc assembly within the intervertebral space of the spine. The upper and lower endplates 502 and 504 are also configured with a base portion that have a spherical contact surface which increases the surface area for contacting with the adjacent vertebral body.

Figure 122:
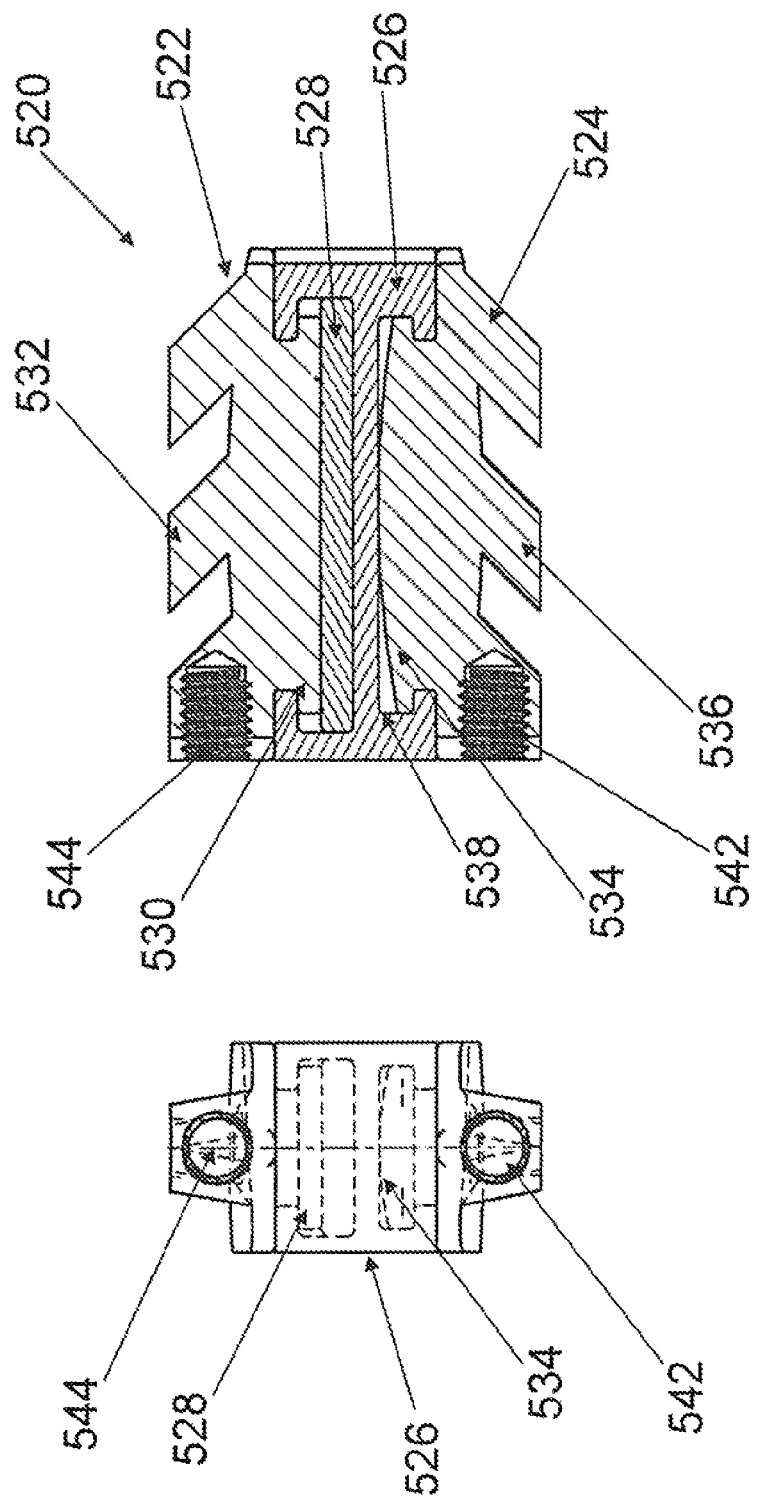
FIG. 122 illustrates a cross sectional view of another embodiment of the prosthetic disc assembly according to the present invention.

FIG. 122 illustrates a cross-sectional view of another embodiment of a disc assembly 520 according to the present invention. In this particular embodiment, the disc assembly 520 is comprised of an upper endplate 522, a lower endplate 524, a flexible core element 526 and a slider plate 528. The extension portion 530 of the upper endplate 522 is adapted to fit within a cavity in an upper portion of the flexible core element 526. The extension portion 530 of the lower endplate 524 is adapted to fit within a cavity in the lower portion of the flexible core element 526. The flat surface of the extension portion 534 of the lower endplate 524 is configured with a curvature for enabling flexion and extension with respect to the flexible core element 526. As illustrated in FIG. 122, the cavity 538 in lower portion of the flexible core element 526 is larger than the extension portion 534 of the lower endplate 524, which allows greater amount of flexion and extension to occur when the flexible core element 526 is either compressed or stretched.

The slider plate 528 allows for axial rotation and translation (anterior/posterior sliding motion) within the device. Flexion, extension and lateral bending motions are a hybrid combination of movement available due to the spherical feature provided on the inside of the endplate 522, that mates to the flexible core element 426. As in the previous embodiments, the upper and lower endplates 522, 524 are provided with multiple keels 532, 536 to attach the endplates 522, 524 to adjacent vertebral bodies. The disc assembly 520 is also provided with threaded holes 542, 544 on the posterior faces of the endplates 522, 524 for receiving an instrument which is used to position the disc assembly within the disc space of the spine. A locating groove that helps to align the screw holes as well as resist twisting forces while being inserted is also provided on the posterior portion of the disc assembly.

Figure 123:
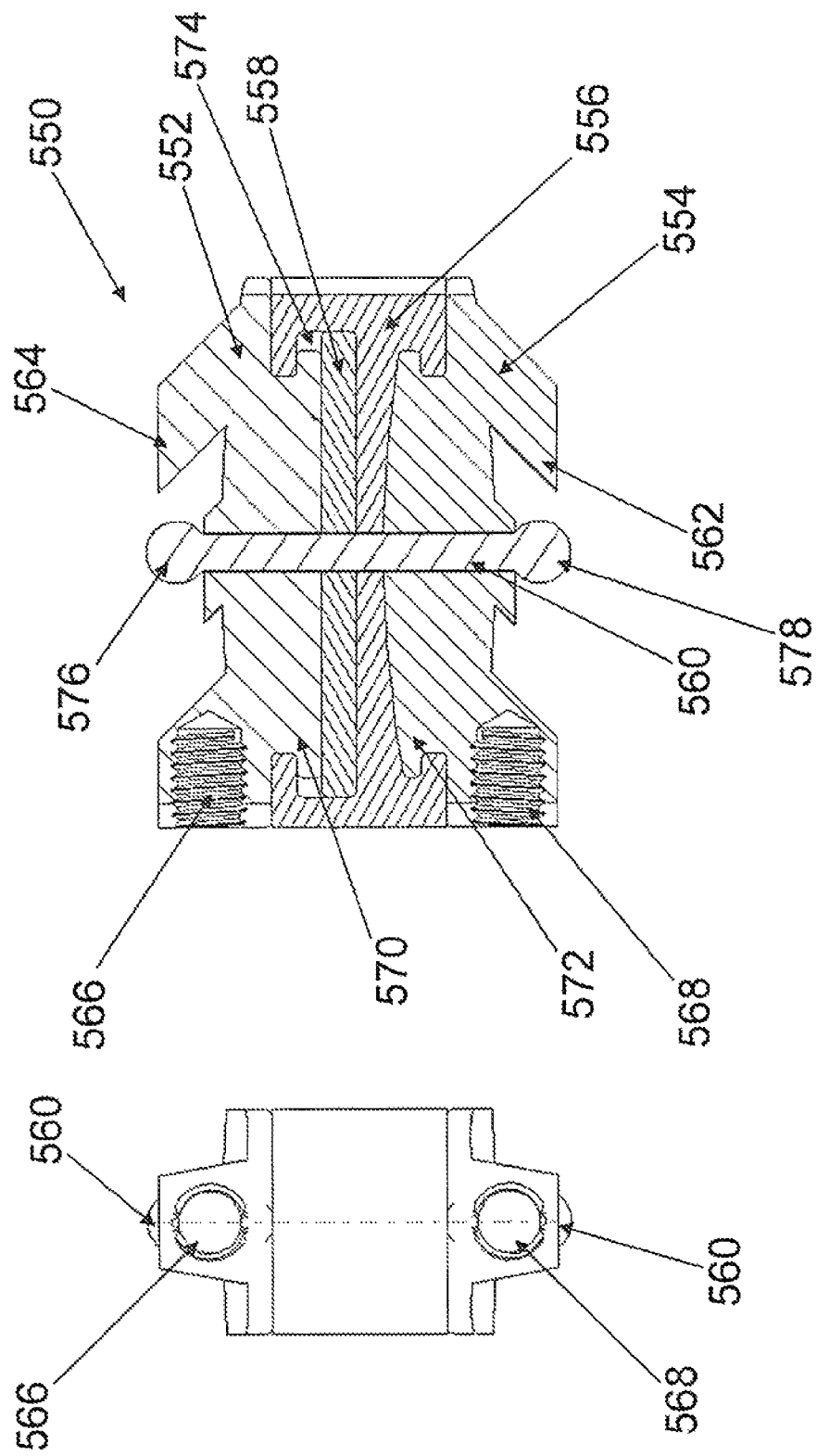
FIG. 123 illustrates a cross sectional views of yet another embodiment of the prosthetic disc assembly according to the present invention.

FIG. 123 illustrates yet another embodiment of the invention. In this embodiment, the disc assembly 550 is comprised of an upper endplate 552, a lower endplate 554, a flexible core element 556, a slider plate 558, and cord 560.

The upper endplate 552 and lower endplates 554 are configured with keels 562, 564 which engage with the corresponding adjacent vertebral bodies. The upper and lower endplates 552 and 554 are also provided with threaded screw holes 566, 568 on the posterior faces of the upper and lower endplates 552, 554 for receiving an instrument to position the disc assembly within the spine.

The disc assembly 550 further includes the flexible core element 556 which is situated between the upper and lower endplates 552, 554. The inner portion of the flexible core element 556 is configured with a cavity in the upper portion that receives and retains the slider plate 558 and the extension portion 570 of the upper endplate 552. The lower portion of the flexible core element 556 is also configured with a cavity which receives and retains the extension portion 572 of the lower endplate 554. The extension portion 570 of the upper endplate 552 is adapted to communicate with the slider plate 558 to allow for translation since the extension portion 570 is slightly smaller in length than the slider plate 558. The extension portion of the upper endplate is configured to be slightly smaller than the slider plate 558 and fits within a first cavity in the inner portion of flexible core member, allowing for some space between the edges of the extension portion and the edge of the inner portion. The upper endplate is translated or rotated axially, the extension portion moves along the slider plate thereby providing translations and axial motion in the spinal segment. The amount of translation which occurs between the extension portion 570 and the slider plate 558 can be adapted by lengthening or shortening the extension portion 558.

The extension portion 572 of the lower endplate 554 is configured with as spherical surface and is positioned tightly within a second cavity in the inner portion of the flexible core element 556. The configuration of the extension portion 556 provides flexion and extension motion when the lower endplate 454 is moved by the natural movements of the spine.

The disc assembly 550 is also provided with a central shaft in which a cord 560 is utilized to attach the assembly 550 as a single structure. The cord 560 may be composed any elastic or flexible material that is biocompatible. The cord 560 has a first end 576 and second end 578 that configured to be slightly larger than the body of the cord 560. This configuration allows the cord 560 to retained within the disc assembly 550. However, any structural or mechanical configuration that retains the cord 560 within the disc assembly may 550 be utilized. For instance, cord 560 may be attached to the endplates 552, 562 through a clip or a set screw.

The cord 560 may also be tensioned so that the assembly 550 is firmly held together. The tension of the cord 560 may vary depending on how much motion is required for the specific patient requiring the disc assembly implant 550. The characteristics of the cord 560 may be changed depending on what is required, for instance, the cord may be composed of a solid flexible material or a be a hollow member. The cord 560 may also be positioned in various locations through the disc assembly. For example, a single cord may be placed on the perimeter of the disc assembly or in position along the surface of the endplates. In another embodiment, the disc assembly may use a plurality of cords to attach the assembly as a single structure and to restrict the rotational motion of the disc assembly. When multiple cords are used, the cords may spaced apart in any location along the perimeter of the endplates to achieve the optimal results for either limiting or allowing motion in the disc assembly as well as maintaining the structural integrity of the disc assembly. In another embodiment, the core may be comprised of various flexible elements having different flexibilities and/or durometers.

Figure 124:
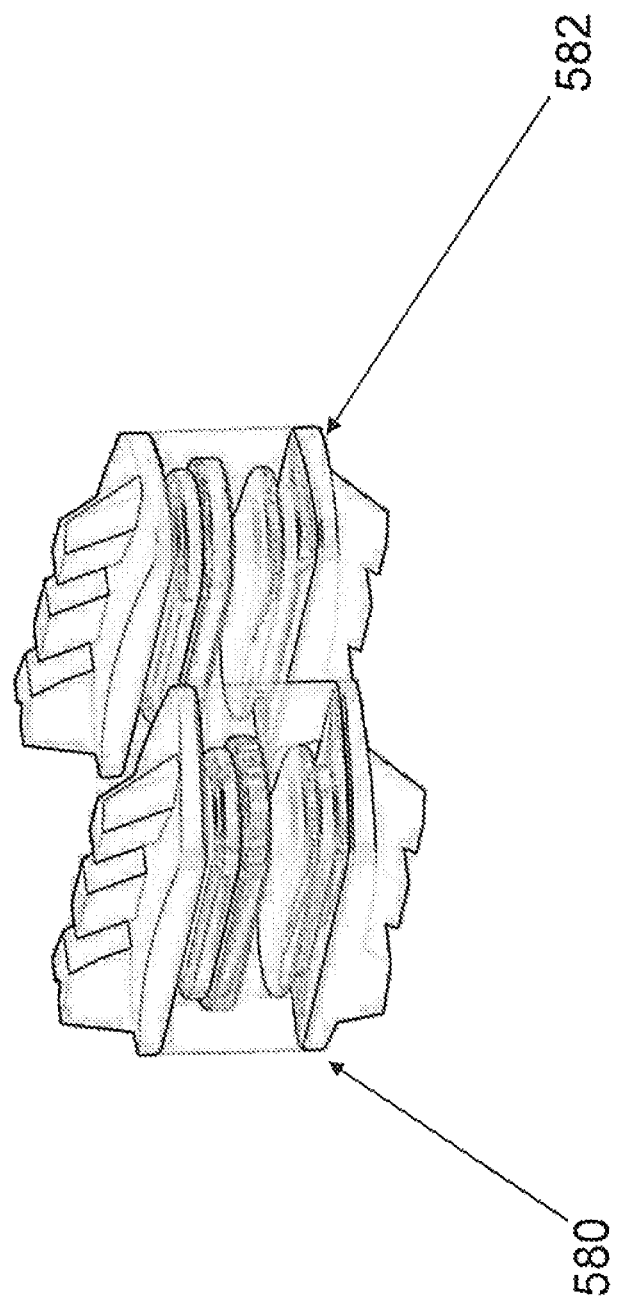
FIG. 124 illustrate two disc assemblies according to the present invention.
Figure 125:
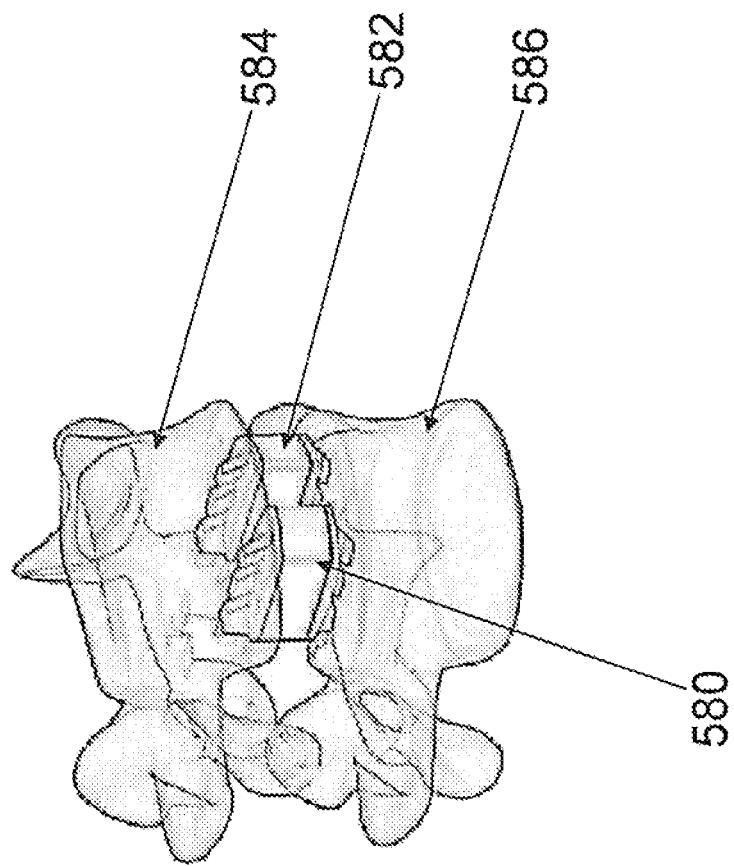
FIGS. 125 and 126 illustrates the disc assemblies of FIG. 124 positioned in the spine.
Figure 126:
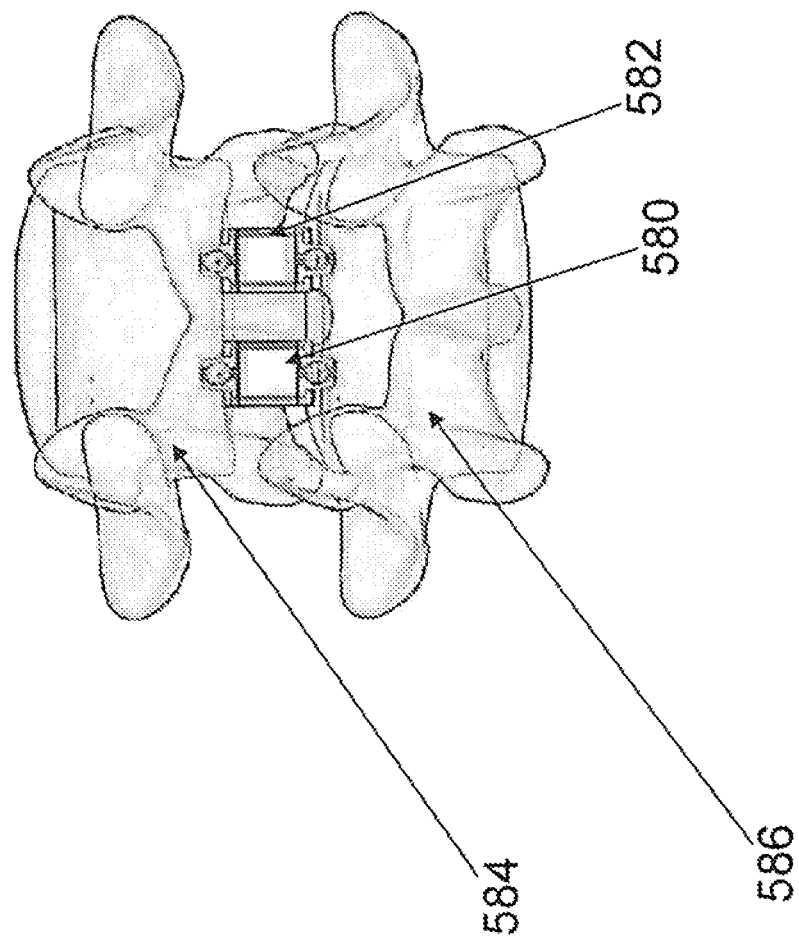

FIG. 124 illustrates two disc assemblies 580 and 582 according to the present invention. As described above, two posterior disc assemblies 580, 582 may be inserted into the intervertebral space to provide an optimal solution for disc replacement. The positioning of two disc assemblies allows the motion of the spine to mimic the actual motion of the disc nucleus. FIG. 125 illustrates the two disc assemblies 580 and 582 positioned in the intervertebral space between adjacent vertebral bodies 584 and 586. FIG. 126 illustrates a posterior view of the two disc assemblies 580 and 582 positioned in the intervertebral space of adjacent vertebral bodies 584 and 586.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

We claim:

1. An intervertebral artificial disc for positioning between a first and second vertebra, comprising:
    a first endplate having a plurality of protrusions for attaching to the first vertebrae and an extension portion extending towards the second adjacent vertebra;
    a second endplate having a plurality of protrusions for attaching to the second vertebrae and an extension portion extending towards the first vertebrae;
    a flexible member having an upper portion and a lower portion;
    a plate positioned completely within a first cavity in the upper portion of the flexible member; and,
    wherein the extension portion of the first endplate is adapted to fit within the first cavity in the upper portion of the flexible member and the extension portion of the second endplate is adapted to fit within a second cavity in the lower portion of the flexible member
    wherein the extension portion of the first endplate engages with the plate to allow translation.

2. The intervertebral artificial disc according to claim 1, wherein the first cavity in the upper portion of the flexible member is larger in length and width than the extension portion of the first endplate.

3. The intervertebral artificial disc according to claim 1, wherein the second cavity of the lower portion of the flexible member is a larger area than the extension portion of the second endplate.

4. The intervertebral artificial disc according to claim 1, wherein the extension portion of the second endplate compresses between 0.5 mm to 1 mm with respect to the flexible member.

5. The intervertebral artificial disc according to claim 1, wherein the plurality of protrusions on the first and second endplate are configured as multiple keels.

6. The intervertebral artificial disc according to claim 1, wherein a contact surface of the extension portion of the second endplate has a radius.

7. The intervertebral artificial disc according to claim 1, wherein the first endplate, the second endplate and the plate are composed of a metal.

8. The intervertebral artificial disc according to claim 1, wherein the first endplate, the second endplate and the plate are composed of a polymer.

9. An intervertebral artificial disc for positioning between a first and second vertebra, comprising:
    a first endplate having a plurality of protrusions for attaching to the first adjacent vertebrae the first endplate having an extension portion extending towards the second vertebrae;
    a second endplate having a plurality of protrusions for attaching to the second vertebrae and an extension portion extending towards the first vertebrae;
    a flexible member having an upper portion and a lower portion;
    a plate positioned completely within a first cavity in the upper portion of the flexible member; and
    wherein the extension portion of the first endplate is adapted to fit within the first cavity in the upper portion of the flexible member and the extension portion of the second endplate is adapted to fit within a second cavity in the lower portion of the flexible member at least one cord extending through the first endplate, the plate, the flexible member, and the second endplate.

10. The intervertebral artificial disc according to claim 9 wherein the extension portion of the first endplate engages with the plate to allow translation.

11. The intervertebral artificial disc according to claim 9 wherein the first cavity in the upper portion of the flexible member is dimensionally larger than the extension portion of the first endplate.

12. The intervertebral artificial disc according to claim 9 wherein the plurality of protrusions in the first and second endplate are configured as multiple keels.

13. The intervertebral artificial disc according to claim 9 wherein the second cavity of the lower portion of the flexible member is dimensionally larger than the extension portion of the second endplate.

14. The intervertebral artificial disc according to claim 9 wherein the second endplate provides flexion and extension motion with respect to the flexible member.

15. The intervertebral artificial disc according to claim 9 wherein a top surface of the extension portion of the second endplate is configured with radius.

16. The intervertebral artificial disc according to claim 9 wherein the cord is flexible.

17. The intervertebral artificial disc according to claim 9 wherein the cord is tensioned.

18. The intervertebral artificial disc according to claim 9 wherein the cord is attached to the first and second endplates with a crimp.

19. An intervertebral artificial disc positioned between a first vertebra and a second vertebrae, comprising:
    a first endplate having a plurality of protrusions for attaching to the first vertebrae and an extension portion extending towards the second vertebrae;
    a second endplate having a plurality of protrusions for attaching to a second vertebrae and an extension portion extending towards the first vertebrae;
    a flexible member having an upper portion and a lower portion;
    a plate positioned completely within a first cavity in the upper portion of the flexible member; and wherein the extension portion of the first endplate is adapted to fit within the first cavity in the upper portion of the flexible member and the extension portion of the second endplate is adapted to fit within a second cavity in the lower portion of the flexible member a first cord extending through the first endplate, the plate, the flexible member, and the second endplate;
    a second cord spaced apart from the first cord extending through the first endplate, the plate flexible member and the second endplate wherein the first and second cord restrict rotational motion of the intervertebral disc, and wherein the extension portion of the first endplate engages with the plate to allow for translation of the first endplate plate with respect to the second endplate.

* * * * *